(12) United States Patent
Sugiyama et al.

(10) Patent No.: US 7,666,985 B2
(45) Date of Patent: Feb. 23, 2010

(54) HLA-A24-RESTRICTED CANCER ANTIGEN PEPTIDES

(75) Inventors: Haruo Sugiyama, Minoo (JP); Masashi Gotoh, Takatsuki (JP); Hideo Takasu, Nishinomiya (JP)

(73) Assignees: International Institute of Cancer Immunology, Inc., Suita-shi (JP); Chugai Seiyaku Kabushiki Kaisha, Tokyo-to (JP); Dainippon Sumitomo Pharma Co., Ltd., Osaka-shi (JP)

( * ) Notice: Subject to any disclaimer, the term of this patent is extended or adjusted under 35 U.S.C. 154(b) by 44 days.

(21) Appl. No.: 12/142,372

(22) Filed: Jun. 19, 2008

(65) Prior Publication Data

US 2009/0099090 A1 Apr. 16, 2009

Related U.S. Application Data

(62) Division of application No. 10/517,600, filed as application No. PCT/JP03/07463 on Jun. 12, 2003, now Pat. No. 7,420,034.

(30) Foreign Application Priority Data

Jun. 12, 2002 (JP) ............................. 2002-171518
Sep. 20, 2002 (JP) ............................. 2002-275572

(51) Int. Cl.
*C08G 69/10* (2006.01)
*A61K 38/00* (2006.01)
*A61K 51/00* (2006.01)

(52) U.S. Cl. ........................... 530/328; 514/2; 424/1.69
(58) Field of Classification Search ........................ None
See application file for complete search history.

(56) References Cited

U.S. PATENT DOCUMENTS

| 6,034,235 A | 3/2000 | Sugiyama et al. |
| 7,420,034 B2 * | 9/2008 | Sugiyama et al. ........... 530/328 |
| 2003/0092656 A1 | 5/2003 | Sugiyama |
| 2004/0097703 A1 | 5/2004 | Sugiyama |
| 2004/0247609 A1 | 12/2004 | Sugiyama |
| 2005/0002951 A1 | 1/2005 | Sugiyama et al. |
| 2005/0266014 A1 | 12/2005 | Sugiyama et al. |

FOREIGN PATENT DOCUMENTS

EP 1 103 564 A1 5/2001

WO WO 00/18795 A2 4/2000

OTHER PUBLICATIONS

Oka, Yoshihiro et al., "Human Cytotoxic T-Iymphocyte responses specific for peptides of the Wild-type Wilms' tumor gene (WT1) Product", Immunogenetics, vol. 51, No. 2, pp. 99-107, 2000.
Kubo, Ralph T. et al., "Definition of Specific Peptide Motifs for Four Major HLA—A Alleles", The American Association of Immunologists, vol. 152, pp. 3913-3924, 1994.
Azuma, T. et al., British Journal of Haematology, vol. 116, pp. 601-603, (2002).
Ohminami, H. et al., Blood, vol. 95, No. 1, pp. 286-292, Jan. 1, 2000.
Rosenberg, S. et al., Immunity, vol. 10, pp. 281-287, Mar. 1999.
Bakker, A. et al., J. Exp. Med., vol. 179, pp. 1005-1009, Mar. 1994.
Kawakami, Y. et al., Proc. Natl. Acad. Sci. USA, vol. 91, pp. 3515-3519, Apr. 1994.
Brichard, V. et al., J. Exp. Med. vol. 178, pp. 489-495, Aug. 1993.
Fisk, B. et al., J. Exp. Med., vol. 181, pp. 2109-2117, Jun. 1995.
Tsang, K. et al., J. Natl. Cancer Inst. vol. 87, pp. 982-990, Jul. 5, 1995.
Correale, P. et al., J. Natl. Cancer Inst. vol. 89, No. 4, pp. 293-300, Feb. 19, 1997.
Melief, C. et al., Cur. Opin. Immunol., vol. 5, pp. 709-713, (1993).
Pardoll, D., Cur. Opin Immunol., vol. 5, pp. 719-725, (1993).
Nanda, N. et al., Cell, vol. 82, pp. 13-17, Jul. 14, 1995.
Melief, C. et al., Immunol. Rev., vol. 146, pp. 167-177, (1995).
Gessler, M. et al., Nature, vol. 343, pp. 774-778, Feb. 22, 1990.
Call, K. et al., Cell, vol. 60, pp. 509-520 (1990).
Oka, Y. et al., J. Immunol., vol. 164, pp. 1873-1880, (2000).
Tsuboi, A. et al., J. Clin. Immunol., vol. 20, No. 3, pp. 195-202, (2000).
The 31st Annual Meeting of the Japanese Society of Immunology, pp. 160, 2-C-W11-8P, Abstract enclosed. (2001).
Azuma, T., et al., "Identification of a Novel WT1-Derived Pepetide Which Induces Human Leucocyte Antigen-A24-Restricted Anti-Leukaemia Cytotoxic T Lymphocytes", British Journal of Haematology, Mar. 2002, vol. 116, No. 3, pp. 601-603.
Ohminami, H., et al., "HLA Class I-Restricted Lysis of Leukemia Cells by a CD8 Cytotoxic T-Lymphocyte Clone Specific for WT1 Peptide", Blood, Jan. 2000, vol. 95, No. 1, pp. 286-292.
U.S. Appl. No. 12/095,418, filed May 29, 2008, Nishihara et al.
U.S. Appl. No. 12/181,938, filed Jul. 29, 2008, Sugiyama et al.

* cited by examiner

*Primary Examiner*—Maury Audet
(74) *Attorney, Agent, or Firm*—Oblon, Spivak, McClelland, Maier & Neustadt, L.L.P.

(57) ABSTRACT

HLA-A24-restricted peptides derived from WT1 which have an activity to induce CTLs in vivo, polynucleotides encoding said peptides, cancer vaccines using those peptides or polynucleotides in vivo or in vitro, or the like are provided. The cancer vaccines of the present invention may be used to treat many cancer patients.

4 Claims, 25 Drawing Sheets

Upper: HLA-A2402/Kb genome
Lower: HLA-A2402/Kb cDNA

```
AAGCTTACTC TCTGGCACCA AACTCCATGG GATGATTTTT CTTCTAGAAG AGTCCAGGTG GACAGGTAAG GAGTGGGAGT CAGGGAGTCC AGTTCAGGGA  100
---------- ---------- ---------- ---------- ---------- ---------- ---------- ---------- ---------- ----------

CAGAGATTAC GGGATGAAAA GTGAAAGGAG AGGACGGGG CCCATGCCGA GGGTTTCTCC CTTGTTTCTC AGACAGCTCT TGGGCCAAGA TTCAGGGAGA  200
---------- ---------- ---------- ---------- ---------- ---------- ---------- ---------- ---------- ----------

CATTGAGACA GAGCGCTTGG CACAGAAGCA GAGGGGTCAG GGCGAAGTCC CAGGGCCCCA GGCGTGGCTC TCAGGTCTC AGGCCCCGAA GGCCGTGTAT  300
---------- ---------- ---------- ---------- ---------- ---------- ---------- ---------- ---------- ----------

GGATTGGGGA GTCCCAGCCT TGGGGATTCC CCAACTCCGC AGTTTCTTTT CTCCCTCTCC CAACCTATGT AGGGTCCTTC TTCCTGGATA CTCACGACGC  400
---------- ---------- ---------- ---------- ---------- ---------- ---------- ---------- ---------- ----------

GGACCCAGTT CTCACTCCCA TTGGGTGTCG GGTTTCCAGA GAAGCCAATC AGTGTGTCG CGGTCGCTGT TCTAAAGTCC GCACGCACCC ACCGGGACTC  500
---------- ---------- ---------- ---------- ---------- ---------- ---------- ---------- ---------- ----------

AGATTCTCCC CAGAGCCCGA G͟G͟A͟T͟G͟G͟C͟C͟G͟T͟ ͟C͟A͟T͟G͟G͟G͟C͟C͟C͟C͟ ͟C͟G͟A͟A͟C͟C͟C͟T͟C͟G͟ ͟T͟C͟C͟T͟G͟C͟T͟A͟C͟T͟ ͟C͟T͟C͟G͟G͟G͟G͟G͟C͟C͟ ͟C͟T͟G͟G͟C͟C͟C͟T͟G͟A͟ ͟C͟C͟C͟A͟G͟A͟C͟C͟T͟G͟ ͟G͟G͟C͟A͟G͟TGAG  600
---------- ---------- ---------- A͟T͟G͟G͟C͟C͟G͟T͟ ͟C͟A͟T͟G͟G͟G͟C͟C͟C͟C͟ ͟C͟G͟A͟A͟C͟C͟C͟T͟C͟G͟ ͟T͟C͟C͟T͟G͟C͟T͟A͟C͟T͟ ͟C͟T͟C͟G͟G͟G͟G͟C͟C͟ ͟C͟T͟G͟G͟C͟C͟C͟T͟G͟A͟ ͟C͟C͟C͟A͟G͟A͟C͟C͟T͟G͟ ͟G͟G͟C͟A͟G͟----   73
```

*Fig. 3A*

Upper: HLA-A2402/Kb genome
Lower: HLA-A2402/Kb cDNA

```
TGCGGGGTCG GGAGGAAAC GGCCTCTGCG GGGAGAAGCA AGGGGCCCGC CTGGCGGGGG CGGAAGACCC GGGAAGCCGC GCCGGGAGGA GGGTCGGGCG   700
---------- ---------- ---------- ---------- ---------- ---------- ---------- ---------- ---------- ----------    73
GGTCTCAGCC ACTCCTCGTC CCCAGCTCC  CACTCCATGA GGTATTTCTC CACATCCGTG TCCCGGCCCG GCCGCGGGGA GCCCCGCTTC ATCGCCGTGG   800
---------- ---------- -----GCTCC CACTCCATGA GGTATTTCTC CACATCCGTG TCCCGGCCCG GCCGCGGGGA GCCCCGCTTC ATCGCCGTGG   148
GCTACGTGGA CGACACGCAG TTCGTGCGGT TCGACAGCGA CGCCGCGAGC CAGAGGATGG AGCCGCGGGC GCCGTGGATA GAGCAGGAGG GGCCGGAGTA   900
GCTACGTGGA CGACACGCAG TTCGTGCGGT TCGACAGCGA CGCCGCGAGC CAGAGGATGG AGCCGCGGGC GCCGTGGATA GAGCAGGAGG GGCCGGAGTA   248
TTGGGACGAG GAGACAGGGA AAGTGAAGGC CCACTCACAG ACTGACGGAG AGAACCTGCG GATCGCGCTC CGCTACTACA ACCAGAGCGA GGCCGGTGAG  1000
TTGGGACGAG GAGACAGGGA AAGTGAAGGC CCACTCACAG ACTGACGGAG AGAACCTGCG GATCGCGCTC CGCTACTACA ACCAGAGCGA GGCCG-----   343
TGACCCCGGC CCGGGGCGCA GGTCACGACC CCTCATCCCC CACGGACGGG CCCGGGTCGCC CACAGTCTCC GGGTCCGAGA TCCACCCCGA AGCCGCGGGA  1100
---------- ---------- ---------- ---------- ---------- ---------- ---------- ---------- ---------- ----------   343
CCCCGAGACC CTTGCCCCGG GAGAGGCCCA GGGGCCTTAA CCCGGTTTCA TTTTCAGTTT AGGCCAAAAA TCCCCCCGGG TTGGTCGGGG CCGGGGCGGG  1200
---------- ---------- ---------- ---------- ---------- ---------- ---------- ---------- ---------- ----------   343
```

*Fig. 3B*

Upper: HLA-A2402/Kb genome
Lower: HLA-A2402/Kb cDNA

Upper: HLA-A2402/Kb genome
Lower: HLA-A2402/Kb cDNA

| | | | | | | | |
|---|---|---|---|---|---|---|---|
| ATGCTATTGA | ACATCACATA | AGGATGGCCA | TGTTTACCCA | ATGGCTCATG | TGGATTCCCT | CTTAGCTTCT | GAGTCCCAAA | AGAAAATGTG | CAGTCCTGTG | 1900 |
| ---------- | ---------- | ---------- | ---------- | ---------- | ---------- | ---------- | ---------- | ---------- | ---------- | 619 |
| CTGAGGGGAC | CAGTCTCTGCT | TTTGGTCACT | AGTGCGATGA | CAGTTGAAGT | GTCAAACAGA | CACATAGTTC | ACTGTCATCA | TTGATTTAAC | TGAGTCTTGG | 2000 |
| ---------- | ---------- | ---------- | ---------- | ---------- | ---------- | ---------- | ---------- | ---------- | ---------- | 619 |
| GTAGATTTCA | GTTTGTCTTG | TTAATTGTGT | GATTTCTTAA | ATCTTCCACA | CAGATTCCCC | AAAGGCCCAT | GTGACCCATC | ACAGCAGACC | TGAAGATAAA | 2100 |
| ---------- | ---------- | ---------- | ---------- | ---------- | ---------- | -ATCCCC    | AAAGGCCCAT | GTGACCCATC | ACAGCAGACC | TGAAGATAAA | 666 |
| GTCACCCTGA | GGTGCTGGGC | CCTGGGCTTC | TACCCTGCTG | ACATCACCCT | GACCTGGCAG | TTGAATGGGG | AGGAGCTGAT | CCAGGACATG | GAGCTTGTGG | 2200 |
| GTCACCCTGA | GGTGCTGGGC | CCTGGGCTTC | TACCCTGCTG | ACATCACCCT | GACCTGGCAG | TTGAATGGGG | AGGAGCTGAT | CCAGGACATG | GAGCTTGTGG | 766 |
| AGACCAGGCC | TGCAGGGGAT | GGAACCTTCC | AGAAGTGGGC | ATCTGTGGTG | GTGCCTCTTG | GGAAGGAGCA | GTATTACACA | TGCCATGTGT | ACCATCAGGG | 2300 |
| AGACCAGGCC | TGCAGGGGAT | GGAACCTTCC | AGAAGTGGGC | ATCTGTGGTG | GTGCCTCTTG | GGAAGGAGCA | GTATTACACA | TGCCATGTGT | ACCATCAGGG | 866 |
| GCTGCCTGAG | CCCCTCACCC | TGAGATGGGG | TAAGGAGAGT | GTGGGTGCAG | AGCTGGGGTC | AGGGAAAGCT | AGGGAAAGCT | GGAACCCTG | AGCTGCTCAG | 2400 |
| GCTGCCTGAG | CCCCTCACCC | TGAGATGGG- | ---------- | ---------- | ---------- | ---------- | ---------- | ---------- | ---------- | 895 |

Fig.4B

Upper: HLA-A2402/Kb genome
Lower: HLA-A2402/Kb cDNA

```
GGCTGAGAGC TGGGGTCATG ACCCTCACCT TCATTTCTTG TACCTGTCCT TCCCAGAGCC TCCTCCATCC ACTGTCTCCA ACATGGCGAC CGTTGCTGTT 2500
---------- ---------- ---------- ---------- ---------- ----AGCC TCCTCCATCC ACTGTCTCCA ACATGGCGAC CGTTGCTGTT  939
CTGGTTGTCC TTGGAGCTGC AATAGTCACT GGAGCTGTGG TGGCTTTTGT GATGAAGATG AGAAGGAGAA ACACAGTAG- ---------- ----------  
CTGGTTGTCC TTGGAGCTGC AATAGTCACT GGAGCTGTGG TGGCTTTTGT GATGAAGATG AGAAGGAGAA ACACAG---- ---------- ---------- 1015
```

Fig.4C

```
TTCTCTCAGC CTCCCTTAGA GTGTGCTCTG CTCATCAATG GGGAACACAG GCACACCCCA CATTGCTACT GTCTCTAACT GGGTCTGCTG TCAGTCTGG 2600
---------- ---------- ---------- ---------- ---------- ---------- ---------- ---------- ---------- --------- 1015
GAACTTCCTA GTGTCAAGAT CTTCCTGGAA CTCTCACAGC TTTTCTCTC ACAGTGGAA AAGGAGGGGA CTATGCTCTG GCTCCAGTT AGTGTGGGA 2800
---------- ---------- ---------- ---------- ---------- ----GTGGAA AAGGAGGGGA CTATGCTCTG GCTCCAG--- ---------- 1048
CAGAGTTGTC CTGGGACAT TGGAGTGAAG TTGGAGATGA TGGAGCTCT GGGAATCCAT AATAGCTCCT CCAGAGAAAT CTTCTAGGTG CCTGAGTTGT 2900
---------- ---------- ---------- ---------- ---------- ---------- ---------- ---------- ---------- ---------- 1048
GCCATGAAAT GAATATGTAC ATGTACACATAT TTGTTTTGTT TTACCCTAGG CTCCCAGACC TCTGATCTGT CTCTCCCAGA TTGTAAAGGT 3000
---------- ---------- ---------- ---------- ----------G CTCCCAGACC TCTGATCTGT CTCTCCCAGA TTGTAAAG-- 1087
```

Fig.5A

Upper: HLA-A2402/Kb genome
Lower: HLA-A2402/Kb cDNA

```
GACACTCTAG GGTCTGATTG GGGAGGGGCA ATGTGGACAT GATTGGGTTT CAGGAACTCC CAGAATCCCC TGTGAGTGAG TGATGGGTTG TTCGAATGTT 3100
---------- ---------- ---------- ---------- ---------- ---------- ---------- ---------- ---------- ----------  1087

GTCTTCACAG TGATGGTTCA TGACCCTCAT TCTCTAGCGT GAAGACAGCT GCCTGGAGTG GACTTGGTGA CAGACAATGT CTTCTCATAT CTCCCTGTGAC 3200
---------- TGATGGTTCA TGACCCTCAT TCTCTAGCGT GA-------- ---------- ---------- ---------- ---------- ----------  1119

ATCCAGAGCC CTCAGTTCTC TTTAGTCAAG TGTCTGATGT TCCCTGTGAG TCCCTTCCACA GCCAACCTTG CTGGTTCAGC CAAACACTGA GGGACATCTG TAGCCTGTCA CCCTCTACAC 3300
---------- ---------- ---------- ---------- ---------- ---------- ---------- ---------- ---------- ----------  1119

CAGGACCCTG TCCCTGCACT GCTCTGTCTT CCCTTCCACA GCCAACCTTG CTGGTTCAGC CAAACACTGA GGGACATCTG TAGCCTGTCA GCTCCATGCT 3400
---------- ---------- ---------- ---------- ---------- ---------- ---------- ---------- ---------- ----------  1119

ACCCTGACCT GCAACTCCTC ACTTCCACAC TGAGAATAAT AATTTGAATG TAACCTTGAT TGTTATCATC TTGACCTAGG GCTGATTTCT TGTTAATTTC 3500
---------- ---------- ---------- ---------- ---------- ---------- ---------- ---------- ---------- ----------  1119

ATGGATTGAG AATGCTTAGA GGTTTTGTTT GTTTGTTTGA TTGATTTGTT TTTTGAAGA AATAAATGAT AGATGAATAA ACTTCCAGAA TCTGGGTCAC 3600
---------- ---------- ---------- ---------- ---------- ---------- ---------- ---------- ---------- ----------  1119
```

*Fig. 5B*

Upper: HLA-A2402/Kb genome
Lower: HLA-A2402/Kb cDNA

TATGCTGTGT GTATCTGTTG GGACAGGATG AGACTGTAGC AGCTGAGTGT GTGCCGAGGT GGGCTCAGTT TGCTTTGATC TGTGATGGGG 3700
                                                                                                    1119

CCACACCTCC ACTGTGTCAC CTCTGGGCTC TGTTCCCTCT ATCACTATGA GGCACATGCT GAGAGTTTGT GGTCACAAAG ACACAGGGAA GGCCTGAGCC 3800
                                                                                                         1119

TTGCCCTGTC CCCAGGATTA TGAGCCCCCA GGGCTAAAGA TCAGAGACTC GGAATTC 3857
                                                                1119

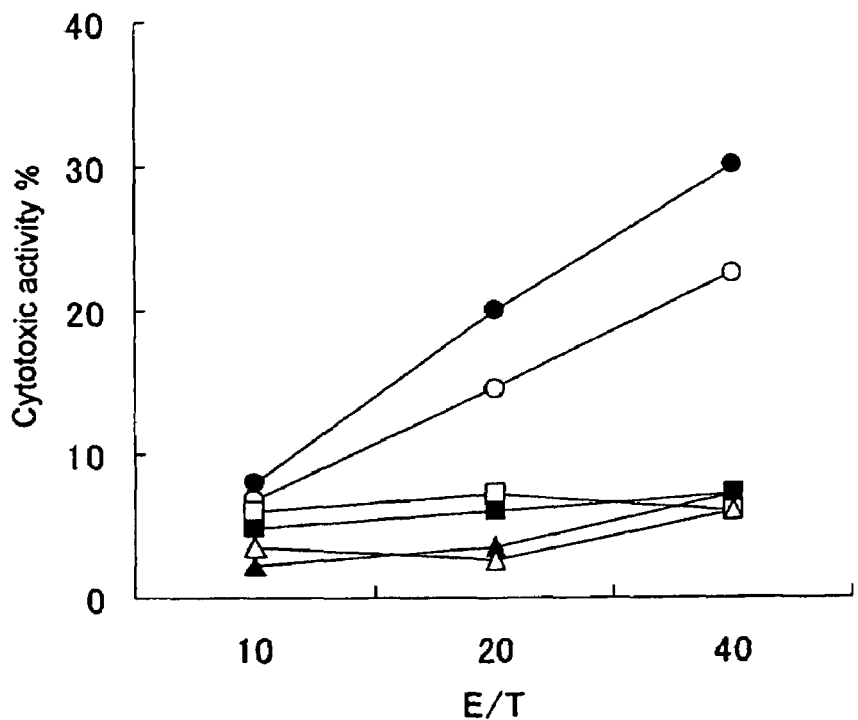

- ●— Effector cells: Altered peptide - stimulated
  Target cells: RERF-LC-AI cells (WT1 positive, HLA-A2402 positive)
- ▲— Effector cells: Altered peptide - stimulated
  Target cells: LK87 cells (WT1 positive, HLA-A2402 negative)
- ■— Effector cells: Altered peptide - stimulated
  Target cells: 11-18 cells (WT1 negative, HLA-A2402 positive)
- ○— Effector cells: Natural peptide - stimulated
  Target cells: RERF-LC-AI cells (WT1 positive HLA-A240 2 positive)
- △— Effector cells: Natural peptide - stimulated
  Target cells: LK87 cells (WT1 positive, HLA-A2402 negative)
- □— Effector cells: Natural peptide - stimulated
  Target cells: 11-18 cells (WT1 negative, HLA-A2402 positive)

SEQUENCE LISTING

```
<160> NUMBER OF SEQ ID NOS: 68

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
```

-continued

```
                    210                 215                 220
Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
            245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
                355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
            435                 440                 445

Leu
```

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

```
Arg Tyr Phe Pro Asn Ala Pro Tyr Leu
1               5
```

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

```
Arg Tyr Pro Gly Val Ala Pro Thr Leu
1               5
```

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

```
<400> SEQUENCE: 4

Arg Tyr Pro Ser Cys Gln Lys Lys Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Ala Tyr Leu Pro Ala Val Pro Ser Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Asn Tyr Met Asn Leu Gly Ala Thr Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Arg Val Pro Gly Val Ala Pro Thr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Arg Met Phe Pro Asn Ala Pro Tyr Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Sequence: Synthetic Peptide

<400> SEQUENCE: 9

Arg Trp Pro Ser Cys Gln Lys Lys Phe
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Peptide
```

```
<400> SEQUENCE: 10

Gln Tyr Arg Ile His Thr His Gly Val Phe
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 11

Ala Tyr Pro Gly Cys Asn Lys Arg Tyr Phe
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 12

Arg Tyr Phe Pro Asn Ala Pro Tyr Phe
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Arg Tyr Phe Pro Asn Ala Pro Tyr Trp
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Arg Tyr Phe Pro Asn Ala Pro Tyr Ile
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Arg Tyr Phe Pro Asn Ala Pro Tyr Met
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16
```

Arg Tyr Pro Gly Val Ala Pro Thr Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Arg Tyr Pro Gly Val Ala Pro Thr Trp
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 18

Arg Tyr Pro Gly Val Ala Pro Thr Ile
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 19

Arg Tyr Pro Gly Val Ala Pro Thr Met
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Arg Tyr Pro Ser Cys Gln Lys Lys Trp
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 21

Arg Tyr Pro Ser Cys Gln Lys Lys Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 22

```
Arg Tyr Pro Ser Cys Gln Lys Lys Ile
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 23

Arg Tyr Pro Ser Cys Gln Lys Lys Met
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 24

Ala Tyr Leu Pro Ala Val Pro Ser Phe
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 25

Ala Tyr Leu Pro Ala Val Pro Ser Trp
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26

Ala Tyr Leu Pro Ala Val Pro Ser Ile
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 27

Ala Tyr Leu Pro Ala Val Pro Ser Met
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 28

Asn Tyr Met Asn Leu Gly Ala Thr Phe
```

<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Asn Tyr Met Asn Leu Gly Ala Thr Trp
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Asn Tyr Met Asn Leu Gly Ala Thr Ile
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 31

Asn Tyr Met Asn Leu Gly Ala Thr Met
1               5

<210> SEQ ID NO 32
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 32

Phe Asn Asn Phe Thr Val Ser Phe Trp Leu Arg Val Pro Lys Val Ser
1               5                   10                  15

Ala Ser His Leu Glu
            20

<210> SEQ ID NO 33
<211> LENGTH: 3857
<212> TYPE: DNA
<213> ORGANISM: Artificial Sequence
<220> FEATURE:
<223> OTHER INFORMATION: Synthetic DNA

<400> SEQUENCE: 33
aagcttactc tctggcacca aactccatgg gatgattttt cttctagaag agtccaggtg      60
gacaggtaag gagtgggagt cagggagtcc agttcaggga cagagattac gggatgaaaa    120
gtgaaaggag agggacgggg cccatgccga gggtttctcc cttgtttctc agacagctct    180
tgggccaaga ttcagggaga cattgagaca gagcgcttgg cacagaagca gagggtcag     240 ggcgaagtcc cagggcccca ggcgtggctc tcagggtctc aggccccgaa ggcggtgtat    300
ggattgggga gtcccagcct tgggattccc caactccgc agtttctttt ctccctctcc     360

| | |
|---|---|
| caacctatgt agggtccttc ttcctggata ctcacgacgc ggacccagtt ctcactccca | 420 |
| ttgggtgtcg ggtttccaga gaagccaatc agtgtcgtcg cggtcgctgt tctaaagtcc | 480 |
| gcacgcaccc accgggactc agattctccc cagacgccga ggatggccgt catggcgccc | 540 |
| cgaaccctcg tcctgctact ctcgggggcc ctggccctga cccagacctg ggcaggtgag | 600 |
| tgcggggtcg ggagggaaac ggcctctgcg gggagaagca aggggcccgc ctggcggggg | 660 |
| cgcaagaccc gggaagccgc gccggagga gggtcgggcg ggtctcagcc actcctcgtc | 720 |
| cccaggctcc cactccatga ggtatttctc cacatccgtg tcccggcccg gccgcgggga | 780 |
| gccccgcttc atcgccgtgg gctacgtgga cgacacgcag ttcgtgcggt tcgacagcga | 840 |
| cgccgcgagc cagaggatgg agccgcgggc gccgtggata gagcaggagg ggccggagta | 900 |
| ttgggacgag gagacaggga aagtgaaggc ccactcacag actgaccgag agaacctgcg | 960 |
| gatcgcgctc cgctactaca accagagcga ggccggtgag tgaccccggc ccggggcgca | 1020 |
| ggtcacgacc cctcatcccc cacgacgggc cgggtcgcc cacagtctcc gggtccgaga | 1080 |
| tccaccccga agccgcggga ccccgagacc cttgccccgg gagaggccca ggcgccttaa | 1140 |
| cccggtttca ttttcagttt aggccaaaaa tcccccgggt tggtcgggg ccggcgggg | 1200 |
| ctcgggggac tgggctgacc gcggggtcgg ggccaggttc tcacaccctc cagatgatgt | 1260 |
| ttggctgcga cgtggggtcg gacgggcgct cctccgcgg gtaccaccag tacgcctacg | 1320 |
| acggcaagga ttacatcgcc ctgaaagagg acctgcgctc ttggaccgcg gcggacatgg | 1380 |
| cggctcagat caccaagcgc aagtgggagg cggcccatgt ggcggagcag cagagagcct | 1440 |
| acctggaggg cacgtgcgtg gacgggctcc gcagatacct ggagaacggg aaggagacgc | 1500 |
| tgcagcgcac gggtaccagg ggccacgggg cgcctacctg atcgcctgta gatcctgtgt | 1560 |
| gacacacctg taccttgtcc cccagagtca ggggctggga gtcattttct ctggctacac | 1620 |
| acttagtgat ggctgttcac ttggactgac agttaatgtt ggtcagcaag gtgactacaa | 1680 |
| tggttgagtc tcaatggtgt caccttccag gatcatacag ccctaatttt aatatgaact | 1740 |
| caaacacata ttaaattagt tattttccat tccctcctcc attctttgac tacctctctc | 1800 |
| atgctattga acatcacata aggatggcca tgttaccca atggctcatg tggattccct | 1860 |
| cttagcttct gagtcccaaa agaaaatgtg cagtcctgtg ctgaggggac cagctctgct | 1920 |
| tttggtcact agtgcgatga cagttgaagt gtcaaacaga cacatagttc actgtcatca | 1980 |
| ttgatttaac tgagtcttgg gtagatttca gtttgtcttg ttaattgtgt gatttcttaa | 2040 |
| atcttccaca cagattcccc aaaggcccat gtgacccatc acagcagacc tgaagataaa | 2100 |
| gtcaccctga ggtgctgggc cctgggcttc taccctgctg acatcaccct gacctggcag | 2160 |
| ttgaatgggg aggagctgat ccaggacatg gagcttgtgg agaccaggcc tgcaggggat | 2220 |
| ggaaccttcc agaagtgggc atctgtggtg gtgcctcttg gaaggagca gtattacaca | 2280 |
| tgccatgtgt accatcaggg gctgcctgag cccctcaccc tgagatgggg taaggagagt | 2340 |
| gtgggtgcag agctggggtc agggaaagct ggagctttct gcagaccctg agctgctcag | 2400 |
| ggctgagagc tggggtcatg accctcacct tcatttcttg tacctgtcct tcccagagcc | 2460 |
| tcctccatcc actgtctcca acatggcgac cgttgctgtt ctggttgtcc ttggagctgc | 2520 |
| aatagtcact ggagctgtgg tggcttttgt gatgaagatg agaaggagaa acacaggtag | 2580 |
| gaaagggcag agtctgagtt ttctctcagc ctcctttaga gtgtgctctg ctcatcaatg | 2640 |
| gggaacacag gcacacccca cattgctact gtctctaact gggtctgctg tcagttctgg | 2700 |
| gaacttccta gtgtcaagat cttcctggaa ctctcacagc ttttcttctc acaggtggaa | 2760 |

-continued

```
aaggagggga ctatgctctg gctccaggtt agtgtgggga cagagttgtc ctggggacat    2820
tggagtgaag ttggagatga tgggagctct gggaatccat aatagctcct ccagagaaat    2880
cttctaggtg cctgagttgt gccatgaaat gaatatgtac atgtacatat gcatatacat    2940
ttgttttgtt ttaccctagg ctcccagacc tctgatctgt ctctcccaga ttgtaaaggt    3000
gacactctag ggtctgattg ggagggggca atgtggacat gattgggttt caggaactcc    3060
cagaatcccc tgtgagtgag tgatgggttg ttcgaatgtt gtcttcacag tgatggttca    3120
tgaccctcat tctctagcgt gaagacagct gcctggagtg gacttggtga cagacaatgt    3180
cttctcatat ctcctgtgac atccagagcc ctcagttctc tttagtcaag tgtctgatgt    3240
tccctgtgag cctatggact caatgtgaag aactgtggag cccagtccac ccctctacac    3300
caggaccctg tccctgcact gctctgtctt cccttccaca gccaaccttg ctggttcagc    3360
caaacactga gggacatctg tagcctgtca gctccatgct accctgacct gcaactcctc    3420
acttccacac tgagaataat aatttgaatg taaccttgat tgttatcatc ttgacctagg    3480
gctgatttct tgttaatttc atggattgag aatgcttaga ggttttgttt gtttgtttga    3540
ttgatttgtt ttttttgaaga aataaatgat agatgaataa acttccagaa tctgggtcac    3600
tatgctgtgt gtatctgttg ggacaggatg agactgtagc agctgagtgt gaacagggct    3660
gtgccgaggt gggctcagtt tgctttgatc tgtgatgggg ccacacctcc actgtgtcac    3720
ctctgggctc tgttccctct atcactatga ggcacatgct gagagtttgt ggtcacaaag    3780
acacagggaa ggcctgagcc ttgccctgtc cccaggatta tgagccccca gggctaaaga    3840
tcagagactc ggaattc                                                    3857
```

<210> SEQ ID NO 34
<211> LENGTH: 1119
<212> TYPE: DNA
<213> ORGANISM: Artificial Sequence
<220> FEATURE:
<223> OTHER INFORMATION: Synthetic DNA

<400> SEQUENCE: 34

```
atg gcc gtc atg gcg ccc cga acc ctc gtc ctg cta ctc tcg ggg gcc      48
Met Ala Val Met Ala Pro Arg Thr Leu Val Leu Leu Leu Ser Gly Ala
1               5                   10                  15 ctg gcc ctg acc cag acc tgg gca ggc tcc cac tcc atg agg tat ttc      96
Leu Ala Leu Thr Gln Thr Trp Ala Gly Ser His Ser Met Arg Tyr Phe
            20                  25                  30 tcc aca tcc gtg tcc cgg ccc ggc cgc ggg gag ccc cgc ttc atc gcc     144
Ser Thr Ser Val Ser Arg Pro Gly Arg Gly Glu Pro Arg Phe Ile Ala
        35                  40                  45 gtg ggc tac gtg gac gac acg cag ttc gtg cgg ttc gac agc gac gcc     192
Val Gly Tyr Val Asp Asp Thr Gln Phe Val Arg Phe Asp Ser Asp Ala
    50                  55                  60 gcg agc cag agg atg gag ccg cgg gcg ccg tgg ata gag cag gag ggg     240
Ala Ser Gln Arg Met Glu Pro Arg Ala Pro Trp Ile Glu Gln Glu Gly
65                  70                  75                  80 ccg gag tat tgg gac gag gag aca ggg aaa gtg aag gcc cac tca cag     288
Pro Glu Tyr Trp Asp Glu Glu Thr Gly Lys Val Lys Ala His Ser Gln
                85                  90                  95 act gac cga gag aac ctg cgg atc gcg ctc cgc tac tac aac cag agc     336
Thr Asp Arg Glu Asn Leu Arg Ile Ala Leu Arg Tyr Tyr Asn Gln Ser
            100                 105                 110 gag gcc ggt tct cac acc ctc cag atg atg ttt ggc tgc gac gtg ggg     384
Glu Ala Gly Ser His Thr Leu Gln Met Met Phe Gly Cys Asp Val Gly
        115                 120                 125
```

```
                    115                 120                 125
tcg gac ggg cgc ttc ctc cgc ggg tac cac cag tac gcc tac gac ggc       432
Ser Asp Gly Arg Phe Leu Arg Gly Tyr His Gln Tyr Ala Tyr Asp Gly
        130                 135                 140 aag gat tac atc gcc ctg aaa gag gac ctg cgc tct tgg acc gcg gcg       480
Lys Asp Tyr Ile Ala Leu Lys Glu Asp Leu Arg Ser Trp Thr Ala Ala
145                 150                 155                 160 gac atg gcg gct cag atc acc aag cgc aag tgg gag gcg gcc cat gtg       528
Asp Met Ala Ala Gln Ile Thr Lys Arg Lys Trp Glu Ala Ala His Val
                165                 170                 175 gcg gag cag cag aga gcc tac ctg gag ggc acg tgc gtg gac ggg ctc       576
Ala Glu Gln Gln Arg Ala Tyr Leu Glu Gly Thr Cys Val Asp Gly Leu
            180                 185                 190 cgc aga tac ctg gag aac ggg aag gag acg ctg cag cgc acg gat tcc       624
Arg Arg Tyr Leu Glu Asn Gly Lys Glu Thr Leu Gln Arg Thr Asp Ser
        195                 200                 205 cca aag gcc cat gtg acc cat cac agc aga cct gaa gat aaa gtc acc       672
Pro Lys Ala His Val Thr His His Ser Arg Pro Glu Asp Lys Val Thr
    210                 215                 220 ctg agg tgc tgg gcc ctg ggc ttc tac cct gct gac atc acc ctg acc       720
Leu Arg Cys Trp Ala Leu Gly Phe Tyr Pro Ala Asp Ile Thr Leu Thr
225                 230                 235                 240 tgg cag ttg aat ggg gag gag ctg atc cag gac atg gag ctt gtg gag       768
Trp Gln Leu Asn Gly Glu Glu Leu Ile Gln Asp Met Glu Leu Val Glu
                245                 250                 255 acc agg cct gca ggg gat gga acc ttc cag aag tgg gca tct gtg gtg       816
Thr Arg Pro Ala Gly Asp Gly Thr Phe Gln Lys Trp Ala Ser Val Val
            260                 265                 270 gtg cct ctt ggg aag gag cag tat tac aca tgc cat gtg tac cat cag       864
Val Pro Leu Gly Lys Glu Gln Tyr Tyr Thr Cys His Val Tyr His Gln
        275                 280                 285 ggg ctg cct gag ccc ctc acc ctg aga tgg gag cct cct cca tcc act       912
Gly Leu Pro Glu Pro Leu Thr Leu Arg Trp Glu Pro Pro Pro Ser Thr
    290                 295                 300 gtc tcc aac atg gcg acc gtt gct gtt ctg gtt gtc ctt gga gct gca       960
Val Ser Asn Met Ala Thr Val Ala Val Leu Val Val Leu Gly Ala Ala
305                 310                 315                 320 ata gtc act gga gct gtg gtg gct ttt gtg atg aag atg aga agg aga      1008
Ile Val Thr Gly Ala Val Val Ala Phe Val Met Lys Met Arg Arg Arg
                325                 330                 335 aac aca ggt gga aaa gga ggg gac tat gct ctg gct cca ggc tcc cag      1056
Asn Thr Gly Gly Lys Gly Gly Asp Tyr Ala Leu Ala Pro Gly Ser Gln
            340                 345                 350 acc tct gat ctg tct ctc cca gat tgt aaa gtg atg gtt cat gac cct      1104
Thr Ser Asp Leu Ser Leu Pro Asp Cys Lys Val Met Val His Asp Pro
        355                 360                 365 cat tct cta gcg tga                                                   1119
His Ser Leu Ala
    370

<210> SEQ ID NO 35
<211> LENGTH: 372
<212> TYPE: PRT
<213> ORGANISM: Artificial Sequence
<220> FEATURE:
<223> OTHER INFORMATION: Synthetic Peptide

<400> SEQUENCE: 35

Met Ala Val Met Ala Pro Arg Thr Leu Val Leu Leu Leu Ser Gly Ala
1               5                   10                  15
```

-continued

Leu Ala Leu Thr Gln Thr Trp Ala Gly Ser His Ser Met Arg Tyr Phe
            20                  25                  30

Ser Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Glu Glu Thr Gly Lys Val Lys Ala His Ser Gln
                85                  90                  95

Thr Asp Arg Glu Asn Leu Arg Ile Ala Leu Arg Tyr Tyr Asn Gln Ser
            100                 105                 110

Glu Ala Gly Ser His Thr Leu Gln Met Met Phe Gly Cys Asp Val Gly
        115                 120                 125

Ser Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Ile Thr Lys Arg Lys Trp Glu Ala Ala His Val
                165                 170                 175

Ala Glu Gln Gln Arg Ala Tyr Leu Glu Gly Thr Cys Val Asp Gly Leu
            180                 185                 190

Arg Arg Tyr Leu Glu Asn Gly Lys Glu Thr Leu Gln Arg Thr Asp Ser
        195                 200                 205

Pro Lys Ala His Val Thr His His Ser Arg Pro Glu Asp Lys Val Thr
    210                 215                 220

Leu Arg Cys Trp Ala Leu Gly Phe Tyr Pro Ala Asp Ile Thr Leu Thr
225                 230                 235                 240

Trp Gln Leu Asn Gly Glu Glu Leu Ile Gln Asp Met Glu Leu Val Glu
                245                 250                 255

Thr Arg Pro Ala Gly Asp Gly Thr Phe Gln Lys Trp Ala Ser Val Val
            260                 265                 270

Val Pro Leu Gly Lys Glu Gln Tyr Tyr Thr Cys His Val Tyr His Gln
        275                 280                 285

Gly Leu Pro Glu Pro Leu Thr Leu Arg Trp Glu Pro Pro Ser Thr
    290                 295                 300

Val Ser Asn Met Ala Thr Val Ala Val Leu Val Leu Gly Ala Ala
305                 310                 315                 320

Ile Val Thr Gly Ala Val Val Ala Phe Val Met Lys Met Arg Arg Arg
                325                 330                 335

Asn Thr Gly Gly Lys Gly Gly Asp Tyr Ala Leu Ala Pro Gly Ser Gln
            340                 345                 350

Thr Ser Asp Leu Ser Leu Pro Asp Cys Lys Val Met Val His Asp Pro
        355                 360                 365

His Ser Leu Ala
    370

<210> SEQ ID NO 36
<211> LENGTH: 36
<212> TYPE: DNA
<213> ORGANISM: Artificial Sequence
<220> FEATURE:
<223> OTHER INFORMATION: Synthetic DNA

<400> SEQUENCE: 36
cccaagctta ctctctggca ccaaactcca tgggat          36

<210> SEQ ID NO 37
<211> LENGTH: 30
<212> TYPE: DNA
<213> ORGANISM: Artificial Sequence
<220> FEATURE:
<223> OTHER INFORMATION: Synthetic DNA

<400> SEQUENCE: 37
cgggagatct acaggcgatc aggtaggcgc          30

<210> SEQ ID NO 38
<211> LENGTH: 30
<212> TYPE: DNA
<213> ORGANISM: Artificial Sequence
<220> FEATURE:
<223> OTHER INFORMATION: Synthetic DNA

<400> SEQUENCE: 38
cgcaggctct cacactattc aggtgatctc          30

<210> SEQ ID NO 39
<211> LENGTH: 38
<212> TYPE: DNA
<213> ORGANISM: Synthetic DNA
<220> FEATURE:
<223> OTHER INFORMATION: Synthetic DNA

<400> SEQUENCE: 39
cggaattccg agtctctgat ctttagccct gggggctc          38

<210> SEQ ID NO 40
<211> LENGTH: 29
<212> TYPE: DNA
<213> ORGANISM: Artificial Sequence
<220> FEATURE:
<223> OTHER INFORMATION: Synthetic DNA

<400> SEQUENCE: 40
aggacttgga ctctgagagg cagggtctt          29

<210> SEQ ID NO 41
<211> LENGTH: 30
<212> TYPE: DNA
<213> ORGANISM: Artificial Sequence
<220> FEATURE:
<223> OTHER INFORMATION: Synthetic DNA

<400> SEQUENCE: 41
catagtcccc tccttttcca cctgtgagaa          30

<210> SEQ ID NO 42
<211> LENGTH: 23
<212> TYPE: DNA
<213> ORGANISM: Artificial Sequence
<220> FEATURE:
<223> OTHER INFORMATION: Synthetic DNA

<400> SEQUENCE: 42
cgaaccctcg tcctgctact ctc          23

<210> SEQ ID NO 43
<211> LENGTH: 23
<212> TYPE: DNA
<213> ORGANISM: Artificial Sequence
<220> FEATURE:
<223> OTHER INFORMATION: Synthetic DNA

<400> SEQUENCE: 43
agcatagtcc cctccttttc cac                                        23

<210> SEQ ID NO 44
<211> LENGTH: 39
<212> TYPE: DNA
<213> ORGANISM: Artificial Sequence
<220> FEATURE:
<223> OTHER INFORMATION: Synthetic DNA

<400> SEQUENCE: 44
cccaagcttc gccgaggatg gccgtcatgg cgccccgaa                       39

<210> SEQ ID NO 45
<211> LENGTH: 41
<212> TYPE: DNA
<213> ORGANISM: Artificial Sequence
<220> FEATURE:
<223> OTHER INFORMATION: Synthetic DNA

<400> SEQUENCE: 45
ccggaattct gtcttcacgc tagagaatga gggtcatgaa c                    41

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 46

Pro Tyr Val Ser Arg Leu Leu Gly Ile
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 47

Ile Met Pro Lys Ala Gly Leu Leu Ile
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 48

Thr Tyr Ala Cys Phe Val Ser Asn Leu
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 49

```
Gln Tyr Ser Trp Phe Val Asn Gly Thr Phe
1               5                   10
```

<210> SEQ ID NO 50
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 50

```
Ala Gln Tyr Ile Lys Ala Asn Ser Lys Phe Ile Gly Ile Thr Glu Leu
1               5                   10                  15
```

<210> SEQ ID NO 51
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 51

```
Ala Leu Leu Pro Ala Val Pro Ser Leu
1               5
```

<210> SEQ ID NO 52
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 52

```
Asn Gln Met Asn Leu Gly Ala Thr Leu
1               5
```

<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 53

```
Arg Phe Phe Pro Asn Ala Pro Tyr Leu
1               5
```

<210> SEQ ID NO 54
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 54

```
Arg Trp Phe Pro Asn Ala Pro Tyr Leu
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 55

```
Arg Phe Pro Gly Val Ala Pro Thr Leu
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 56

```
Arg Met Pro Gly Val Ala Pro Thr Leu
1               5
```

<210> SEQ ID NO 57
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 57

```
Arg Trp Pro Gly Val Ala Pro Thr Leu
1               5
```

<210> SEQ ID NO 58
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 58

```
Arg Phe Pro Ser Cys Gln Lys Lys Phe
1               5
```

<210> SEQ ID NO 59
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 59

```
Arg Met Pro Ser Cys Gln Lys Lys Phe
1               5
```

<210> SEQ ID NO 60
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 60

```
Ala Phe Leu Pro Ala Val Pro Ser Leu
1               5
```

<210> SEQ ID NO 61
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 61

```
Ala Met Leu Pro Ala Val Pro Ser Leu
```

<210> SEQ ID NO 62
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 62

Ala Trp Leu Pro Ala Val Pro Ser Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 63

Asn Phe Met Asn Leu Gly Ala Thr Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 64

Asn Met Met Asn Leu Gly Ala Thr Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 65

Asn Trp Met Asn Leu Gly Ala Thr Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 66

Arg Tyr Pro Ser Ser Gln Lys Lys Phe
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 67

Arg Tyr Pro Ser Ala Gln Lys Lys Phe
1               5

```
<210> SEQ ID NO 68
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (5)..(5)
<223> OTHER INFORMATION: Xaa = Abu

<400> SEQUENCE: 68

Arg Tyr Pro Ser Xaa Gln Lys Lys Phe
1               5
```

US 7,666,985 B2

HLA-A24-RESTRICTED CANCER ANTIGEN PEPTIDES

TECHNICAL FIELD

The present invention belongs to the field of cancer vaccine therapies. The invention relates to HLA-A24-restricted cancer antigen peptides, and more particularly, to HLA-A24-restricted cancer antigen peptides derived from WT1 which have an activity to induce CTLs in vivo, polynucleotides encoding said peptides, and cancer vaccines which comprise those substances, use of them as cancer vaccines, and methods for treatment and prevention of cancers based on them.

BACKGROUND ART

Cellular immunities, particularly cytotoxic T cells (referred to as CTLs hereinafter), play an important role in the elimination of cancer cells or virus-infected cells from a living body. CTLs recognize a complex formed between an antigen peptide derived from a cancer antigen protein on a cancer cell (cancer antigen peptide) and an MHC (Major Histocompatibility Complex) class I antigen (referred to as an HLA antigen in the case of human), and thereby attack and injure cancer cells.

Representative examples of cancer antigen proteins are listed in Table 1 described in *Immunity*, vol. 10: 281, 1999. Specific examples include melanosomal antigens such as a melanocytic tissue-specific protein, gp100 (*J. Exp. Med.*, 179:1005, 1994), MART-1 (*Proc. Natl. Acad. Sci. USA*, 91:3515, 1994), and tyrosinase (*J. Exp. Med.*, 178:489, 1993); as well as HER2-neu (*J. Exp. Med.*, 181:2109, 1995) and cancer markers such as CEA (*J. Natl. Cancer Inst.*, 87:982, 1995) and PSA (*J. Natl. Cancer Inst.*, 89:293, 1997) as cancer antigen proteins other than those from melanomas. Cancer antigen peptides are peptides consisting of about 8 to 11 amino acid residues, generated through the processing of cancer antigen proteins with intracellular proteases (*Cur. Opin, Immunol.*, 5:709, 1993; *Cur. Opin, Immunol.*, 5: 719, 1993; *Cell*, 82: 13, 1995; *Immunol. Rev.*, 146: 167, 1995). The cancer antigen peptides thus generated bind to MHC class I antigens (HLA antigens) to form complexes, and then the complexes are presented on cellular surfaces, and recognized by CTLs as described above. In development of medicaments for cancer immunotherapy (cancer vaccines) based on cancer cells disruption by CTLs, it therefore is very important to identify a cancer antigen peptide from the cancer antigen protein, which can effectively induce CTLs.

Lots of subtypes exist in MHC class I molecules, and the amino acid sequence of an antigen peptide that binds to the respective subtype obeys a certain rule (binding motif). Regarding the binding motif for HLA-A2, for example, the amino acid at position 2 is leucine, methionine, or isoleucine, and the amino acid at position 9 is valine, leucine, or isoleucine. Regarding the binding motif for HLA-A24, the amino acid at position 2 is tyrosine, phenylalanine, methionine, or tryptophan, and the amino acid at position 9 is phenylalanine, leucine, isoleucine, tryptophan, or methionine. Recently, any peptide sequence expected to be capable of binding to HLA antigens including the motifs as shown above may be searched on databases (for example, BIMAS software; http://bimas.dcrt.nih.gov/molbio/hla_bind/). Accordingly, in order to identify a cancer antigen peptide that can induce CTLs from the cancer antigen protein, peptide regions consisting of about 8 to 11 amino acid in length that match the binding motif or the peptide sequence expected for an intended HLA type are first identified from the amino acid sequence of the cancer antigen protein.

However, peptides that have been identified based on the binding motif or the expected peptide sequence are not necessarily immunogenic. Since an antigen peptide is generated through the intracellular processing of a cancer antigen protein, a peptide not having been generated through the processing cannot be an antigen peptide. Furthermore, since many cancer antigen proteins exist originally in a living body, CTLs may be tolerant to such cancer antigens even if a peptide having the binding motif or the expected peptide sequence is intracellularly generated as a cancer antigen peptide. Those show that, in order to identify a cancer antigen peptide having an activity to induce CTLs, a prediction merely based on the binding motif or the peptide sequence expected for an intended HLA type is insufficient, and an in vivo evaluation for immunogenicity (an activity to induce CTLs) should be important.

A Wilms cancer suppressor gene WT1 (WT1 gene) was isolated from chromosome 11p13 as one of the causative genes of Wilms cancers based on the analysis of the WAGR syndrome that was complicated by Wilms cancers, aniridia, urogenital anomaly, mental retardation, etc. (*Nature*, 343: 774, 1990). The genomic DNA of WT1 is about 50 Kb, and is composed of ten exons, of which cDNA is about 3 kb. The amino acid sequence deduced from the cDNA is as shown in SEQ ID NO: 1 (*Cell.*, 60:509, 1990). The WT1 gene has been suggested to promote the growth of leukemia cells from the facts that the WT1 gene is highly expressed in human leukemia, and that the leukemia cells are suppressed in their cellular growth by the treatment with WT1 antisense oligomers (Japanese Patent Publication (Kokai) No. 104627/1997). Then, the WT1 gene has been demonstrated to be a new cancer antigen protein of leukemia and solid cancers (*J. Immunol.*, 164: 1873-80, 2000, *J. Clin. Immunol.*, 20, 195-202, 2000) from the fact that the WT1 gene is also highly expressed in solid cancers such as gastric cancer, colon cancer, lung cancer, breast cancer, embryonal cancer, skin cancer, bladder cancer, prostate cancer, uterine cancer, cervical cancer, and ovarian cancer (Japanese Patent Publication (Kokai) No. 104627/1997, Japanese Patent Publication (Kokai) No. 35484/1999). Medicaments for cancer immunotherapy (cancer vaccines) can be preferably applied to as many as possible of cancer patients, and therefore it is important to identify cancer antigen peptides from WT1, which is highly expressed in many kinds of cancer, and to develop cancer vaccines based on those cancer antigen peptides. In this context, WO00/06602 and WO00/18795 describe naturally-occurring cancer antigen peptides composed of a portion of the WT1 protein.

In the course of development of cancer vaccines, evaluation of a vaccine for its in vivo efficacy cannot be conducted using pure-line mice commonly used as experimental animals, and requires an animal model for human expressing an HLA. Specifically, human antigen peptides usable as cancer vaccine induce specific immune responses when presented to an HLA, which is an MHC class 1 molecule specific for human. Non-human experimental animals lack such an HLA, and therefore are unavailable for in vivo evaluation of cancer vaccines directed to treatment of human. Accordingly, animal models for human expressing an HLA are essential in the evaluation of cancer vaccines for their efficacy as described above.

DISCLOSURE OF THE INVENTION

The present invention aims to provide cancer antigen peptides derived from WT1, which have an immunogenicity (an activity to induce CTLs) in vivo, and cancer vaccines which comprise those peptides, use of them as cancer vaccines, and methods for treatment and prevention of cancer based on them.

Recently, animal models for human expressing an HLA-A24 antigen which can be used to evaluate the in vivo efficacy had been prepared, and a patent application claiming the invention thereof was filed (WO 02/47474, the international filing date: Jun. 20, 2002, the applicant: Sumitomo Pharmaceutical Co., Ltd.).

The models have made it possible to evaluate the in vivo efficacy of HLA-A24-restricted cancer antigen proteins and cancer antigen peptides, as well as the gene thereof.

The present inventors used those animal models for human to evaluate natural peptides and altered peptides that are derived from WT1 and that are restricted to an HLA-A24. Namely, our evaluation of peptides having peptide sequences expected for an HLA-A24 antigen (binding motif) deduced from the WT1 sequence using BIMAS software (http://bimas.dcrt.nih.gov/molbio/hla_bind/) has revealed that, among the following natural peptides:

peptide A: Arg Met Phe Pro Asn Ala Pro Tyr Leu (SEQ ID NO: 8)
peptide B: Arg Val Pro Gly Val Ala Pro Thr Leu (SEQ ID NO: 7)
peptide C: Arg Trp Pro Ser Cys Gln Lys Lys Phe (SEQ ID NO: 9)
peptide D: Gln Tyr Arg Ile His Thr His Gly Val Phe (SEQ ID NO: 10) and
peptide E: Ala Tyr Pro Gly Cys Asn Lys Arg Tyr Phe (SEQ ID NO: 11), only peptide B (SEQ ID NO: 7) has an immunogenicity (an activity to induce CTLs) in vivo.

Further, the inventors prepared the following altered peptides:

peptide F: Arg Tyr Phe Pro Asn Ala Pro Tyr Leu (SEQ ID NO: 2)
peptide G: Arg Tyr Pro Gly Val Ala Pro Thr Leu (SEQ ID NO: 3) and
peptide H: Arg Tyr Pro Ser Cys Gln Lys Lys Phe (SEQ ID NO: 4), all of which have an alteration wherein the amino acid at position 2 of peptides A to C as described above is altered into tyrosine (Tyr), and evaluated their immunogenicity in a similar manner. As a result, the inventors found that the altered form: peptide G has a higher immunogenicity than the natural form: peptide B of origin thereof. Also, the inventors found that, although the natural forms: peptides A and C have no immunogenicity, the altered forms thereof: peptides F and H have a high immunogenicity (an activity to induce CTLs).

Furthermore, the inventors also evaluated in a similar manner the immunogenicity of the following natural peptides (peptides K and L) derived from human WT1 that were identified to have the peptide sequence expected for an HLA-A24 antigen in the search by BIMAS software, and the following altered peptides thereof wherein the amino acid at position 2 is altered into tyrosine (peptides I and J):

peptide K: Ala Leu Leu Pro Ala Val Pro Ser Leu (SEQ ID NO: 51)
peptide L: Asn Gln Met Asn Leu Gly Ala Thr Leu (SEQ ID NO: 52)
peptide I: Ala Tyr Leu Pro Ala Val Pro Ser Leu (SEQ ID NO: 5) and
peptide J: Asn Tyr Met Asn Leu Gly Ala Thr Leu (SEQ ID NO: 6). As a result, the inventors found that, although the natural forms: peptides K and L have no immunogenicity (an activity to induce CTLs), the altered forms thereof: peptides I and J have a high immunogenicity (an activity to induce CTLs) in vivo.

On the basis of those findings above, the inventors hold the conviction that the altered peptides as shown in SEQ ID NOs: 2 to 6, and the natural peptide as shown in SEQ ID NO: 7 with or without various modifications should be available as cancer vaccines. The present invention has been completed on the basis of the findings as described above.

Thus, the present invention relates to:

(I) A peptide which comprises any one of the amino acid sequences selected from a group consisting of:
Arg Tyr Phe Pro Asn Ala Pro Tyr Leu (SEQ ID NO: 2),
Arg Tyr Pro Gly Val Ala Pro Thr Leu (SEQ ID NO: 3),
Arg Tyr Pro Ser Cys Gln Lys Lys Phe (SEQ ID NO: 4),
Ala Tyr Leu Pro Ala Val Pro Ser Leu (SEQ ID NO: 5), and
Asn Tyr Met Asn Leu Gly Ala Thr Leu (SEQ ID NO: 6); or a peptide which consist of any one of the amino acid sequences selected from a group consisting of SEQ ID NOs: 2, 3, 4, 5, and 6; or A peptide which comprises an altered amino acid sequence wherein an alteration of an amino acid residue is comprised in any one of the amino acid sequences selected from a group consisting of SEQ ID NOs: 2, 3, 4, 5, and 6, and which has an activity to induce a CTL in an HLA-A24-restricted manner, except for a peptide comprising the amino acid of SEQ ID NO: 7; preferably, the peptide according to the present invention, which comprises an altered amino acid sequence wherein leucine at position 9 in any one of the amino acid sequences selected from a group consisting of SEQ ID NOs: 2, 3, 5, and 6 is substituted by phenylalanine, tryptophan, isoleucine, or methionine; the peptide according to the invention, which comprises an altered amino acid sequence wherein phenylalanine at position 9 in the amino acid sequence of SEQ ID NO: 4 is substituted by tryptophan, leucine, isoleucine, or methionine; or the peptide according to the invention, which comprises an altered amino acid sequence wherein cysteine at position 5 in the amino acid sequence of SEQ ID NO: 4 is substituted by alanine, serine, or α-aminobutyric acid (SEQ ID NO: 66, 67, or 68); or the peptide according to the invention which consists of an altered amino acid sequence wherein an alteration of an amino acid residue is comprised in any one of the amino acid sequences selected from a group consisting of SEQ ID NOs: 2, 3, 4, 5, and 6;

(II) A polynucleotide which encodes the peptide according to the invention, preferably a polynucleotide according to the invention which encodes any one of the amino acid sequences selected from the group consisting of SEQ ID NOs: 2 to 6, and 66 to 68; or an expression vector which contains the polynucleotide of according to the invention; or A transformed cell which comprises the expression vector according to the invention; or a process for preparing a peptide according to the invention, which comprises culturing the cell according to the invention in a condition operable for the expression of peptides;

(III) An antibody which specifically binds to a peptide according to the invention;

(IV) An antigen-presenting cell on which a complex between a cancer antigen peptide derived from the peptide according to the invention and an HLA-A24 antigen is presented, preferably, the antigen-presenting cell according to the invention, on which a complex between a cancer antigen peptide consisting of any one of the amino acid sequences selected from the group consisting of SEQ ID NOs: 2 to 6 and 66 to 68 and an HLA-A24 antigen is presented;

(V) A CTL which recognizes a complex between a cancer antigen peptide derived from the peptide according to the invention and an HLA-A24 antigen, preferably the CTL according to the invention, which recognizes a complex between a cancer antigen peptide consisting of any one of the amino acid sequences selected from the group consisting of SEQ ID NOs: 2 to 6 and 66 to 68 and an HLA-A24 antigen; and (VI) A pharmaceutical composition which comprises the peptide according to the invention, the polynucleotide according to the invention, the expression vector according to the invention, the transformed cell according to the invention, the antigen-presenting cell according to the invention, or the CTL according to the invention, together with a pharmaceutically acceptable carrier, specifically the cancer vaccine; as well as use of the peptide, the polynucleotide, the expression vector, the transformed cell, the antigen-presenting cell or the CTL according to the invention in the manufacture of a cancer vaccine, and a method for treatment or prevention of a cancer, which comprises administering a therapeutically or prophylactically effective amount of the peptide, the polynucleotide, the expression vector, the transformed cell, the antigen-presenting cell, or the CTL according to the invention, to a cancer patient in need who is positive for an HLA-A24, and positive for WT1.

Further, the invention also provides:

(VII) a pharmaceutical composition which comprises any one of the substances selected from the group consisting of:
a) a peptide which comprises the sequence of Arg Val Pro Gly Val Ala Pro Thr Leu (SEQ ID NO: 7),
b) a polynucleotide which encodes the peptide as shown above a),
c) an expression vector which comprises the polynucleotide as shown above b),
d) a cell which comprises the expression vector as shown above c),
e) an antigen-presenting cell on which a complex between a cancer antigen peptide derived from the peptide as shown above a) and an HLA-A24 antigen is presented, and
f) a CTL which recognizes a complex between a cancer antigen peptide derived from the peptide as shown above a) and an HLA-A24 antigen, together with a pharmaceutically acceptable carrier; specifically, the cancer vaccine; as well as use of the peptide, the polynucleotide, the expression vector, the transformed cell, the antigen-presenting cell or the CTL as described above in the manufacture of a cancer vaccine, and a method for treatment or prevention of a cancer, which comprises administering a therapeutically or prophylactically effective amount of the peptide, the polynucleotide, the expression vector, the transformed cell, the antigen-presenting cell, or the CTL as described above, to a cancer patient in need who is positive for an HLA-A24, and positive for WT1.

BRIEF DESCRIPTION OF DRAWINGS

FIG. 3 is an alignment between the sequence from positions 1 to 1300 of the HLA-A2402/K$^b$ genomic sequence described in SEQ ID NO: 33 and the sequence from positions 1 to 407 of the HLA-A2402/K$^b$ cDNA sequence described in SEQ ID NO: 34.

FIG. 4 is an alignment between the sequence from positions 1301 to 2600 of the HLA-A2402/K$^b$ genomic sequence described in SEQ ID NO: 33 and the sequence from positions 408 to 1015 of the HLA-A2402/K$^b$ cDNA sequence described in SEQ ID NO: 34.

FIG. 5 is an alignment between the sequence from positions 2601 to 3857 of the HLA-A2402/K$^b$ genomic sequence described in SEQ ID NO: 33 and the sequence from positions 1016 to 1119 of the HLA-A2402/K$^b$ cDNA sequence described in SEQ ID NO: 34.

FIG. 24 is a graph showing that CTLs were induced when peripheral blood mononuclear cells from healthy donors positive for HLA-A2402 were stimulated in vitro with an antigen peptide (peptide B, $WT1_{302-310}$) derived from human WT1, or the altered peptide thereof (peptide G) wherein the amino acid residue at position 2 in peptide B is altered into tyrosine. In the figure, the vertical axis shows the cytotoxic activity, and the horizontal axis shows the ratio of effector cells (E) and target cells (T), E/T. The solid circle and the solid triangle show the cytotoxic activities of the effector cells stimulated with the multi-altered peptide on RERF-LC-AI cells and LK87 cells, respectively. The open circle, the open triangle and the open square show the cytotoxic activities of the effector cells stimulated with the natural peptide on RERF-LC-AI cells, LK87 cells, and 11-18 cells, respectively.

Figure 1:
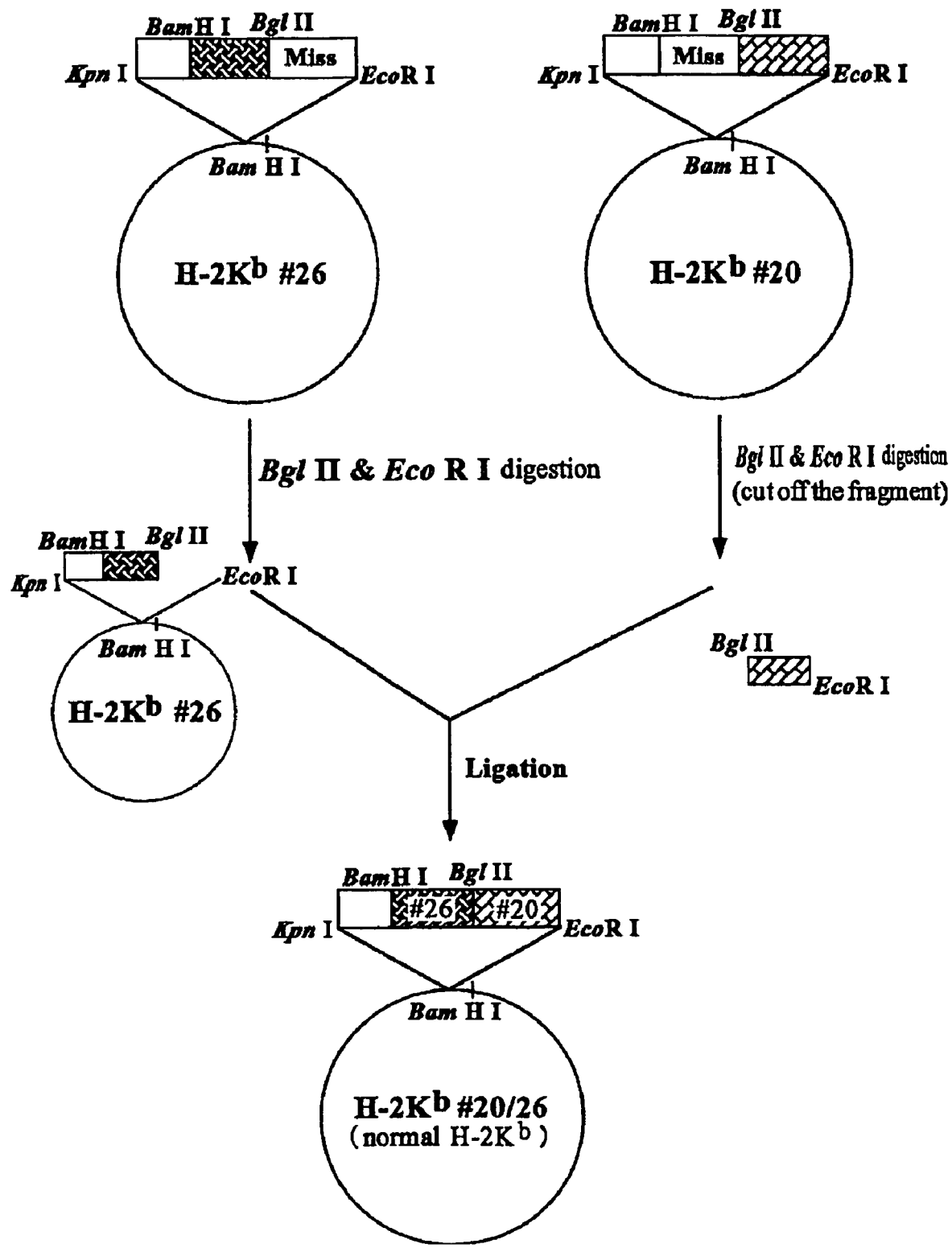
FIG. 1 is a schematic diagram showing the process for preparing an H-2K$^b$ genomic DNA used for constructing the chimera gene (HLA-A2402/K$^b$ gene) of the present invention.

BEST MODE FOR CARRYING OUT THE INVENTION (I) Peptides According to the Present Invention Peptides of the present invention are derived from human WT1 (*Cell.*, 60:509, 1990, NCBI database Accession No. XP_034418, SEQ ID NO: 1), and have an activity to induce CTLs (an immunogenicity) in vivo in an HLA-A24-restricted manner.

The peptides of the invention have a property to be presented on an antigen-presenting cell to induce CTLs in vivo in an HLA-A24 antigen-restriced manner. Such a property may be examined using animal models for an HLA-A24 described in details in References hereinafter.

The peptides of the invention that comprise any one of the amino acid sequences selected from a group consisting of SEQ ID NO: 2, 3, 4, 5, and 6 are not limited in any respect as long as the peptide has a property that a cancer antigen peptide derived from the peptide is presented on an antigen-presenting cell to induce CTLs. Typical length of the amino acid residues of the peptide is usually 9 to 100, preferably 9 to 50, more preferably 9 to 30, still more preferably 9 to 20, and even more preferably 9 to 11. In this context, a cancer antigen peptide is defined as a peptide that causes a CTL-inducing activity when presented on an antigen-presenting cell.

The peptides of the invention may be prepared according to a method usually used in peptide chemistry. Examples of such preparations are those as described in the literatures including "Peptide Synthesis", Interscience, New York, 1966; "The Proteins", vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

The peptides of the invention may be also prepared on the basis of the sequence information of polynucleotide encoding the peptide of the invention according to conventional DNA synthesis and genetic engineering procedures. Procedures such as the DNA synthesis, constructions of various plasmids, transfection of the same into host cells, cultivation of the transformants, and recovery of the proteins from the culture may be carried out according to methods well-known by those skilled in the art, methods described in the literatures (Molecular Cloning, T. Maniatis et al., CSH Laboratory (1983), DNA Cloning, D M. Glover, IRL PRESS (1985)), or the method described (II) hereinafter.

Specific illustrations of the peptides according to the invention are provided below.

(1) Peptides which Comprise any One of the Amino Acid Sequences Selected from a Group Consisting of SEQ ID NO: 2 to 6

As described above, the present invention is based on the new finding that the altered peptides derived from WT1 as shown in SEQ ID NO: 2 to 6 have an activity to induce CTLs in vivo. The fact that the new peptides as shown in SEQ ID NO: 2 to 6 surely have an activity to induce CTLs in vivo has not been known previously. Peptides comprising any one of those altered peptides are useful as an active ingredient comprised in a composition for inducing CTLs or a cancer vaccine as used in immunotherapy for cancer.

Specifically, the peptide of the invention comprises any one of the followings:

Arg Tyr Phe Pro Asn Ala Pro Tyr Leu, (SEQ ID NO: 2)

Arg Tyr Pro Gly Val Ala Pro Thr Leu, (SEQ ID NO: 3)

Arg Tyr Pro Ser Cys Gln Lys Lys Phe, (SEQ ID NO: 4)

Ala Tyr Leu Pro Ala Val Pro Ser Leu, (SEQ ID NO: 5) and

Asn Tyr Met Asn Leu Gly Ala Thr Leu. (SEQ ID NO: 6)

Among them, a peptide comprising the sequence of Arg Tyr Pro Ser Cys Gln Lys Lys Phe (SEQ ID NO: 4) and a peptide comprising the sequence of Ala Tyr Leu Pro Ala Val Pro Ser Leu (SEQ ID NO: 5) are preferred.

Examples of more specific peptides according to the invention include the peptides as shown in (1-1) to (1-4) below.

(1-1) Peptides which Consist of any One of the Amino Acid Sequences Selected from a Group Consisting of SEQ ID NOS: 2 to 6

Specific examples of peptides which consist of any one of the amino acid sequences of SEQ ID NO: 2 to 6 include the following cancer antigen peptides:

cancer antigen peptide consisting of the sequence of Arg Tyr Phe Pro Asn Ala Pro Tyr Leu (SEQ ID NO: 2), cancer antigen peptide consisting of the sequence of Arg Tyr Pro Gly Val Ala Pro Thr Leu (SEQ ID NO: 3), cancer antigen peptide consisting of the sequence of Arg Tyr Pro Ser Cys Gln Lys Lys Phe (SEQ ID NO: 4), cancer antigen peptide consisting of the sequence of Ala Tyr Leu Pro Ala Val Pro Ser Leu (SEQ ID NO: 5), and cancer antigen peptide consisting of the sequence of Asn Tyr Met Asn Leu Gly Ala Thr Leu (SEQ ID NO: 6).

Among them, a cancer antigen peptide consisting of the sequence of Arg Tyr Pro Ser Cys Gln Lys Lys Phe (SEQ ID NO: 4) and a cancer antigen peptide consisting of the sequence of Ala Tyr Leu Pro Ala Val Pro Ser Leu (SEQ ID NO: 5) are preferred. Those peptides may be prepared according to common methods for peptide synthesis as described above. The activity of those peptides to induce CTLs in vivo may be determined in animal models for human described in References hereinafter.

(1-2) Peptides which Comprise any One of the Amino Acid Sequences of SEQ ID NOs: 2 to 6, and which Contain the Motif Structure It has been known that lots of subtypes exist in HLA molecules, and that the amino acid sequences of antigen peptides that bind to each subtype obey a certain rule (binding motif). It has been also known that, regarding the binding motif for HLA-A24, the amino acid at position 2 is tyrosine (Tyr), phenylalanine (Phe), methionine (Met), or tryptophan (Trp), and the amino acid at C-terminus is phenylalanine (Phe), leucine (Leu), isoleucine (Ile), tryptophan (Trp), or methionine (Met) in the peptides consisting of 8 to 11 amino acid residues. (*J. Immunol.*, 152, p 3913, 1994, *Immunogenetics*, 41, p 178, 1995, *J. Immunol.*, 155, p 4307, 1994).

Based on the rule, examples of the peptides according to the invention also include peptides consisting of 10 amino acid residues wherein Phe, Leu, Ile, Trp, or Met is added to the C-terminus of any one of the cancer antigen peptides consisting of 9 amino acid residues of:
Arg Tyr Phe Pro Asn Ala Pro Tyr Leu (SEQ ID NO: 2),
Arg Tyr Pro Gly Val Ala Pro Thr Leu (SEQ ID NO: 3),
Arg Tyr Pro Ser Cys Gln Lys Lys Phe (SEQ ID NO: 4),
Ala Tyr Leu Pro Ala Val Pro Ser Leu (SEQ ID NO: 5), or
Asn Tyr Met Asn Leu Gly Ala Thr Leu (SEQ ID NO: 6), as well as peptides consisting of 11 amino acid residues wherein Phe, Leu, Ile, Trp, or Met is further added to the C-terminus of any one of said peptides consisting of 10 amino acid residues, all of which have an activity to induce CTLs in vivo. Those peptides may be prepared according to common methods for peptide synthesis as described above. The activity of those peptides to induce CTLs in vivo may be determined in animal models for human described in References hereinafter.

(1-3) Epitope Peptides which Comprise any One of the Amino Acid Sequences of SEQ ID NOs: 2 to 6

Recently, it has been demonstrated that a peptide wherein many CTL epitopes (antigen peptides) are linked each other (an epitope peptide) has an activity to induce effectively CTLs in vivo. For example, *Journal of Immunology* 1998, 161: 3186-3194 describes that the about 30-mer peptide wherein HLA-A2, -A3, -A11, B53-restricted CTL epitopes derived from a cancer antigen protein, PSA, are linked each other induced CTLs specific for the relevant CTL epitope in vivo.

Also, it has been demonstrated that a peptide wherein a CTL epitope and a helper epitope are linked each other (epitope peptides) effectively induced CTLs. Helper epitope refers to as a peptide that activates CD4-positive T cells (*Immunity.*, 1:751, 1994), and is known to include HBVc128-140 derived from hepatitis B virus and TT947-967 derived from tetanus toxin. CD4-positive T cells activated by the helper epitope are believed to be important in immune responses to destroy cancers because they exert the actions such as the induction of CTL differentiation and the maintenance of CTLs, and the activation of effectors including a macrophage. As examples of such peptides wherein a helper epitope and a CTL epitope are linked each other, for example, *Journal of Immunology* 1999, 162: 3915-3925 describes that a DNA encoding the peptide linked with the six HLA-A2-restricted antigen peptides, the three HLA-A11-restricted antigen peptides derived from HBV, and a helper epitope (minigene) has effectively induced CTLs in response to the relevant epitopes in vivo. In addition, the peptide wherein the CTL epitope (cancer antigen peptide consisting of positions 280 to 288 of a melanoma antigen, gp100) and the helper epitope (T helper epitope derived from tetanus toxin) are linked each other has been tested in clinical trial (*Clinical Cancer Res.*, 2001, 7: 3012-3024).

Based on these findings, peptides wherein the cancer antigen peptides or the peptides as shown in (1-1) or (1-2) above are linked with various epitopes (epitope peptide), which have an activity to induce CTLs in vivo, are also exemplified as the peptides according to the invention.

In case that an epitope to be linked with the cancer antigen peptide of the invention is a CTL epitope, usable CLT epitopes include those derived from WT1 which are restricted for HLA-A1, -A0201, -A0204, -A0205, -A0206, -A0207, -A11, -A24, -A31, -A6801, -B7, -B8, -B2705, -B37, -Cw0401, -Cw0602, or the like. Two or more epitopes may be linked, and one CTL epitope may be 8 to 14 amino acid residues in length on the basis of the analysis of antigen peptides bound to various HLA molecules (*Immunogenetics*, 41:178, 1995).

In case that an epitope to be linked with the cancer antigen peptide of the invention is a helper epitope, HBVc 128-140 derived from hepatitis B virus and TT947-967 derived from tetanus toxin as described above may be exemplified. The length of the helper epitope may be about 13 to about 30, preferably about 13 to about 17 amino acid residues.

Specific examples of the epitope peptides according to the invention include peptides wherein the one or more amino acid sequences of any one of SEQ ID NOs: 2 to 6 is linked with a helper epitope. More specifically, a peptide wherein the one or more amino acid sequences of any one of SEQ ID NOs: 2 to 6 are linked with a helper epitope derived from tetanus toxin (for example, Phe Asn Asn Phe Thr Val Ser Phe Trp Leu Arg Val Pro Lys Val Ser Ala Ser His Leu Glu; SEQ ID NO: 32), and a peptide wherein the one or more amino acid sequences of any one of SEQ ID NOs: 2 to 6 are linked with the sequence of Ala Gln Tyr Ile Lys Ala Asn Ser Lys Phe Ile Gly Ile Thr Glu Leu (SEQ ID NO: 50, *Clinical Cancer Res.*, 2001, 7:3012-3024) are exemplified.

Those peptides (epitope peptides) wherein various epitopes are linked each other may be prepared according to common methods for peptide synthesis as described above. The peptides may be also prepared on the basis of the sequence information of polynucleotide encoding the peptide wherein various epitopes are linked each other according to conventional DNA synthesis and genetic engineering procedures. Namely, the peptides may be prepared by inserting the polynucleotide into a well-known expression vector, transforming a host cell with the recombinant expression vector, culturing the transformants, and recovering the epitope peptide wherein various intended epitopes are linked each other from the culture. Those procedures may be carried out according to methods described in the literatures (Molecular Cloning, T. Maniatis et al., CSH Laboratory (1983), DNA Cloning, D M. Glover, IRL PRESS (1985)), or the method described in (II) hereinafter.

The activity of the epitope peptides wherein various epitopes are linked each other thus prepared to induce CTLs in vivo may be determined in animal models for human described in References hereinafter.

(1-4) Peptides which Comprise any One of the Amino Acid Sequences of SEQ ID NOs: 2 to 6 wherein the Amino Group of the N-terminal Amino Acid or the Carboxyl Group of the C-terminal Amino Acid is Modified The amino group of the N-terminal amino acid or the carboxyl group of the C-terminal amino acid in the peptides of the invention as described in (1-1) to (1-3) above may be modified.

In this context, modifying groups of the amino group of the N-terminal amino acid include an alkyl group having 1 to 6 carbon atoms, a phenyl group, a cycloalkyl group, an acyl group, and the like, of which the 1 to 3 may be selected. Examples of the acyl group include an alkanoyl group having 1 to 6 carbon atoms, an alkanoyl group having 1 to 6 carbon atoms substituted with a phenyl group, a carbonyl group substituted with a cycloalkyl group having 5 to 7 carbon atoms, a alkylsulfonyl group having 1 to 6 carbon atoms, a phenylsulfonyl group, an alkoxycarbonyl group having 2 to 6 carbon atoms, an alkoxycarbonyl group substituted with a phenyl group, a carbonyl group substituted with a cycloalkoxy having 5 to 7 carbon atoms, a phenoxycarbonyl group, and the like.

Peptides wherein the carboxyl group of the C-terminal amino acid is modified include esters and amides. Specific esters include a C1-C6 alkyl ester, a C0-C6 alkyl ester substituted with a phenyl group, a C5-C7 cycloalkyl ester, and the like, whereas specific amides include an amide, an amide substituted with one or two C1-C6 alkyl groups, an amide substituted with one or two C0-C6 alkyl groups substituted with a phenyl group, an amide that forms a 5 to 7-numbered azacycloalkane that contains the nitrogen atom of the amide, and the like.

(2) Peptides which Comprise an Altered Amino Acid Sequence wherein an Alteration of an Amino Acid Residue is Comprised in any One of the Amino Acid Sequences Selected from a Group Consisting of SEQ ID NOs: 2 to 6 (Multi-altered Peptides)

The present invention is based on the new finding that the altered peptides derived from WT1 as shown in SEQ ID NO: 2 to 6 have an activity to induce CTLs in vivo, as described above. An additional alteration of the amino acids of those peptides having an activity to induce CTLs in vivo may lead to a multi-altered peptide having an equivalent or more potent activity to induce CTLs. Based on this concept, the present invention provides peptides which comprises an altered amino acid sequence relative to the amino acid sequence of any one of the peptides of SEQ ID NOs: 2 to 6 (those peptides may be referred to as multi-altered peptides hereinafter).

Specifically, the invention provides a peptide which comprises an altered amino acid sequence wherein an alteration of an amino acid residue is comprised in any one of the amino acid sequences selected from a group consisting of SEQ ID NOs: 2, 3, 4, 5, and 6, and which has an activity to induce CTLs, provided that a peptide comprising the amino acid of SEQ ID NO: 7 is excluded from the scope of the peptides according to the present invention.

As used herein, "alteration" of an amino acid residue means substitution, deletion and/or addition of one or several amino acid residue(s), with the substitution of an amino acid residue being preferred. For alterations involving the substitution of an amino acid residue, the number and the position of an amino acid residue to be substituted may be determined arbitrarily as long as the activity to induce CTLs in vivo is retained. Examples of such peptides comprising the altered amino acid sequence include those shown below.

As described above, it has been known that, regarding the binding motif for HLA-A24, the amino acid at position 2 is tyrosine (Tyr), phenylalanine (Phe), methionine (Met), or tryptophan (Trp), and the amino acid at C-terminus is phenylalanine (Phe), leucine (Leu), isoleucine (Ile), tryptophan (Trp), or methionine (Met) in the peptides consisting of 8 to 11 amino acid residues. (*J. Immunol.*, 152, p 3913, 1994, *Immunogenetics*, 41, p 178, 1995, *J. Immunol.*, 155, p 4307, 1994). Based on the rule, multi-altered peptides according to the present invention may comprise substitution(s) of amino acid residue(s) at positions 2 and/or 9 in the amino acid sequence of any one of SEQ ID NOs: 2 to 6 with an amino acid residue available for the motif as shown above.

Specific examples of the multi-altered peptides comprising an alteration of an amino acid residue at position 2 include a peptide which comprises any one of the following amino acid sequences, and which has an activity to induce CTLs in vivo:

```
                                          (SEQ ID NO: 12)
Arg Tyr Phe Pro Asn Ala Pro Tyr Phe, (SEQ ID NO: 13)
Arg Tyr Phe Pro Asn Ala Pro Tyr Trp, (SEQ ID NO: 14)
Arg Tyr Phe Pro Asn Ala Pro Tyr Ile, (SEQ ID NO: 15)
Arg Tyr Phe Pro Asn Ala Pro Tyr Met, (SEQ ID NO: 16)
Arg Tyr Pro Gly Val Ala Pro Thr Phe, (SEQ ID NO: 17)
Arg Tyr Pro Gly Val Ala Pro Thr Trp, (SEQ ID NO: 53)
Arg Phe Phe Pro Asn Ala Pro Tyr Leu, (SEQ ID NO: 54)
Arg Trp Phe Pro Asn Ala Pro Tyr Leu, (SEQ ID NO: 55)
Arg Phe Pro Gly Val Ala Pro Thr Leu, (SEQ ID NO: 56)
Arg Met Pro Gly Val Ala Pro Thr Leu, (SEQ ID NO: 57)
Arg Trp Pro Gly Val Ala Pro Thr Leu, (SEQ ID NO: 58)
Arg Phe Pro Ser Cys Gln Lys Lys Phe, (SEQ ID NO: 59)
Arg Met Pro Ser Cys Gln Lys Lys Phe, (SEQ ID NO: 60)
Ala Phe Leu Pro Ala Val Pro Ser Leu, (SEQ ID NO: 61)
Ala Met Leu Pro Ala Val Pro Ser Leu, (SEQ ID NO: 62)
Ala Trp Leu Pro Ala Val Pro Ser Leu, (SEQ ID NO: 63)
Asn Phe Met Asn Leu Gly Ala Thr Leu, (SEQ ID NO: 64)
Asn Met Met Asn Leu Gly Ala Thr Leu,
and
                                          (SEQ ID NO: 65)
Asn Trp Met Asn Leu Gly Ala Thr Leu.
```

Those peptides include a peptide which consists of any one of the amino acid sequences of SEQ ID NOs: 53 to 65 as shown above, and which has an activity to induce CTLs in vivo.

All of the peptides of the present invention according to SEQ ID NOs: 2 to 6 have been accomplished by altering the amino acid residue at position 2 in the natural peptides derived from human WT1 to provide altered peptides that have an activity to induce CTLs effectively. In this context, the amino acid residue at position 2 in the multi-altered peptides of the present invention is preferably tyrosine. On the other hand, an amino acid residue at the C-terminus in the multi-altered peptides may be altered into an amino acid residue available for the motif as shown above.

Specific examples of the multi-altered peptides according to the present embodiment include a peptide which comprises any one of the following amino acid sequences, and which has an activity to induce CTLs in vivo:

-continued

Arg Tyr Pro Gly Val Ala Pro Thr Ile, (SEQ ID NO: 18)

Arg Tyr Pro Gly Val Ala Pro Thr Met, (SEQ ID NO: 19)

Arg Tyr Pro Ser Cys Gln Lys Lys Trp, (SEQ ID NO: 20)

Arg Tyr Pro Ser Cys Gln Lys Lys Leu, (SEQ ID NO: 21)

Arg Tyr Pro Ser Cys Gln Lys Lys Ile, (SEQ ID NO: 22)

Arg Tyr Pro Ser Cys Gln Lys Lys Met, (SEQ ID NO: 23)

Ala Tyr Leu Pro Ala Val Pro Ser Phe, (SEQ ID NO: 24)

Ala Tyr Leu Pro Ala Val Pro Ser Trp, (SEQ ID NO: 25)

Ala Tyr Leu Pro Ala Val Pro Ser Ile, (SEQ ID NO: 26)

Ala Tyr Leu Pro Ala Val Pro Ser Met, (SEQ ID NO: 27)

Asn Tyr Met Asn Leu Gly Ala Thr Phe, (SEQ ID NO: 28)

Asn Tyr Met Asn Leu Gly Ala Thr Trp, (SEQ ID NO: 29)

Asn Tyr Met Asn Leu Gly Ala Thr Ile, (SEQ ID NO: 30)
and

Asn Tyr Met Asn Leu Gly Ala Thr Met. (SEQ ID NO: 31)

Those peptides include a peptide which consists of any one of the amino acid sequences of SEQ ID NOs: 12 to 31 as shown above, and which has an activity to induce CTLs in vivo.

Additional examples of the invention include a cancer antigen peptide that comprises both an alteration of an amino acid residue at position 2 in the multi-altered peptides comprising an alteration of an amino acid residue at position 2, and an alteration of an amino acid residue at the C-terminus as described above.

The amino acid sequence of SEQ ID NO: 4 contains a cysteine residue, which can be oxidized in a solution to form a disulfide bond. To avoid this, it is possible to substitute the cysteine reside by another amino acid residue such as an alanine residue, serine residue, or the like, or cl-aminobutyric acid that is similar to the cysteine residue in chemical structure to provide a multi-altered peptide.

Specific examples of the multi-altered peptides according to the present embodiment include a peptide which comprises any one of the following amino acid sequences, and which has an activity to induce CTLs in vivo:

Arg Tyr Pro Ser Ser Gln Lys Lys Phe, (SEQ ID NO: 66)

Arg Tyr Pro Ser Ala Gln Lys Lys Phe, (SEQ ID NO: 67)
and

Arg Tyr Pro Ser Abu Gln Lys Lys Phe, (SEQ ID NO: 68)

wherein Abu is α-aminobutyric acid.

The peptides include a cancer antigen peptide which consists of any one of the amino acid sequences of SEQ ID NOs: 66 to 68 as shown above, and which has an activity to induce CTLs in vivo.

Those peptides may be prepared according to common methods for peptide synthesis as described above. The activity of those peptides to induce CTLs in vivo may be determined in animal models for human described in References hereinafter.

The multi-altered peptides of the invention as described above also may be modified by retaining the motif structure as shown in (1-2) above, linking with many epitopes as shown in (1-3) above, or modifying the amino or carboxyl group as shown in (1-4) above.

The peptides of the invention are useful, for example, as an active ingredient comprised in a composition for inducing CTLs or a cancer vaccine, or in the preparation of antigen-presenting cells described hereinafter.

(II) Polynucleotides, Expression Vectors, and Transformants of the Present Invention The invention also provides polynucleotides encoding the peptides of the invention described above. The polynucleotides encoding the peptides of the invention may be in a form of either DNA or RNA. Those polynucleotides may be readily prepared on the basis of the information on amino acid sequences of the peptides of the invention, and on DNAs encoding the same. Specifically, they may be prepared according to common methods for DNA synthesis, or PCR amplification.

Examples of the polynucleotides of the invention include:

a polynucleotide that encodes a peptide comprising the sequence of Arg Tyr Phe Pro Asn Ala Pro Tyr Leu (SEQ ID NO: 2), a polynucleotide that encodes a peptide comprising the sequence of Arg Tyr Pro Gly Val Ala Pro Thr Leu (SEQ ID NO: 3), a polynucleotide that encodes a peptide comprising the sequence of Arg Tyr Pro Ser Cys Gln Lys Lys Phe (SEQ ID NO: 4), a polynucleotide that encodes a peptide comprising the sequence of Ala Tyr Leu Pro Ala Val Pro Ser Leu (SEQ ID NO: 5), a polynucleotide that encodes a peptide comprising the sequence of Asn Tyr Met Asn Leu Gly Ala Thr Leu (SEQ ID NO: 6), a polynucleotide that encodes a peptide comprising the sequence of Arg Tyr Pro Ser Ser Gln Lys Lys Phe (SEQ ID NO: 66), a polynucleotide that encodes a peptide comprising the sequence of Arg Tyr Pro Ser Ala Gln Lys Lys Phe (SEQ ID NO: 67), a polynucleotide that encodes a peptide comprising the sequence of Arg Tyr Pro Ser Abu Gln Lys Lys Phe (SEQ ID NO: 68) wherein Abu is α-aminobutyric acid.

Specific examples of polynucleotides include a polynucleotide that encodes an epitope peptide comprising the amino acid sequence of any one of SEQ ID NOs: 2 to 6, and 66 to 68 as described in (1-3) above. More specifically, polynucleotides that encode a peptide wherein the one or more amino acid sequences of any one of SEQ ID NOs: 2 to 6, and 66 to 68 are linked with a helper epitope, including a polynucleotide that encodes a peptide wherein the one or more amino acid sequences of any one of SEQ ID NOs: 2 to 6, and 66 to 68 are linked with a helper epitope derived from tetanus toxin (for example, Phe Asn Asn Phe Thr Val Ser Phe Trp Leu Arg Val Pro Lys Val Ser Ala Ser His Leu Glu; SEQ ID NO: 32), and a peptide wherein the one or more amino acid sequences of any one of SEQ ID NOs: 2 to 6, and 66 to 68 are linked with the sequence of Ala Gln Tyr Ile Lys Ala Asn Ser Lys Phe Ile Gly Ile Thr Glu Leu (SEQ ID NO: 50, Clinical Cancer Res., 2001, 7:3012-3024) are exemplified.

The polynucleotides thus prepared of the invention may be inserted into an expression vector to prepare recombinant expression vectors for expression of the peptides of the invention.

Expression vectors as used herein may be selected as appropriate depending on the host and the purpose in usage, and include a plasmid, a phage vector, and a virus vector.

Examples of vectors as used for *Escherichia coli* hosts include plasmid vectors such as pUC118, pUC119, pBR322, and pCR3, and phage vectors such as λZAPII, and λgt11. Examples of vectors as used for yeast hosts include pYES2, and pYEUra3. Examples of vectors as used for insect cell hosts include pAcSGHisNT-A. Examples of vectors as used for animal cell hosts include plasmid vectors such as pKCR, pCDM8, pGL2, pcDNA3.1, pRc/RSV, and pRc/CMV, and virus vectors such as a retrovirus vector, an adenovirus vector, and an adeno-associated virus vector.

Those vectors may comprise a factor such as a promoter inducible for expression, a gene encoding a signal sequence, a selection marker gene, a terminator, or the like, if necessary. Also, the vectors may comprise an added sequence for thioredoxin, His-tag, or GST (glutathione S-transferase) for easy isolation and purification, which provides a fusion protein. In this case, a vector for expression of a GST-fused protein that comprises a promoter (lac, tac, trc, trp, CMV, SV40 early promoter, or the like) suitably operated in a host cell (i.e., pGEX4T), a vector that comprises a tag-sequence such as Myc, His (i.e., pcDNA3.1/Myc-His), and a vector that expresses a fusion protein comprising thioredoxin or His-tag (pET32a) may be used.

The activity of the polynucleotides or the expression vectors comprising the same to induce CTLs in vivo may be determined in animal models for human described in References hereinafter.

The polynucleotides or the expression vectors comprising the same of the invention are useful, for example, in the preparation of the peptides of the invention, in gene therapy as described hereinafter, or in the preparation of antigen-presenting cells as described hereinafter.

The expression vectors thus prepared of the invention may be transformed into hosts to prepare transformants that comprise the expression vectors.

Hosts as used herein include *Escherichia coli*, a yeast, an insect cell, and an animal cell. *Escherichia coli* includes *E. coli* K-12 lines such as HB101 strain, C600 strain, JM109 strain, DH5α strain, and AD494(DE3) strain. Yeasts include *Saccharomyces cerevisiae*. Animal cells include L929 cell, BALB/c3T3 cell, C127 cell, CHO cell, COS cell, Vero cell, and Hela cell. Insect cells include sf9.

Common methods for transformation suitable for respective host cells may be used to transform the host cells with an expression vector. Specific methods include calcium phosphate method, DEAE-dextran method, electroporation, and a method wherein a lipid for gene transfer is used (Lipofectamine, Lipofectin; Gibco-BRL). After the transformation, the transformants may be incubated in a conventional medium containing a selection marker to select transformants wherein the expression vector as described above has been transformed into a host cell.

The transformants thus prepared may be incubated in an appropriate condition to prepare the peptides of the invention. The polypeptide may be further isolated and purified according to common procedures for biochemical purifications. Examples of procedures for the purification include salt precipitation, ion-exchange chromatography, adsorption chromatography, affinity chromatography, and gel filtration chromatography. When a polypeptide of the invention is expressed as a fusion protein comprising thioredoxin, His-tag, GST, or the like, the polypeptide may be isolated and purified by a purification method based on a property of such fusion protein or tag.

(III) Antibodies of the Present Invention

The present invention provides antibodies which specifically bind to a peptide according to the invention. The antibodies of the invention are not limited to a specific antibody, and may be a polyclonal antibody or a monoclonal antibody directed to a peptide of the invention as an immune antigen.

As mentioned above, the antibodies of the invention are not limited to a specific antibody as long as they specifically bind to the peptide of the invention, and specific examples include an antibody that specifically binds to a cancer antigen peptide consisting of any one of the amino acid sequences selected from SEQ ID NOs: 2 to 6, and 66 to 68.

Preparations for antibodies have been well known, and the antibodies of the invention may be prepared according to common methods well-known in the art (Current protocols in Molecular Biology edit. Ausubel et al. (1987) Publish. John Wiley and Sons. Section 11.12 to 11.13, Antibodies; A Laboratory Manual, Lane, H, D. et al. ed., Cold Spring Harber Laboratory Press Publisher, New York 1989).

Specifically, the antibodies may be prepared using the peptides of the invention (for example, a cancer antigen peptide consisting of any one of the amino acid sequences selected from SEQ ID NOs: 2 to 6, and 66 to 68) as an immunogen to immunize a non-human animal such as a rabbit, followed by obtaining the antibodies from the serum of the immunized animal in a conventional manner. On the other hand, monoclonal antibodies may be prepared by immunizing a non-human animal such as a mouse with a peptide of the invention (for example, a cancer antigen peptide consisting of any one of the amino acid sequences selected from SEQ ID NOs: 2 to 6, and 66 to 68), and preparing hybridoma from the splenocytes obtained and myeloma cells by cell fusion, followed by obtaining the antibodies from the hybridoma (Current protocols in Molecular Biology edit. Ausubel et al. (1987) Publish. John Wiley and Sons. Section 11.4 to 11.11).

The antibodies directed to the peptides of the invention may be prepared in a manner that the immunological reaction is enhanced using diverse adjuvants suitable for the host. Examples of the adjuvants include Freund's adjuvant, mineral gels such as aluminium hydroxide, surfactants such as lysolecithin and Pluronic polyol, polyanions, peptides, oil emulsions, Keyhole limpet Hemocyanin, dinitrophenol, and human adjuvants such as BCG (*Bacille Calmette Guerin*) and *Corynebactenum-parum*.

As described above, the antibodies that recognize the peptide, as well as the antibodies that neutralize the activity of the peptide may be readily prepared by immunizing appropriately an animal with the peptides of the invention in a conventional manner. Such antibodies may be used in affinity chromatography, immunological diagnosis, and the like. Immunological diagnosis may be selected as appropriate from immunoblotting, radioimmunoassay (RIA), enzyme-linked immunosorbent assay (ELISA), a fluorescent or luminescent assay, and the like. The immunological diagnosis is useful to diagnose cancers wherein the WT1 gene is expressed, such as gastric cancer, colon cancer, lung cancer, breast cancer, embryonal cancer, skin cancer, bladder cancer, prostate cancer, uterine cancer, cervical cancer, and ovarian cancer.

(IV) Antigen-presenting Cells of the Present Invention

The invention provides antigen-presenting cells on which a complex between a cancer antigen peptide derived from the peptide according to the invention and an HLA-A24 antigen is presented.

Examples described hereinafter demonstrate that the administration of the peptides of the invention induces CTLs, showing that antigen-presenting cells on which a complex between a cancer antigen peptide derived from the peptide according to the invention and an HLA-A24 antigen is presented, exist in peripheral blood mononuclear cells, and then CTLs that specifically injure cancer cells on which such a complex is presented are induced. Those antigen-presenting cells on which a complex between a cancer antigen peptide derived from the peptide according to the invention and an HLA-A24 antigen is presented, are useful in cell therapy (DC therapy) as described hereinafter.

Antigen-presenting cells of the present invention are not limited to a specific cell as long as they presents on their surfaces a complex between a cancer antigen peptide derived from the peptide according to the invention and an HLA-A24 antigen, and preferably include antigen-presenting cells of dendritic cells on which a complex between a cancer antigen peptide consisting of the amino acid sequence of any one of SEQ ID NOs: 2 to 6 and 66 to 68 and an HLA-A24 antigen is presented.

In order to prepare antigen-presenting cells as used in cell therapy, cells having an antigen-presenting ability are isolated from a cancer patient, and pulsed ex vivo with a peptide of the invention, or transformed with a polynucleotide of the invention or an expression vector comprising the same to present a complex between an HLA-A24 antigen and the cancer antigen peptide derived from the peptide of the invention. In this context, the "cell having an antigen-presenting ability" is not limited to a specific cell as long as it is a cell expressing on its cell surface an HLA-A24 antigen that allows a peptide of the invention to be presented, and dendritic cells, which is believed to have especially a high antigen-presenting ability, are preferably exemplified.

Substances to be pulsed to the cells having an antigen-presenting ability may be peptides of the invention, as well as polypeptides encoding the peptides of the present invention, and expression vectors comprising the same.

Antigen-presenting cells of the present invention may be prepared for example by isolating cells having an antigen-presenting ability from a cancer patient, pulsing the cells ex vivo with a peptide of the invention (e.g. the cancer antigen peptide consisting of the amino acid sequence of any one of SEQ ID NOs: 2 to 6, and 66 to 68), and preparing a complex between an HLA-A24 antigen and the cancer antigen peptide derived from the peptide of the invention (Cancer Immunol. Immunother., 46:82, 1998, J. Immunol., 158: p 1796, 1997, Cancer Res., 59: p 1184, 1999). When dendritic cells are used, antigen-presenting cells of the present invention may be prepared, for example, by isolating lymphocytes from peripheral blood of a cancer patient using Ficoll method, removing non-adherent cells, incubating the adherent cells in the presence of GM-CSF and IL-4 to induce dendritic cells, and incubating and pulsing said dendritic cells with a peptide of the invention, or the like.

When antigen-presenting cells of the invention are prepared by transforming the aforementioned cells having an antigen-presenting ability with a polynucleotide encoding the peptide of the invention (e.g., a polynucleotide encoding the peptide comprising the sequence of any one of SEQ ID NOs: 2 to 6, and 66 to 68), or with an expression vector comprising the same, such preparation of the polynucleotide in a form of DNA, may be conducted consulting, for example, *Cancer Res.*, 56: p 5672, 1996, or *J. Immunol.*, 161: p 5607, 1998. Similarly, such preparation of the polynucleotide in a form of RNA also allows to prepare antigen-presenting cells, and then for example *J. Exp. Med.*, 184: p 465, 1996 may be consulted.

The antigen-presenting cells thus prepared of the invention are useful as an active ingredient comprised in a composition for inducing CTLs or a cancer vaccine, or in cell therapy (DC therapy) as described hereinafter.

(V) CTLs of the Present Invention

The present invention provides CTLs which recognize a complex between a cancer antigen peptide derived from the peptide according to the invention and an HLA-A24 antigen.

Examples described hereinafter demonstrate that the administration of the peptides of the invention induces CTLs, showing that antigen-presenting cells on which a complex between a cancer antigen peptide derived from the peptide according to the invention and an HLA-A24 antigen is presented exist in peripheral blood mononuclear cells, and then CTLs that specifically injure cancer cells on which such a complex is presented are induced. Those CTLs that specifically recognize a complex between a cancer antigen peptide derived from the peptide according to the invention and an HLA-A24 antigen are useful in adoptive immunotherapy as described hereinafter.

CTLs of the present invention are not limited to a specific CTL as long as they specifically recognize a complex between a cancer antigen peptide derived from the peptide of the invention and an HLA-A24 antigen, and particularly include CTLs specifically recognize a complex between a cancer antigen peptide consisting of the amino acid sequence of any one of SEQ ID NOs: 2 to 6 and 66 to 68 and an HLA-A24 antigen.

In order to prepare CTLs as used in adoptive immunotherapy, for example, peripheral lymphocytes are isolated from a patient, and stimulated in nitro with a peptide of the invention (e.g. a cancer antigen peptide consisting of the amino acid sequence of any one of SEQ ID NOs: 2 to 6, and 66 to 68), or a polynucleotide encoding the peptide of the invention (e.g. a polynucleotide encoding the peptide comprising the amino acid sequence of any one of SEQ ID NOs: 2 to 6, and 66 to 68) or an expression vector comprising the same (Journal of Experimental Medicine 1999, 190: 1669).

The CTLs thus prepared of the invention are useful as an active ingredient comprised in a cancer vaccine, or in adoptive immunotherapy.

(VI) Pharmaceutical Compositions, Uses, and Methods as Cancer Vaccines

Peptides of the present invention, polynucleotides of the present invention, expression vectors of the present invention, antigen-presenting cells of the present invention, and CTLs of the present invention as described above may be used as an active ingredient comprised in a composition for inducing CTLs or a cancer vaccine, when formulated into a form as appropriate for those respective substances, which are illustrated below.

(6-1) Cancer Vaccines Comprising a Peptide of the Present Invention as an Active Ingredient CTLs induced by the peptides of the invention, which have an activity to induce CTLs, can destroy cancers via their cytotoxic activity and the lymphokine productions. Thus, the peptides of the present invention can be used as an active ingredient in a cancer vaccine for treatment or prevention of cancers. In the embodiment, the invention provides a cancer vaccine which comprises as an effective ingredient a peptide of the invention (a pharmaceutical composition usable as cancer vaccines). When the cancer vaccine of the invention is administered to a cancer patient positive for HLA-A24 and positive for WT1, the peptide (e.g. a cancer antigen peptide consisting of the amino acid sequence of any one of SEQ ID NOs: 2 to 6, and 66 to 68) is presented on an HLA-A24 antigen of antigen-presenting cells, and then CTLs specific for the complex comprising the HLA-A24 antigen efficiently proliferate, and destroy cancer cells. In this way, treatment or prevention of cancers is achieved. The cancer vaccine of the invention can be used to treat or present cancers wherein the expression level of the WT1 gene is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

In this connection, as other embodiments, the invention provides use of the peptide according to the invention in the manufacture of a cancer vaccine, and a method for treatment or prevention of a cancer, which comprises administering an effective amount of the peptide according to the invention to a cancer patient in need who is positive for an HLA-A24, and positive for WT1.

The cancer vaccines comprising a peptide of the present invention as an active ingredient may either comprise a single CTL epitope as an active ingredient, or an epitope peptide linked with another peptide (a CTL epitope or a helper epitope) as an active ingredient. Recently, it has been demonstrated that an epitope peptide wherein many CTL epitopes (antigen peptides) are linked each other has an activity to induce effectively CTLs in vivo. For example, *Journal of Immunology* 1998, 161: 3186-3194 describes that the about 30-mer epitope peptide wherein HLA-A2, -A3, -A11, B53-restricted CTL epitopes derived from a cancer antigen protein, PSA, (antigen peptide) are linked each other induced CTLs specific for the relevant CTL epitope in vivo. Also, it has been demonstrated that epitope peptides wherein a CTL epitope and a helper epitope are linked each other effectively induced CTLs. When a peptide of the invention is administered in a form of such epitope peptides, the peptide is introduced into antigen-presenting cells, and then subject to intracellular degradation to generate respective antigen peptides, which bind an HLA antigen to form complexes. The complexes are presented compactly on the cell surface of antigen-presenting cells, and then CTLs specific for the complexes efficiently proliferate, and destroy cancer cells. In this way, treatment or prevention of cancers is achieved.

Cancer vaccines comprising the peptide of the present invention as an active ingredient may be administered together with a pharmaceutically acceptable carrier such as a suitable adjuvant, or in a particulate dosage form in order to effectively establish the cellular immunity. For such purpose, those adjuvants described in the literature (*Clin. Microbiol. Rev.*, 7:277-289, 1994) are applicable, and specifically include bacterium-derived components, cytokines, plant-derived components, mineral gels such as aluminium hydroxide, surfactants such as lysolecithin and Pluronic polyol, polyanions, peptides, and oil emulsions (emulsion formulations). Also, liposomal formulations, particulate formulations in which the ingredient is bound to beads having a diameter of several μm, or formulations in which the ingredient is attached to lipids are also possible.

Administration may be achieved by, for example, intradermal, subcutaneous, intramuscular or intravenous injection. Although the dose of a peptide of the present invention in the formulations may vary depending on the disease to be treated, the age and the weight of the patient, and the like, it is typical to administer 0.0001 mg to 1000 mg, preferably 0.001 mg to 1000 mg, more preferably 0.1 mg to 10 mg of a peptide of the invention every several days to every several months.

(6-2) DNA Vaccines Comprising a Polynucleotide or an Expression Vector Encoding a Peptide of the Present Invention as an Active Ingredient Not only peptides of the present invention as described above, but also a polynucleotide encoding the peptide and an expression vector comprising the polynucleotide can be used as an active ingredient in a DNA vaccine for treatment or prevention of cancers. In the embodiment, the invention provides a cancer vaccine which comprises as an effective ingredient a polynucleotide encoding the peptide of the invention, or an expression vector comprising the polynucleotide (a pharmaceutical composition usable as cancer vaccines). In another embodiment, the invention provides a method for treatment or prevention of a cancer, which comprises administering an effective amount of the DNA vaccine according to the invention to a patient positive for an HLA-A24, and positive for WT1.

Recently, it has been demonstrated that a polynucleotide encoding an epitope peptide wherein many CTL epitopes (antigen peptides) are linked each other or a polynucleotide encoding an epitope peptide wherein a CTL epitope and a helper epitope are linked each other has an activity to induce effectively CTLs in vivo. *Journal of Immunology* 1999, 162: 3915-3925, for example, describes that a DNA encoding an epitope peptide linked with the six HLA-A2-restricted antigen peptides and the three HLA-A11-restricted antigen peptides derived from HBV, and a helper epitope (minigene) has effectively induced CTLs in response to the relevant epitopes in vivo.

Thus, an appropriate expression vector that is incorporated with a polynucleotide prepared by linking one or more polynucleotides encoding the peptide of the present invention each other, or by linking the polynucleotide of the invention with a polynucleotide encoding another peptide, can be used as an active ingredient in a cancer vaccine.

Following methods may be used to allow a polynucleotide of the invention to act as an active ingredient of cancer vaccines (DNA vaccines).

Introduction of the polynucleotide of the present invention into cells may be achieved using viral vectors, or according to any one of other procedures (*Nikkei-Science*, April, 1994, pp. 20-45; *Gekkan-Yakuji*, 36(1), 23-48 (1994); *Jikken-Igaku-Zokan*, 12(15), 1994, and references cited therein).

Examples of the methods using viral vectors include methods in which a DNA of the present invention is incorporated into a DNA or RNA virus such as retrovirus, adenovirus, adeno-associated virus, herpesvirus, vaccinia virus, poxvirus, poliovirus, or Sindbis virus, and introduced into cells. Among these methods, those using retrovirus, adenovirus, adeno-associated virus, or vaccinia virus are particularly preferred.

Other methods include a method in which an expression plasmid is directly injected intramuscularly (DNA vaccination), liposome method, Lipofectin method, microinjection, calcium phosphate method, and electroporation, and DNA vaccination and liposome method is particularly preferred.

In order to allow a polynucleotide of the present invention to act as a medicament in practice, there are an in vivo method in which the polynucleotide is directly introduced into the body, and an ex vivo method in which certain cells are removed from human, and after introducing DNA into said cells extracorporeally, the cells are reintroduced into the body (*Nikkei-Science*, April, 1994, pp. 20-45; *Gekkan-Yakufi*, 36(1), 23-48 (1994); *Jikkenn-Igaku-Zokan*, 12(15), 1994; and references cited therein). An in vivo method is more preferred.

In case of in vivo methods, the polynucleotide may be administered by any appropriate route depending on the disease and symptoms to be treated and other factors. For example, it may be administered via intravenous, intraarterial, subcutaneous, intradermal, intramuscular route, or the like. In the case of in vivo methods, the compositions may be administered in various dosage forms such as solution, and are typically formulated, for example, into the form of injection containing a polynucleotide of the present invention as an active ingredient, to which conventional carriers may also be added, if necessary. If a polynucleotide of the invention is included in liposomes or membrane-fused liposomes (such as Sendai virus (HVJ)-liposomes), the compositions may be in the form of liposome formulations such as suspension, frozen drug, centrifugally-concentrated frozen drug, or the like.

Although the dose of a polynucleotide of the invention comprised in the formulations may vary depending on the disease to be treated, the age and the weight of the patient, and the like, it is typical to administer 0.0001 mg to 100 mg, preferably 0.001 mg to 10 mg, of a polynucleotide of the invention every several days to every several months.

When the polynucleotide of the invention is administered to a cancer patient, the polypeptide corresponding to the polynucleotide is highly expressed in antigen-presenting cells. Then, respective cancer antigen peptides that are generated by intracellular degradation are bound to an HLA antigen to form complexes, which complexes are presented compactly on the cell surface of antigen-presenting cells. Then, CTLs specific for the complexes efficiently proliferate, and destroy cancer cells. In this way, treatment or prevention of cancers is achieved. The cancer vaccine of the invention comprising a polynucleotide of the invention or an expression vector comprising the polynucleotide as an active ingredient can be used to treat or present cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(6-3) Cancer Vaccines Comprising an Antigen-presenting Cell of the Present Invention as an Active Ingredient The invention provides a cancer vaccine which comprises an antigen-presenting cell of the present invention as an active ingredient.

Recently, cell therapy (DC therapy) has been reported wherein lymphocytes are isolated from the peripheral bloods of a cancer patient, and the dendritic cells induced from the lymphocytes are pulsed in vitro with a peptide or the like to prepare antigen-presenting cells, which are then returned into the patient via a subcutaneous injection or the like (*Cancer Immunol. Immunother.*, 46: 82, 1998, *J. Immunol.*, 158: p 1796, 1997, *Cancer Res.*, 59: p 1184, 1999, *Cancer Res.*, 56: p 5672, 1996, *J. Immunol.*, 161: p 5607, 1998, *J. Exp. Med.*, 184: p 465, 1996). Thus, a cancer vaccine comprising an antigen-presenting cell of the present invention as an active ingredient can be used as an active ingredient in a cancer vaccine as used in cell therapy.

A cancer vaccine which comprises the antigen-presenting cells of the invention as an active ingredient preferably contains physiological saline, phosphate buffered saline (PBS), medium, or the like to stably maintain the antigen-presenting cells. It may be administered, for example, intravenously, subcutaneously, or intradermally. The dose is exemplified by those described in the aforementioned literatures.

By reintroducing the cancer vaccine into the body of the patient, specific CTLs are efficiently induced in patients positive for HLA-A24, and positive for WT1 so as to achieve the treatment or the prevention of the cancers. The cancer vaccine which comprises the antigen-presenting cells of the invention as an active ingredient can be used to treat or present cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(6-4) Cancer Vaccines Comprising a CTL of the Present Invention as an Active Ingredient The invention provides a cancer vaccine which comprises as an effective ingredient a CTL of the invention (a pharmaceutical composition usable as cancer vaccines). The CTL of the invention are useful in adoptive immunotherapy hereinafter.

For melanomas, it has been observed that an adoptive immunotherapy achieves a therapeutic effect wherein tumor-infiltrating T cells taken from the patient himself/herself are cultured ex vivo in large quantities, and then returned into the patient (*J. Natl. Cancer. Inst.*, 86:1159, 1994). Likewise, in mouse melanoma, suppression of metastasis has been observed by in vitro stimulation of splenocytes with cancer antigen peptide TRP-2, thereby proliferating CTLs specific for the cancer antigen peptide, and administering said CTLs into a melanoma-grafted mouse (*J. Exp. Med.*, 185:453, 1997). This resulted from in vitro proliferation of CTLs that specifically recognize the complex between an HLA antigen and the cancer antigen peptide on antigen-presenting cells. Accordingly, a method for treating cancers believed to be useful, which comprises stimulating in vitro peripheral blood lymphocytes from a patient using a peptide, or a polynucleotide or an expression vector according to the present invention to proliferate tumor-specific CTLs, and subsequently returning the CTLs into the patient. Thus, the CTLs of the invention may be used as an active ingredient comprised in cancer vaccine used in adoptive immunotherapy.

A cancer vaccine which comprises the CTLs of the invention as an active ingredient preferably contains physiological saline, phosphate buffered saline (PBS), medium, or the like to stably maintain the CTLs. It may be administered, for example, intravenously, subcutaneously, or intradermally. The dose is exemplified by those described in the aforementioned literatures.

By reintroducing the cancer vaccine into the body of the patient, cytotoxic effect of CTLs on cancer cells is enhanced in patients positive for HLA-A24 and positive for WT1, and destroys cancer cells, so as to achieve the treatment of the cancers. The cancer vaccine which comprises the CTLs of the invention as an active ingredient can be used to treat or present cancers wherein the level of the WT1 gene expression is elevated, including blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(VII) Cancer Vaccines Comprising a Peptide Based on the Amino Acid Sequence of SEQ ID NO: 7

In the present invention, it has been that the peptide having the amino acid sequence of Arg Val Pro Gly Val Ala Pro Thr Leu (SEQ ID NO: 7) has an activity to induce CTLs in vivo. A cancer antigen peptide consisting of the amino acid sequence of SEQ ID NO: 7 was described as a peptide having a sequence expected to bind to HLA-A24 antigen in WO00/18795. However, it has been found for the first time in the present invention that the peptide has an activity to induce CTLs in vivo, and is available as cancer vaccines.

Thus, the invention provides a pharmaceutical composition or a cancer vaccine which comprises any one of the substances selected from the group consisting of:
a) a peptide which comprises the amino acid sequence of SEQ ID NO: 7,
b) a polynucleotide which encodes the peptide as shown above a),
c) an expression vector which comprises the polynucleotide as shown above b),
d) a cell which comprises the expression vector as shown above c),
e) an antigen-presenting cell on which a complex between a cancer antigen peptide derived from the peptide as shown above a) and an HLA-A24 antigen is presented, and
f) a CTL which recognizes a complex between a cancer antigen peptide derived from the peptide as shown above a) and an HLA-A24 antigen. Further, the invention also provides use of any one of the peptide, the polynucleotide, the expression vector, the transformant, the antigen-presenting cell, and the CTL as described above in the manufacture of a cancer vaccine, and a method for treatment or prevention of a cancer, which comprises administering a therapeutically or prophylactically effective amount of any one of those substances to a cancer patient in need who is positive for an HLA-A24, and positive for WT1.

The preparations for those substances described in a) to f) above, and the uses of them as cancer vaccines are the same as those described in each section for the peptide, the polynucleotide, the expression vector, the antigen-presenting cell, and the CTL according to the invention.

EXAMPLES

The present invention is further illustrated by the following examples, but is not limited by these examples in any respect.

References hereinafter describe the preparation of a transgenic mouse expressing an HLA-A24, and the details are described in WO 02/47474 (the international publication date: Jun. 20, 2002, PCT/JP01/10885 (the international application date: Dec. 12, 2001 (the priority date: Dec. 13, 2000))).

Reference 1

Cloning of HLA-A2402 Genomic DNA Fragment (1) Cloning of HLA-A2402 Genomic DNA Fragment For the purpose of cloning a human HLA-A2404 genomic DNA by PCR, a human tumor cell line, RERF-LC-AI cells (Riken Cell Bank RCB0444) were cultured and the human genomic DNA was purified using Genomic Prep Cells and Tissue DNA Isolation Kit (Amersham) as per attached protocol. GenBank database was then searched for HLA-A2402 genomic DNA needed for the construction of chimeric HLA gene, which revealed that one registered under Accession No. Z72422 was relevant, but a 270 bp promoter region was not registered. The construction of the objective transgenic mouse requires promoter, exons 1 to 3 and introns 1 to 3. To clone a HLA-A2402 genomic DNA containing a promoter, PCR was conducted using the upstream primer, HLA26-IF:

```
                                  (36mer, SEQ ID NO: 36)
5'-CCC AAG CTT ACT CTC TGG CAC CAA ACT CCA TGG

GAT-3',
``` which was designed making reference to the nucleotide sequence of the promoter of HLA-A2601 (Accession No. AB005048) frequently found in the Japanese; and the downstream primer, A24-BglII 30:

```
                                  (30mer, SEQ ID NO: 37)
5'-CGG GAG ATC TAC AGG CGA TCA GGT AGG CGC-3'
``` which comprises a modification in the nucleotide sequence in intron 3, specifically, the nucleotide at 1282 position from the 5' terminus of Accession No. Z72422 is changed from G to A.

Said modification of nucleotide was needed for the following reasons. The present reference aims at obtaining an transgenic mouse expressing a chimeric HLA consisting of exons 1-3 of HLA-A2402 and exons 4-8 of H-2K$^b$, which chimeric HLA can be constructed by ligating the region upstream from the BamHI restriction site in intron 3 of HLA-A2402 genomic DNA and the region downstream from intron 3 of H-2K$^b$ genomic DNA and, for this end, it was necessary to construct an artificial BglII restriction site in the intron 3 of HLA-A2402.

PCR cloning of a HLA-A2402 genomic DNA fragment was then conducted using Native Pfu DNA Polymerase (Stratagene) having a high 3'→5' exonuclease activity as per attached protocol, and the pair of primers above. The PCR comprised heat treatment at 95° C. for 45 seconds, 35 cycles of reaction at 95° C. for 45 seconds, 66° C. for 1 minute and 72° C. for 4 minutes, and reaction at 72° C. for 10 minutes, followed by cooling to 4° C. The amplified gene fragment was ligated into HindIII and BamHI restriction sites of a phagemid vector, pBluescript, to obtain a recombinant plasmid. The recombinant plasmid was introduced into *E. coli* JM109 (Toyobo) by heat shock method at 42° C., and the white colonies of *E. coli* to which the recombinant plasmid had been introduced were selected on an ampicillin (50 μg/ml)-containing LB agar medium (1% bacto-tryptone, 0.5% yeast extract, 1% NaCl, 2% agar) coated with X-Gal and IPTG to obtain the transformants.

(2) Determination of Nucleotide Sequence of HLA-A2402 Promoter Region

Four transformants obtained in the above were incubated overnight in a LB medium containing ampicillin (3 ml), followed by purification of the plasmid clone contained in each transformant by alkaline lysis method (*CURRENT PROTOCOLS IN MOLECULAR BIOLOGY*, edited by F. M. Ausubel, et al., John Wiley & Sons, Inc.). The nucleotide sequence was then determined by means of ABI PRISM™ 377 DNA Sequencing System (PE Biosystems). Samples for sequencing were subjected to ABI PRISM™ Dye Terminator Cycle Sequencing Ready Reaction kit (PE Biosystems) to sequence each clone as per attached protocol. When the promoters of respective clones were compared, it was revealed that they were totally the same. Thus, the nucleotide sequence of the promoter region of HLA-A2402 was determined, which sequence had not been registered at GenBank database. The nucleotide sequence registered under the Accession No. Z72422 was compared with that of respective clones, which revealed that there is one normal clone free of PCR mutation.

Reference 2

Cloning of H-2K$^b$ Genomic DNA Fragment (1) Cloning of H-2K$^b$ Genomic DNA Fragment Mouse tumor cell line EL4 (ATCC T1B-39) was cultured, and mouse genomic DNA was purified and used in the PCR cloning. Purification of DNA was carried out using TaKaRa LA Taq™ (Takara Shuzo) suited for the amplification of a long-chain DNA as per the attached protocol. The GenBank database was then searched for H-2 Kb gene needed for the construction of chimeric HLA gene, which revealed that said gene was divided in two segments registered under the Accession Nos. v00746 and v00747. The upstream 1594 bp region of H-2K$^b$ down to midstream of intron 3 was registered as v00746, and the downstream 1837 bp region of H-2K$^b$ down to midstream of intron 7 was registered as v00747. Because there was no BamHI restriction site in intron 3, which is divided and registered as v00746 and v00747, the H-2K$^b$ gene registered at the database was thought to have an incomplete length.

There are homologous pseudogenes or highly homologous genes in H-2K$^b$ gene (*Cell.*, 25:683, 1981). PCR was conducted with TaKaRa LA Taq™ (Takara Shuzo) as per attached protocol using the upstream primer H-2 KB F3:

```
                                 (30mer, SEQ ID NO: 38)
5'-CGC AGG CTC TCA CAC TAT TCA GGT GAT CTC-3'
``` which has a low homology with said complementary gene and is coded by exon 3 of v00746, and the downstream primer H-2 KB 3R:

```
                                 (38mer, SEQ ID NO: 39)
5'-CGG AAT TCC GAG TCT CTG ATC TTT AGC CCT GGG GGC

TC-3'
``` which corresponds to v00747 having EcoRI restriction site added at the terminus, and using the purified mouse genomic DNA above as a template. The PCR comprised 25 cycles of reaction at 98° C. for 10 seconds and 66° C. for 4 minutes, and reaction at 68° C. for 10 minutes, followed by cooling to 4° C.

The amplified gene fragment was ligated into KpnI and EcoRI restriction sites of phagemid vector pBluescript to obtain a recombinant plasmid. The recombinant plasmid was introduced into *E. coli* JM109 (Toyobo) by heat shock method at 42° C., and the white colonies of *E. coli* to which the recombinant plasmid had been introduced were selected on an ampicillin-containing LB agar medium coated with X-Gal and IPTG to obtain the transformants. Three transformants were incubated overnight in a LB medium containing ampicillin (3 ml). The plasmid clone contained in each transformant was purified and subjected to analysis of nucleotide sequence in a similar manner to the above. The nucleotide sequences of the three respective clones and that of v00747 were compared, which revealed that there was one PCR mutation independently in the two clones and three PCR mutations in the one clone. There were the five nucleotides commonly found in these three clones, which were different from those of v00747. These nucleotides were found in regions corresponding to intron 6 and 3' non-coding region. Furthermore, the unregistered intron 3 region contained a nucleotide resulted from PCR mutation that was different among 3 clones. The determination of nucleotide sequence was therefore partly impossible concerning the unregistered region, which could be achieved after re-cloning the unregistered intron 3 region using a polymerase with high 3'→5' exonuclease activity.

(2) Determination of Nucleotide Sequence of H-2K$^b$ Intron 3

To determine the nucleotide sequence of the unregistered region, a region containing the unregistered intron 3 region was cloned by PCR with Native Pfu DNA Polymerase (Stratagene) as per attached protocol using the purified mouse genomic DNA as a template. The PCR was carried out using an upstream primer H-2 kb F5:

```
                                 (29mer, SEQ ID NO: 40)
5'-AGG ACT TGG ACT CTG AGA GGC AGG GTC TT-3',
``` which is registered as v00746, and the downstream primer H-2 kb 5R:

```
                                 (30mer, SEQ ID NO: 41)
5'-CAT AGT CCC CTC CTT TTC CAC CTG TGA GAA-3',
``` which is registered as v00747. The PCR comprised heat treatment at 95° C. for 45 seconds, 25 cycles of reaction at 95° C. for 45 seconds, 68° C. for 1 minute and 72° C. for 4 minutes, and reaction at 72° C. for 10 minutes, followed by cooling to 4° C. The amplified gene fragment was ligated into BamHI and BglII restriction sites of phagemid vector pBluescript to obtain a recombinant plasmid. The recombinant plasmid was introduced into *E. coli* JM109 (Toyobo) by heat shock method at 42° C., and white colonies of *E. coli* to which the recombinant plasmid has been introduced were selected on ampicillin (50 µg/ml)-containing LB agar medium (1% bacto-tryptone, 0.5% yeast extract, 1% NaCl, 2% agar) coated with X-Gal and IPTG to obtain the transformants. Five transformants were incubated overnight in a LB medium containing ampicillin (3 ml) and the plasmid clone contained in each transformant was purified and subjected to analysis of nucleotide sequence in a similar manner to the above. The intron 3 regions of respective clones analyzed were compared, which revealed that the sequences agreed completely. The nucleotide sequence of intron 3 region was thus determined. In addition, the region spanning from the BamHI site in the unregistered region to v00747 revealed to be 463 bp.

(3) Construction of H-2K$^b$ Genomic DNA

As a result of determination of nucleotide sequence of the unregistered region in (2) above, the entire nucleotide sequence of H-2 Kb genomic DNA necessary for the construction of the objective chimeric HLA gene was determined. It became clear that the objective H-2K$^b$ genomic DNA can be constructed by combining two clones obtained in the above, i.e., H-2K$^b$#20 free of PCR mutation and H-2K$^b$#26 free of PCR mutation, in 5'- and 3'-regions, respectively. Accordingly, these clones were cleaved by a restriction enzyme and respective regions having no PCR mutations were combined to construct the H-2K$^b$ genomic DNA free of PCR mutations. The schematic diagram for construction is shown in FIG. 1.

The both clones were cleaved at the BglII and EcoRI restriction sites and ligated to obtain recombinant plasmid.

The recombinant plasmid was introduced into *E. coli* JM109 (Toyobo) by heat shock method at 42° C., and white colonies of *E. coli* to which the recombinant plasmid has been introduced were selected on an ampicillin-containing LB agar medium coated with X-Gal and IPTG to obtain the transformants. Three transformants were incubated overnight in a LB medium containing ampicillin (3 ml). The plasmid clone contained in each transformant was purified by alkaline lysis method and subjected to sequence analysis in a similar manner to the above. As a result, it was revealed that all the transformants contained a plasmid encoding H-2K$^b$ genomic DNA free of PCT mutation.

The nucleotide sequence of H-2K$^b$ genomic DNA herein obtained corresponds to the nucleotide sequence downstream from the nucleotide at position 1551 of SEQ ID NO: 33 inclusive, which is described below.

Reference 3

Construction of Chimera Genomic DNA (HLA-A2402/K$^b$ DNA)

Figure 2:
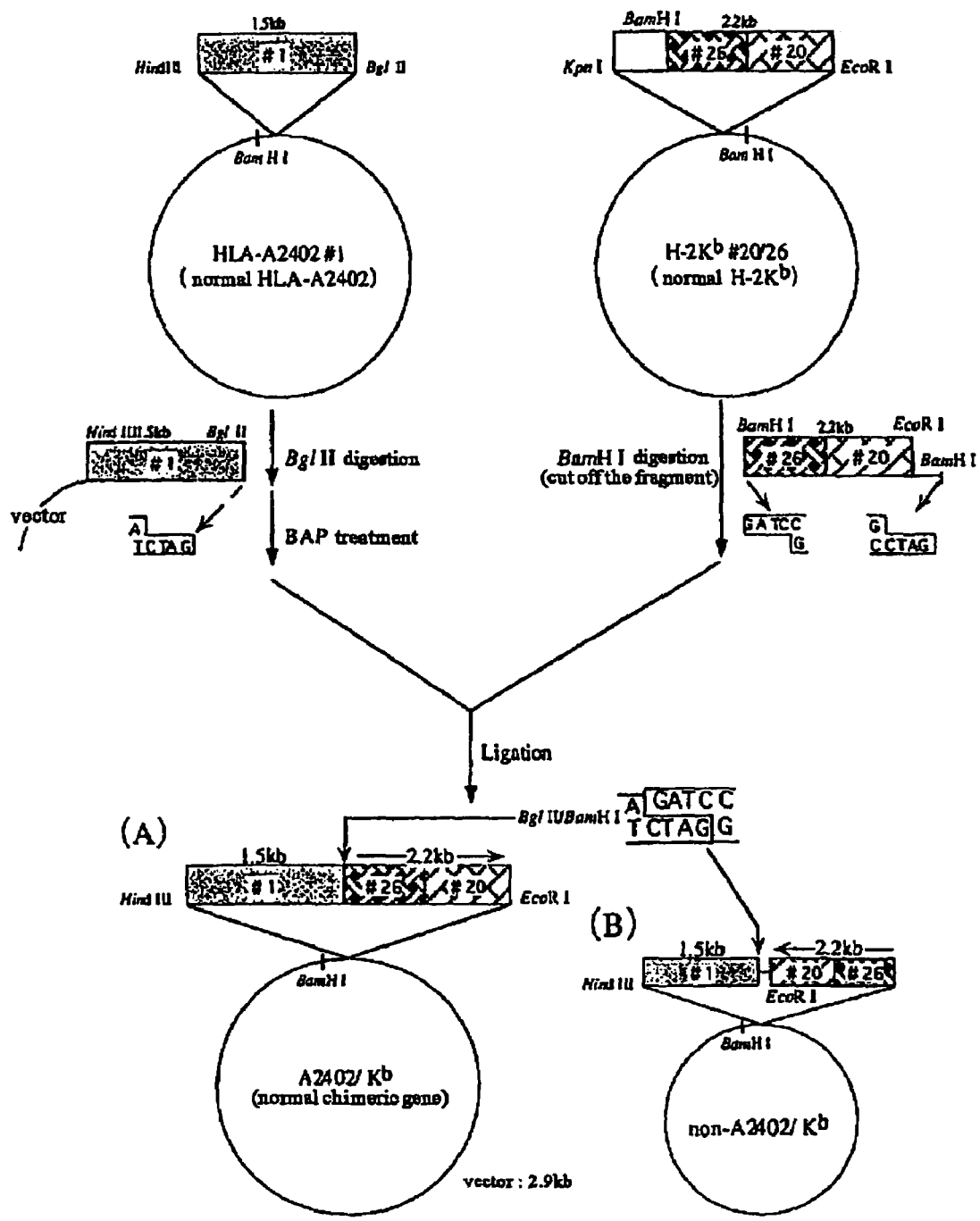
FIG. 2 is a schematic diagram showing the process for preparing the chimera gene of the present invention, HLA-A2402/K$^b$ gene.

The Plasmid HLA-A2402# 1 containing HLA-A2402 genomic DNA obtained in Reference 1 above was cleaved at BglII restriction site and the plasmid H-2K$^b$#20/26 containing H-2K$^b$ genomic DNA obtained in Reference 2 above was cleaved at BamHI restriction site, and the resultant fragments were ligated to give a recombinant plasmid. The schematic construction is shown in FIG. 2. The recombinant plasmid was introduced into *E. coli* JM109 (Toyobo) by heat shock method at 42° C., and white colonies of *E. coli* to which the recombinant plasmid has been introduced were selected on a ampicillin-containing LB agar medium coated with X-Gal and IPTG to obtain the transformants. Ten transformants were incubated overnight in a LB medium containing ampicillin (3 ml). The plasmid clone contained in each transformant was purified and subjected to sequence analysis in a similar manner to the above. As a result, it was revealed that three transformants contained a plasmid carrying the intended chimeric gene HLA-A2402/K$^b$ DNA, which may be referred to as simply "A2402/K$^b$ DNA". The genomic sequence of the constructed HLA-A2402/K$^b$ is shown in SEQ ID NO: 33.

Reference 4

Splicing Analysis of Chimera Genomic DNA

Mouse tumor cell line EL4 was transfected with the constructed chimeric HLA gene (HLA-A2402/K$^b$ gene) with Electro Gene Transfer GTE-10 (Shimadzu) as per the attached protocol. Two days later, total RNA was purified from transfected EL4 cells and un-transfected EL4 cells (control) by using ISOGEN (Nippon Gene) as per the attached protocol. Reverse transcription was performed using SuperScript Choice System (GIBCO BRL) as per the attached protocol using Oligo(dT)$_{12-18}$ and a part of said RNA as a template to synthesize cDNA. In addition, chimera gene was specifically amplified by PCR using Native Pfu DNA Polymerase (Stratagene) and a part of said cDNA as a template.

PCR was conducted using an upstream primer Chimera-F2:

5'-CGA ACC CTC GTC CTG CTA CTC TC-3' (23mer, SEQ ID NO: 42), which is encoded in exon 1 of HLA-A2402 gene and has low homology with H-2K$^b$ gene, and a downstream primer Chimera-R2:

5'-AGC ATA GTC CCC TCC TTT TCC AC-3' (23mer, SEQ ID NO: 43), which is encoded in exon 8 of H-2K$^b$ gene and has low homology with HLA-A2402 gene, under the conditions of heat treatment at 95° C. for 45 seconds, 40 cycles of reaction at 95° C. for 45 seconds, 53° C. for 1 minute and 72° C. for 2 minutes, and reaction at 72° C. for 10 minutes, followed by cooling to 4° C.

Figures 3C, 4A:
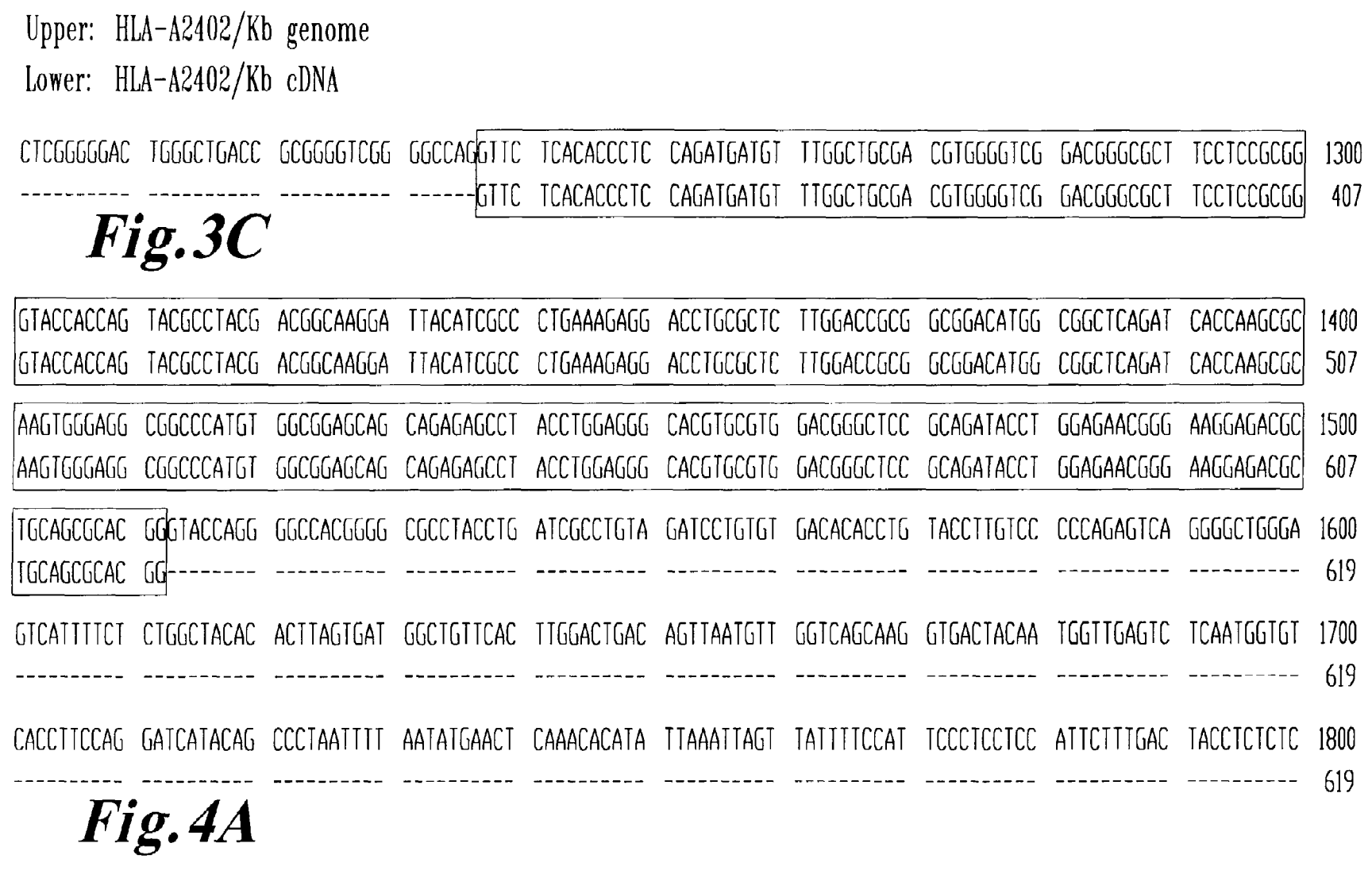

As a result, about 1.1 kbp gene fragments were specifically amplified only in transfected EL4 cells. Based on this result, it was estimated that the transferred chimera genomic DNA was transcribed in mouse cells, that is, HLA promoter functioned and mRNA spliced at the predicted position was expressed. The amplified fragment by PCR above was sequenced, and whereby the base sequence of cDNA encoding HLA-A2402/K$^b$ was determined as expected. The base sequence of cDNA encoding said HLA-A2402/K$^b$ is shown in SEQ ID NO: 34 and the amino acid sequence thereof in SEQ ID NO: 35. Furthermore, FIGS. 3 to 5 show the relationship between the genome sequence of HLA-A2402/K$^b$ (SEQ ID NO: 33) and the cDNA sequence (SEQ ID NO: 34) aligned in parallel.

Reference 5

Preparation of DNA Solution for Microinjection

Plasmid (11 µg) encoding the constructed chimeric HLA gene was digested with restriction enzymes HindIII and EcoRI, and also restriction enzyme DraI that cleaves only vector. After gel electrophoresis (1% SeaKem GTG, Nippon Gene), gel fragment containing chimera DNA was recovered. A DNA solution for microinjection was prepared by purifying the transgene with Prep-A-Gene purification kit (BioRad) as per the attached protocol and dissolving in ¹/₁₀ TE buffer (10 mM Tris (pH 8), 0.1 mM EDTA (pH 8)).

Reference 6

Introduction into Mouse Fertilized Egg and Identification of Transgenic Mouse

The injection of chimera gene construct was performed using fertilized eggs derived from a C57BL/6 mouse strain.

The fertilized eggs of C57BL/6 mouse strain were used because C57BL/6 mice express as the class 1 molecule H-2b not H-2K$^d$ having similar binding motifs to HLA-A2402. Accordingly, a transgenic mouse of said C57BL/6 line can advantageously avoid cross reaction when an HLA-A24-restriced antigen peptide is administered, because the endogenous mouse class I does not present said peptide on the cell surface.

In the first injection, the chimera construct was injected into 81 fertilized eggs, and the eggs were transferred to 4 recipient mice, which resulted in no delivery. In the second injection, the chimera construct was injected into 50 fertilized eggs, and the eggs were transferred to 2 recipient mice, which resulted in delivery of 4 offspring, but all of them died before weaning. In the third injection, the chimera construct was injected into 101 fertilized eggs, and the eggs were transferred to 4 recipient mice, which resulted in delivery of 11 offspring, but all of them died before weaning.

In the fourth injection, the chimera construct was injected into 168 fertilized eggs, and the eggs were transferred to 6 recipient mice, which resulted in delivery of 22 offspring, and 19 of them were weaned from the breast. Four of them, i.e., 01-4, 04-2, 05-1 and 05-6 were identified as a transgenic mouse; however, 01-4 mouse was unable to mate due to malformation and 05-6 mouse died shortly after weaning. In the fifth injection, the chimera construct was injected into 221 fertilized eggs, and the eggs were transferred to 8 recipient mice, which resulted in delivery of 14 offspring, and 6 of them were weaned from the breast. Three of them, i.e., 04-1, 04-5 and 04-6 were identified as a transgenic mouse. In the sixth injection, the chimera construct was injected into 225 fertilized eggs, and the eggs were transferred to 8 recipient mice, which resulted in delivery of 13 offspring, and 9 of them were weaned from the breast. Three of them, i.e., 10-5, 14-1 and 15-2 were identified as a transgenic mouse.

The transgenic mouse was identified by carrying out PCR with TaKaRa LA Taq™ (Takara Shuzo) as per the attached protocol using the same primers as those used for cloning of HLA-A2402 gene (HLA26-1F, SEQ ID NO: 36; and A24-BglII30, SEQ ID NO: 37) and a tail DNA preparation as a template, applying to 1% agarose gel electrophoresis, and selecting a mouse on the basis of the existence of 1.5 kbp DNA band.

Reference 7

Expression of Transgene Product in Transgenic Mouse

Splenocytes were recovered from spleens isolated from mice of 8 transgenic lines 04-2, 05-1, 04-1, 04-5, 04-6, 10-5, 14-1 and 15-2 constructed in Reference 6, according to *CURRENT PROTOCOLS IN IMMUNOLOGY*, edited by J. E. Coliganl et al., John Wiley & Sons, Inc. Expression of HLA-A2402/$K^b$, which is a protein derived from transgene, on the cell surface of transgenic mouse splenocytes was analyzed by flow cytometry. As control, splenocytes prepared from C57BL/6 strain were used. Specifically, $5 \times 10^6$ splenocytes were stained by FITC-labeled anti-HLA antibody B9.12.1 (Immunotech). Endogenous mouse class I was stained by FITC-labeled anti-H-$2K^b$ monoclonal antibody AF6-88.5 (Pharmingen).

As a result, 5 lines, i.e., 04-1, 04-5, 10-5, 14-1 and 15-2 showed expression specific for HLA class I. Among them, only 04-1 line revealed to have ability of reproduction. On the other hand, the other 3 lines, i.e., 04-6, 04-2 and 05-1, showed no expression specific for HLA class I. Thus, 8 transgenic mouse lines were constructed but, among them, only 04-1 line showed class I expression manner and achieved homozygosity.

Reference 8

Establishment of Transformed Cells Expressing HLA-A2402

A transformed cell Jurkat-A2402/$K^b$ which stably expresses HLA-2402/$K^b$ was established in order to evaluate the CTL-inducing ability of the transgenic mouse prepared in the above.

(1) Construction of Expression Vector

Spleen was removed from a Tg mouse and splenocytes were prepared. Total RNA was prepared with ISOGEN (Nippon Gene) as per the attached protocol. Reverse transcription was then performed with SuperScript Choice System (GIBCO BRL) as per the attached protocol using Oligo $(dT)_{12-18}$ and, as a template, a part of said RNA to synthesize cDNA. PCR was then conducted by LA-PCR kit (Takara Shuzo) as per the attached protocol using a part of said cDNA as a template, and the upstream primer chi.PF1:
5'-CCC AAG CTT CGC CGA GGA TGG CCG TCA TGG CGC CCC GAA-3' (SEQ ID NO: 44); and the downstream primer chi.PR1:
5'-CCG GAA TTC TGT CTT CAC GCT AGA GAA TGA GGG TCA TGA AC-3', SEQ ID NO: 45). PCR comprised heat treatment at 95° C. for 45 seconds, 25 cycles of reaction at 95° C. for 45 seconds, 60° C. for 1 minute and 68° C. for 2 minutes, and reaction at 72° C. for 10 minutes, followed by cooling to 4° C. The PCR amplified gene was introduced into an expression vector pcDNA3.1 (+)(Invitrogen) to construct an expression vector encoding HLA-A2402/Kb.

(2) Introduction into Jurkat Cells

The vector above (10 μg) was linearized by digesting with PvuI restriction enzyme. Jurkat cells (ATCC TIB-152) $5 \times 10^6$ were transfected with the constructed chimeric HLA gene by means of a gene-transfer device (GIBCO BRL) as per the attached protocol. Cells were seeded into 96-well plate at 0.5 cells/well and cultured in a medium containing Geneticin (0.6 mg/ml). As a result, cell proliferation was observed in 6 wells (6 clones, A-2, A-4, A-6, A-9, A-10 and A-11). Among them, A-10 showed the highest expression of transgene and said clone was established as Jurkat-A2402/$K^b$ cell.

Reference 9

Test for CTL-Inducing Ability of Transgenic Mouse

Human tumor antigen HER-2/neu is known to be overexpressed in breast, ovarian and lung cancers, and is shown by in vitro experiment that a peptide derived therefrom has an activity of inducing specific CTLs in peripheral blood of HLA-A24 positive healthy subjects (*Int. J. Cancer.*, 87:553, 2000).

The transgenic mouse was immunized with HLA-A24-restriced peptide HER-2/$neu_{780-788}$ (SEQ ID NO: 46) derived from said human tumor antigen and MHC Class II I-$A^b$-restricted helper peptide originated from tetanus toxin (Phe Asn Asn Phe Thr Val Ser Phe Trp Leu Arg Val Pro Lys Val Ser Ala Ser His Leu Glu; SEQ ID NO: 32), and examined whether specific CTLs are induced as is the case with human. Specifically, HER-2/$neu_{780-788}$ and helper peptide were adjusted to 40 mg/ml and 20 mg/ml, respectively, in DMSO and diluted with a physiological saline to 2 mg/ml and 1 mg/ml, respectively. They were mixed with an equal amount of Freund's incomplete adjuvant (Wako Pure Chemical Industries, Ltd.) using a glass syringe to prepare a water-in-oil emulsion. The resultant preparation (200 μl) was injected into a transgenic mouse (04-1 line) subcutaneously in the base of the tail for immunization. Seven days after the initiation of experiment, the spleen was removed and grounded on the frosted part of glass slide, and splenocytes were recovered and prepared. A portion of the splenocytes undergone hemolysis treatment with an ACK buffer (0.15 M $NH_4Cl$, 10 mM $KHCO_3$, 0.1 mM EDTA, pH 7.2-7.4) was exposed to X ray radiation (2,000 rad), pulsed with the above-mentioned peptide (100 μg/ml) for 1 hour, and seeded into a 24-well plate at $0.7 \times 10^6$/well. Non-radiated, non-peptide-pulsed splenocytes ($7 \times 10^6$/well) were added together and stimulated again at 37° C. (final concentration of peptide, 1 μg/ml). In vitro stimulation was carried out for 6 days in 10 ml of a culture solution (CTM culture solution) containing 10% FCS, 10 mM HEPES, 20 mM L-glutamine, 1 mM sodium pyruvate, 1 mM MEM nonessential amino acid, 1% MEM vitamin and 55 μM 2-mercaptoethanol in RPMI 1640 medium.

On the other hand, Jurkat-A2402/$K^b$ cells prepared in Reference 8 were labeled with $^{51}Cr$ (3.7 MBq/$10^6$ cells) and pulsed with the peptide above at 100 μg/ml for one hour. The labeling was carried out over 2 hours, and 1 hour after initiation of labeling, peptide was added to make the final concentration 100 μg/ml. Cells that were not pulsed with peptide were prepared as control target cells.

Figure 6:
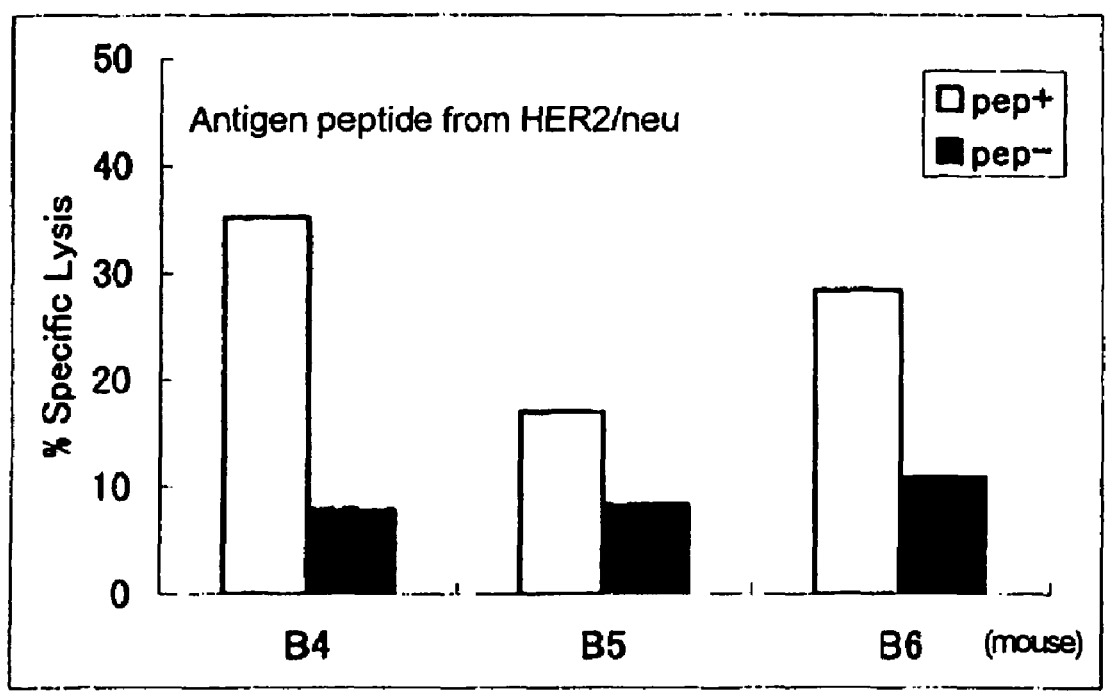
FIG. 6 is a graph showing that specific CTLs were induced when an HLA-A24 expressing transgenic mouse of the invention was immunized with an antigen peptide (HER2/neu$_{780-788}$) derived from HER-2/neu. The cytotoxic activity (% Specific Lysis) and the name of respective transgenic mice are depicted in the vertical and horizontal axes, respectively. In the figure, "pep+" refers to the results obtained using target cells pulsed with a peptide, and "pep−" refers to the results obtained using cells not pulsed with any peptide.

CTL-inducing activity was determined by $^{51}Cr$ release assay (*J. Immunol.*, 159:4753, 1997), wherein the previously prepared transgenic mouse splenocyte preparation was added to said Jurkat-A2402/$K^b$ cells as the target cells. The results are shown in FIG. 6. As a result, induction of specific CTLs by stimulation with HER-2/$neu_{780-788}$ was observed.

Figure 7:
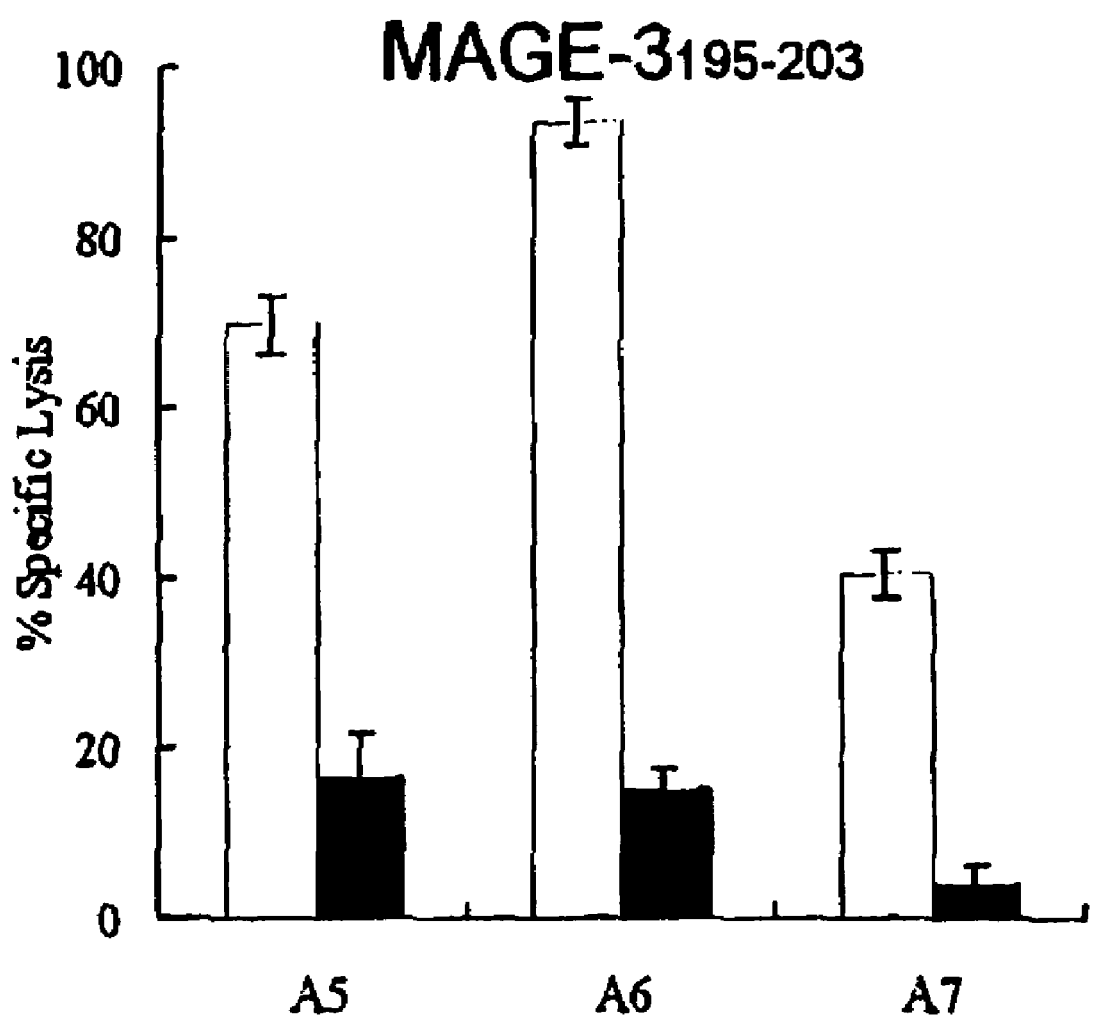
FIG. 7 is a graph showing that specific CTLs were induced when an HLA-A24 expressing transgenic mouse of the invention was immunized with an antigen peptide (MAGE-3$_{195-203}$) derived from MAGE-3. In the figure, the meanings of the vertical axis, the horizontal axis, the open bar, and the solid bar are the same as those described in regard to FIG. 6.
Figure 8:
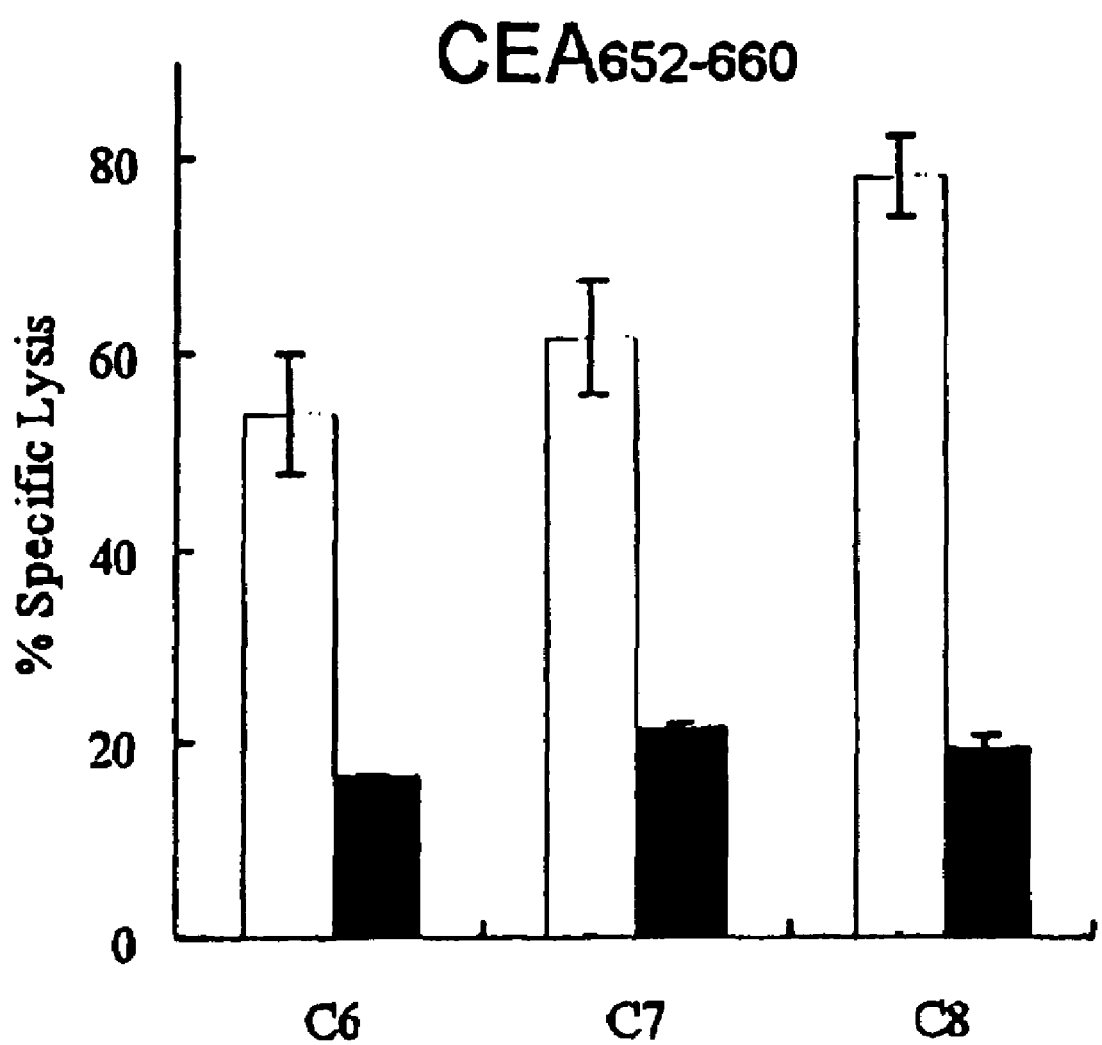
FIG. 8 is a graph showing that specific CTLs were induced when an HLA-A24 expressing transgenic mouse of the invention was immunized with an antigen peptide (CEA$_{652-660}$) derived from CEA. In the figure, the meanings of the vertical axis, the horizontal axis, the open bar, and the solid bar are the same as those described in regard to FIG. 6.
Figure 9:
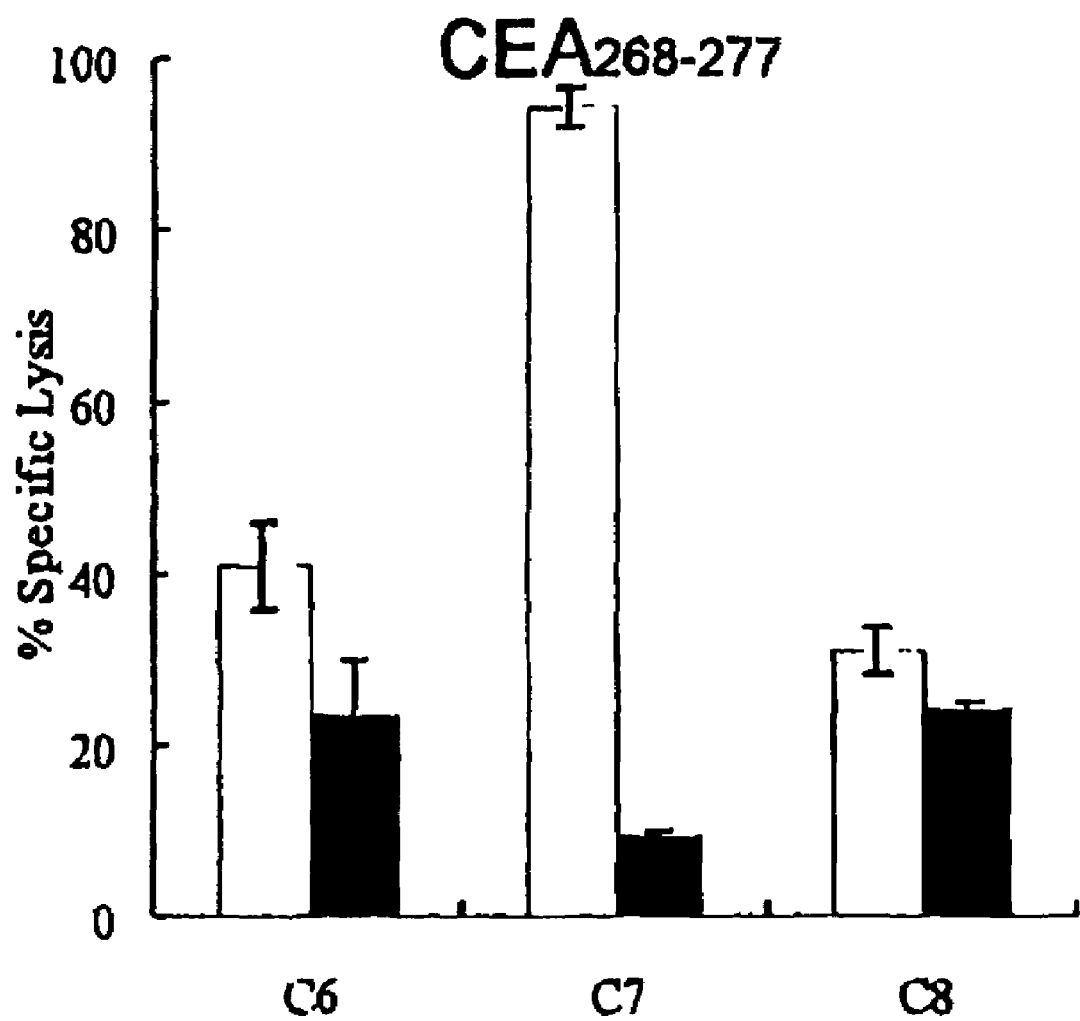
FIG. 9 is a graph showing that specific CTLs were induced when an HLA-A24 expressing transgenic mouse of the invention was immunized with an antigen peptide (CEA$_{268-277}$) derived from CEA. In the figure, the meanings of the vertical axis, the horizontal axis, the open bar, and the solid bar are the same as those described in regard to FIG. 6.
Figure 10:
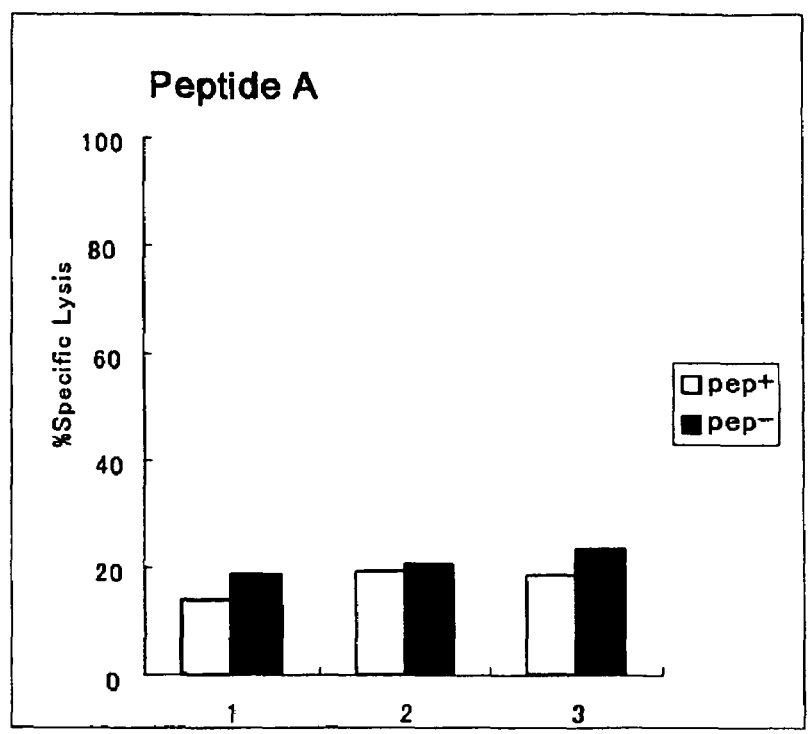
FIG. 10 is a graph showing that no specific CTL was induced when an HLA-A24 expressing transgenic mouse of the invention was immunized with an antigen peptide (peptide A, WT1$_{126-134}$) derived from human WT1. In the figure, the meanings of the vertical axis, the horizontal axis, the open bar, and the solid bar are the same as those described in regard to FIG. 6.
Figure 11:
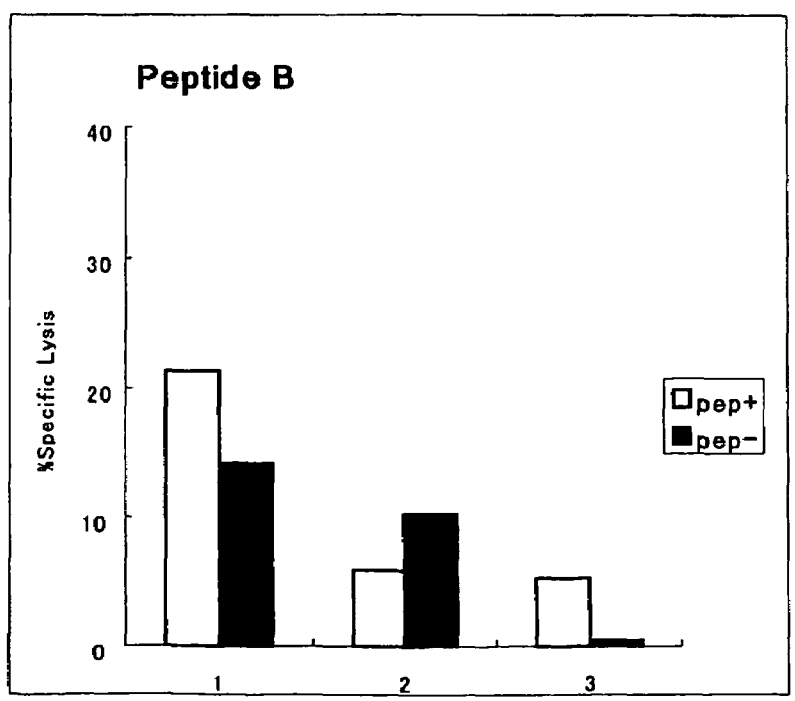
FIG. 11 is a graph showing that specific CTLs were induced when an HLA-A24 expressing transgenic mouse of the invention was immunized with an antigen peptide (peptide B, WT1$_{302-310}$) derived from human WT1. In the figure, the meanings of the vertical axis, the horizontal axis, the open bar, and the solid bar are the same as those described in regard to FIG. 6.
Figure 12:
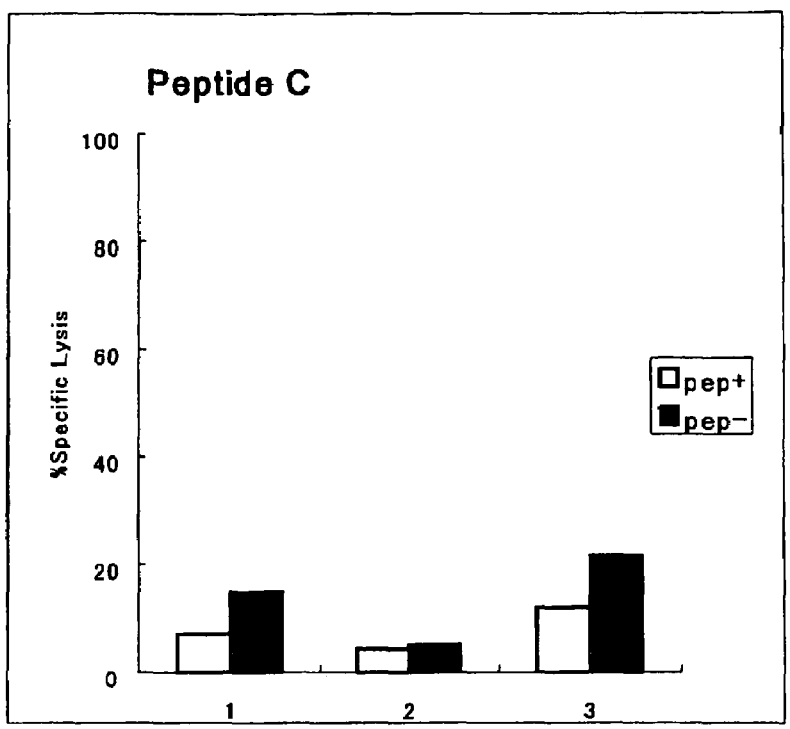
FIG. 12 is a graph showing that no specific CTL was induced when an HLA-A24 expressing transgenic mouse of the invention was immunized with an antigen peptide (peptide C, $WT1_{417-425}$) derived from human WT1. In the figure, the meanings of the vertical axis, the horizontal axis, the open bar, and the solid bar are the same as those described in regard to FIG. 6.
Figure 13:
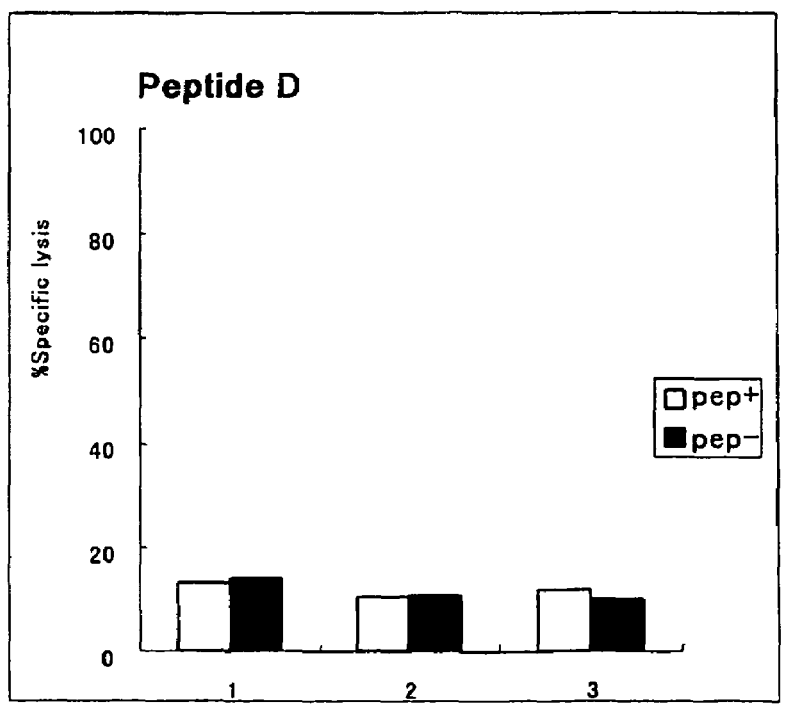
FIG. 13 is a graph showing that no specific CTL was induced when an HLA-A24 expressing transgenic mouse of the invention was immunized with an antigen peptide (peptide D, $WT1_{285-294}$) derived from human WT1. In the figure, the meanings of the vertical axis, the horizontal axis, the open bar, and the solid bar are the same as those described in regard to FIG. 6.
Figure 14:
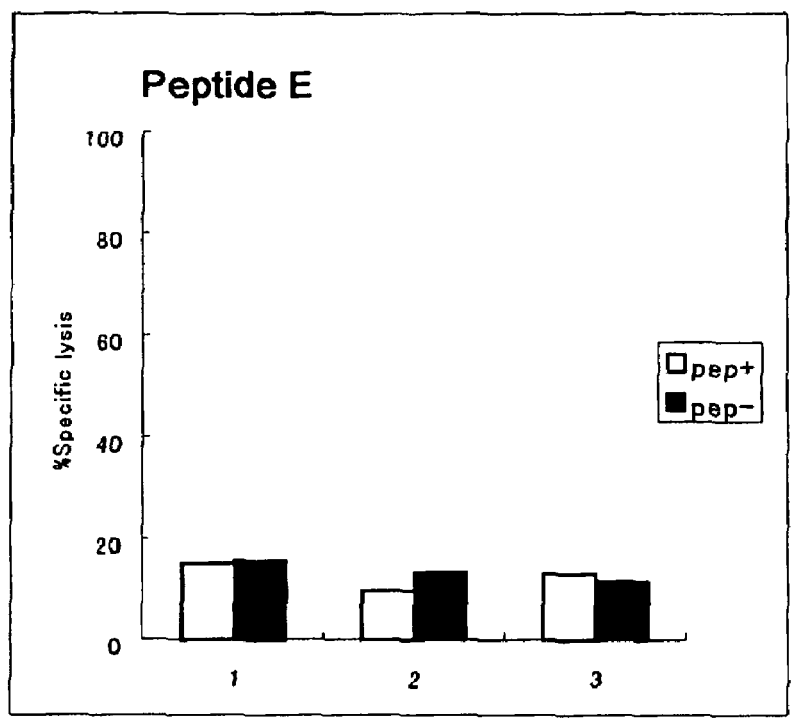
FIG. 14 is a graph showing that no specific CTL was induced when an HLA-A24 expressing transgenic mouse of the invention was immunized with an antigen peptide (peptide E, $WT1_{326-335}$) derived from human WT1. In the figure, the meanings of the vertical axis, the horizontal axis, the open bar, and the solid bar are the same as those described in regard to FIG. 6.
Figure 15:
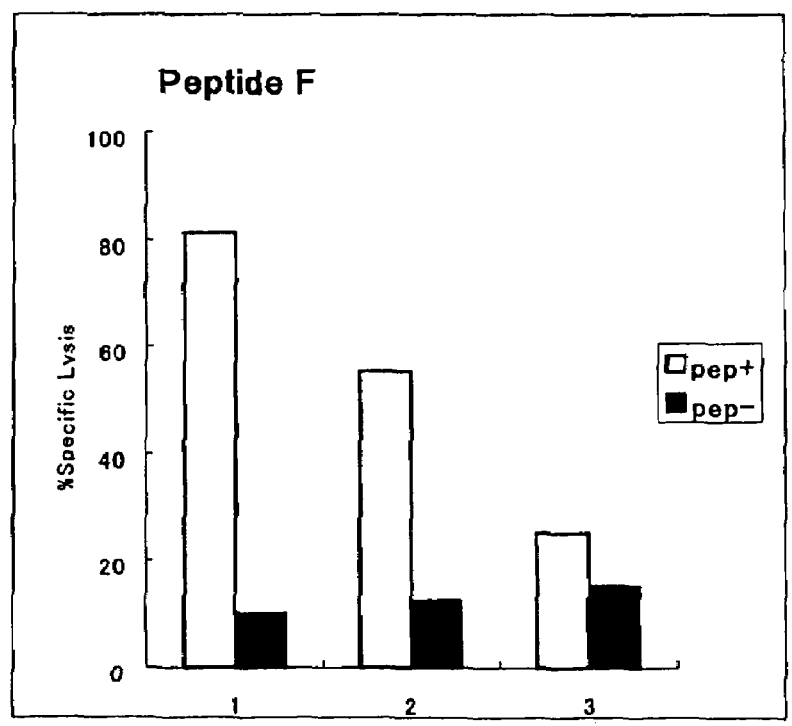
FIG. 15 is a graph showing that specific CTLs were induced when an HLA-A24 expressing transgenic mouse of the invention was immunized with the altered peptide (peptide F) wherein the amino acid residue at position 2 in an antigen peptide (peptide A, $WT1_{126-134}$) derived from human WT1 is altered into tyrosine. In the figure, the meanings of the vertical axis, the horizontal axis, the open bar, and the solid bar are the same as those described in regard to FIG. 6.
Figure 16:
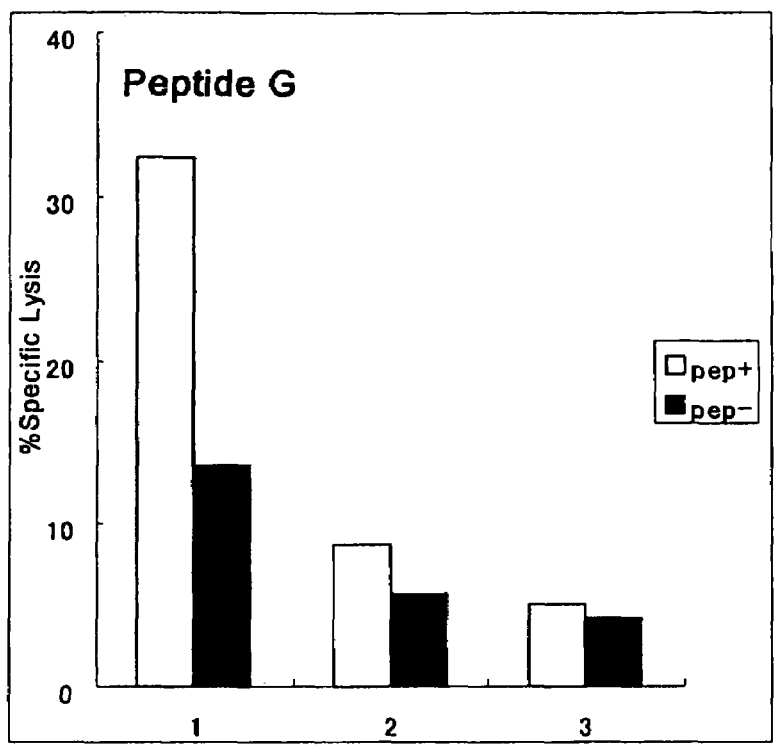
FIG. 16 is a graph showing that specific CTLs were induced when an HLA-A24 expressing transgenic mouse of the invention was immunized with the altered peptide (peptide G) wherein the amino acid residue at position 2 in an antigen peptide (peptide B, $WT1_{302-310}$) derived from human WT1 is altered into tyrosine. In the figure, the meanings of the vertical axis, the horizontal axis, the open bar, and the solid bar are the same as those described in regard to FIG. 6.
Figure 17:
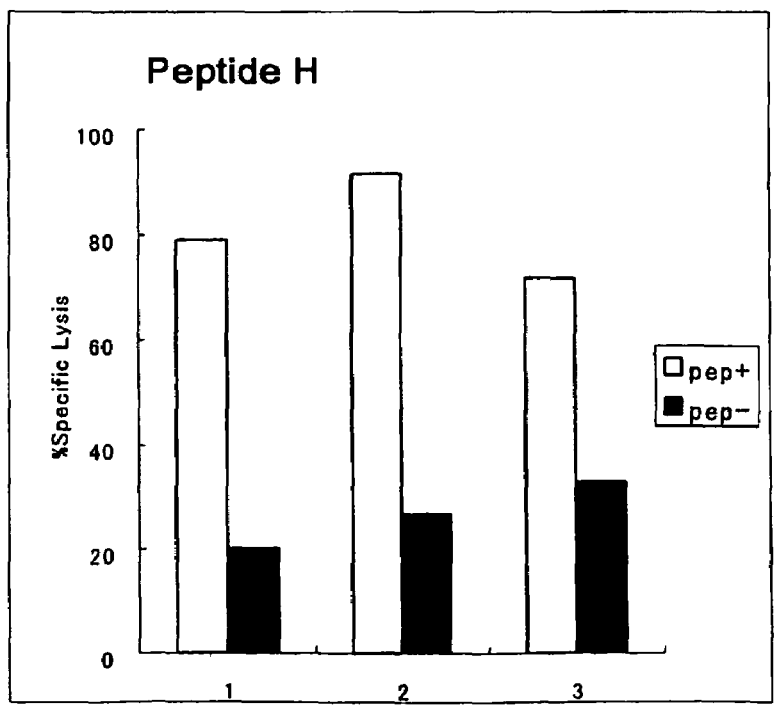
FIG. 17 is a graph showing that specific CTLs were induced when an HLA-A24 expressing transgenic mouse of the invention was immunized with the altered peptide (peptide H) wherein the amino acid residue at position 2 in an antigen peptide (peptide C, $WT1_{417-425}$) derived from human WT1 is altered into tyrosine. In the figure, the meanings of the vertical axis, the horizontal axis, the open bar, and the solid bar are the same as those described in regard to FIG. 6.
Figure 18:
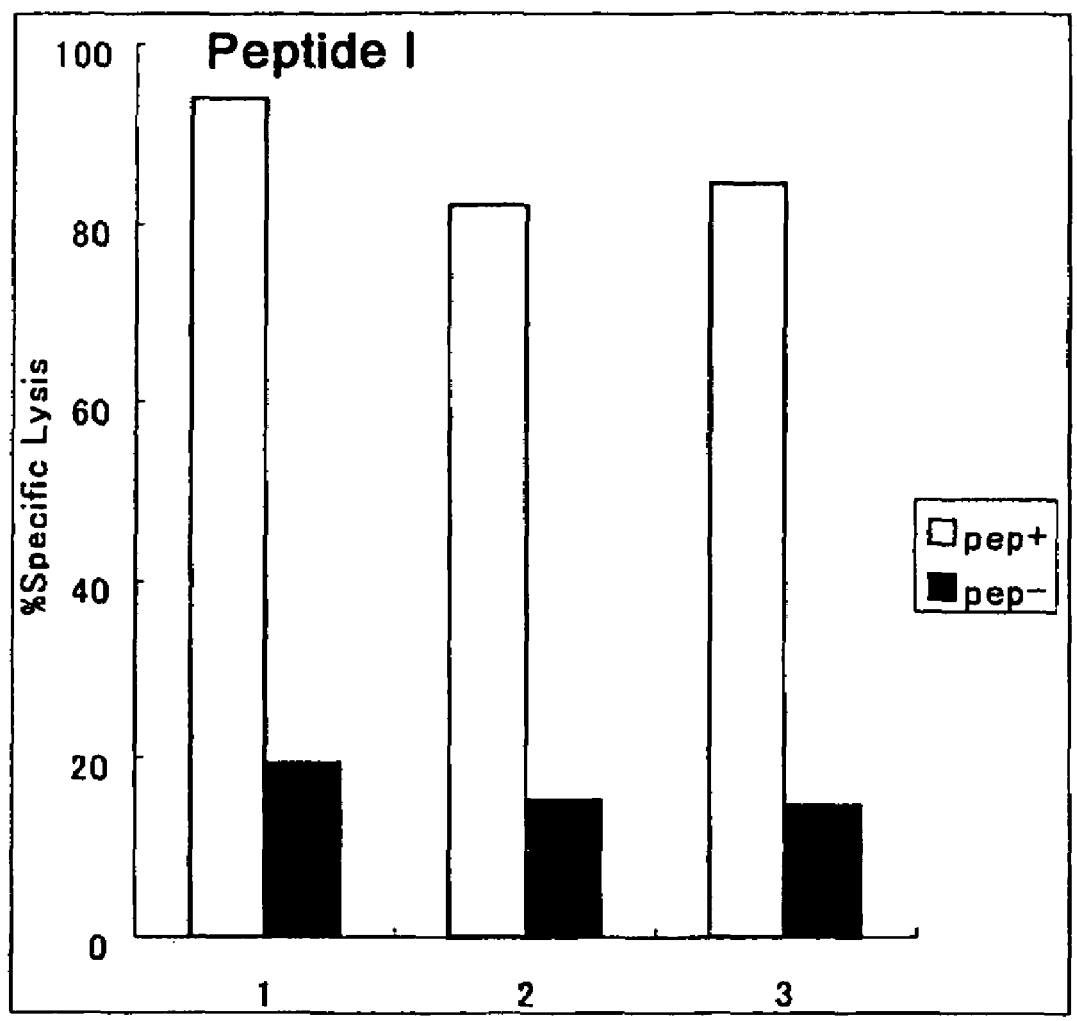
FIG. 18 is a graph showing that specific CTLs were induced when an HLA-A24 expressing transgenic mouse of the invention was immunized with the altered peptide (peptide I) wherein the amino acid residue at position 2 in an antigen peptide (peptide K, $WT1_{10-18}$) derived from human WT1 is altered into tyrosine. In the figure, the meanings of the vertical axis, the horizontal axis, the open bar, and the solid bar are the same as those described in regard to FIG. 6.
Figure 19:
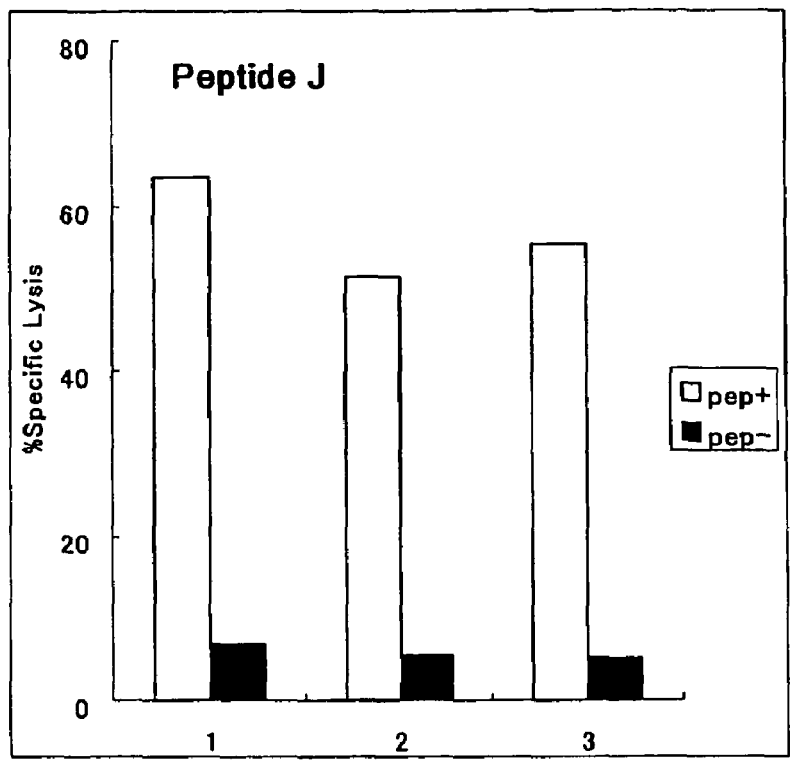
FIG. 19 is a graph showing that specific CTLs were induced when an HLA-A24 expressing transgenic mouse of the invention was immunized with the altered peptide (peptide J) wherein the amino acid residue at position 2 in an antigen peptide (peptide L, $WT1_{239-247}$) derived from human WT1 is altered into tyrosine. In the figure, the meanings of the vertical axis, the horizontal axis, the open bar, and the solid bar are the same as those described in regard to FIG. 6.

Furthermore, the CTL inducing ability was tested in the same manner using MAGE-$3_{195-203}$ (SEQ ID NO: 47), $CEA_{652-660}$ (SEQ ID NO: 48) and $CEA_{268-277}$ (SEQ ID NO: 49), which are also known to be HLA-A24-restriced cancer antigen peptide like HER-2/$neu_{780-788}$. The results are shown in FIG. 7 to 9. As a result, induction of specific CTLs by stimulation with these known HLA-A24-restiticed cancer antigen peptides was observed.

From these results, the HLA-A24 transgenic mouse of the invention were revealed to be an animal model for human that can be used for evaluation of HLA-A24-restricted cancer antigen proteins or cancer antigen peptides in vivo.

Example 1

CTL-Inducing Activities of Natural Peptides Derived from Human WT1 and Altered Peptides The amino acid sequence of human WT1 was searched for the sequence expected to bind an HLA-A24 antigen using BIMAS software that is to search for a sequence capable to bind an HLA antigen (http://bimas.dcrt nih.gov/molbio/hla_bind/). The search identified the following peptides:

```
peptide A:  Arg Met Phe Pro Asn Ala Pro Tyr Leu,       (SEQ ID NO: 8)

peptide B:  Arg Val Pro Gly Val Ala Pro Thr Leu,       (SEQ ID NO: 7)

peptide C:  Arg Trp Pro Ser Cys Gln Lys Lys Phe,       (SEQ ID NO: 9)

peptide D:  Gln Tyr Arg Ile His Thr His Gly Val Phe    (SEQ ID NO: 10)
and peptide E:  Ala Tyr Pro Gly Cys Asn Lys Arg Tyr Phe.   (SEQ ID NO: 11)
```

Peptides A, B, C, D, and E correspond to the sequences at positions from 126 to 134, from 302 to 310, from 417 to 425, from 285 to 294, and from 326 to 335 of the amino acid sequence of human WT1, respectively. These peptides were synthesized using Fmoc method.

Altered peptides wherein the amino acid at position 2 in the natural forms: peptides A to C is altered into tyrosine were also synthesized using Fmoc method:

```
peptide F:
Arg Tyr Phe Pro Asn Ala Pro Tyr Leu,   (SEQ ID NO: 2)

peptide G:
Arg Tyr Pro Gly Val Ala Pro Thr Leu    (SEQ ID NO: 3)
and peptide H:
Arg Tyr Pro Ser Cys Gln Lys Lys Phe.   (SEQ ID NO: 4)
```

Immunogenicity of each antigen peptide was evaluated using the HLA-A2402/$K^b$ transgenic mouse as constructed in aforementioned References. For the evaluation of each peptide for its immunogenicity, three transgenic mice were immunized with one peptide.

The transgenic mice were immunized with each synthesized peptide in association with tetanus toxin-derived mouse MHC class II I-$A^b$-restricted helper peptide (Phe Asn Asn Phe Thr Val Ser Phe Trp Leu Arg Val Pro Lys Val Ser Ala Ser His Leu Glu; SEQ ID NO: 32). Specifically, each antigen peptide and the helper peptide were adjusted to 40 mg/ml and 20 mg/ml, respectively, in DMSO, and diluted with a physiological saline to 2 mg/ml and 1 mg/ml, respectively. They were then mixed with an equal amount of Freund's incomplete adjuvant (IFA) using a glass syringe to prepare a water-in-oil emulsion. The resultant emulsion (200 μl) was injected into the HLA-A2402/$K^b$ transgenic mouse subcutaneously in the base of the tail for immunization. Seven days after the initiation of experiment, the spleen was removed and grounded on the frosted part of glass slide, and splenocytes were recovered and prepared. A portion of the splenocytes undergone hemolysis treatment with an ACK buffer (0.15 M $NH_4Cl$, 10 mM $KHCO_3$, 0.1 mM EDTA, pH 7.2-7.4) was exposed to X ray radiation (2,000 rad), then pulsed with the above-mentioned peptide (100 μg/ml) for 1 hour, and seeded into a 24-well plate at $7 \times 10^6$/well. Simultaneously, non-radiated, non-peptide-pulsed splenocytes ($7 \times 10^5$/well) were added together and stimulated in vitro at 37° C. for 6 days. The in vitro stimulation was carried out in RPMI1640 medium supplemented with 10% FCS, 10 mM HEPES, 20 mM L-glutamine, 1 mM sodium pyruvate, 1 mM MEM nonessential amino acids, 1% MEM vitamin and 55 μM 2-mercaptoethanol.

Then, the test for cytotoxic activity was conducted according to the conventional manner. Jurkat-A2402/$K^b$ cells (Reference 8), and Jurkat-A2402/$K^b$ cells pulsed with the peptide were used as target cells (T). These cells were labeled with $^{51}Cr$ (3.7 MBq/$10^6$ cells) and pulsed with the peptide at 100 μg/ml for one hour (The labeling was carried out over 2 hours, and 1 hour after the initiation of labeling, the peptide was added). Splenocytes in vitro stimulated and incubated were used as effector cells (E). They were combined and reacted at an E/T ratio of 80, and the cytotoxic activity was determined by $^{51}Cr$ release assay (*J. Immunol.*, 159:4753, 1997). The results are shown in FIGS. 10 to 17. The Y axis shows the cytotoxic activity, and the numbers: 1, 2, and 3 in the X axis show the numbers of the three mice.

These figures show that only peptide B has an immunogenicity among the five natural peptides from WT1 tested as shown above. The altered form: peptide G wherein the amino acid at position 2 in the natural form: peptide B is altered into tyrosine was shown to have a higher immunogenicity than peptide B. Also, although the natural forms: peptides A and C have no immunogenicity, the altered forms: peptides F and H wherein the amino acid at position 2 in the natural forms: peptides A and C is altered into tyrosine were shown to have a high immunogenicity.

From these results, the natural form: peptide B and the altered forms: peptides F, G and H were demonstrated to function as an antigen peptide having an activity to induce CTLs in vivo.

Example 2

CTL-Inducing Activities of Altered Peptides Derived from Human WT1 (II)

In a similar manner to Example 1, the following natural peptides (peptides K and L) searched and identified to have the sequence expected to bind an HLA-A24 antigen using BIMAS software, and altered peptides thereof (peptides I and J) wherein the amino acid at position 2 in the natural forms is altered into tyrosine, were synthesized using Fmoc method:

```
peptide K:  Ala Leu Leu Pro Ala Val Pro Ser Leu, (SEQ ID NO: 51)

peptide L:  Asn Gln Met Asn Leu Gly Ala Thr Leu, (SEQ ID NO: 52)

peptide I:  Ala Tyr Leu Pro Ala Val Pro Ser Leu, (SEQ ID NO: 5)
and peptide J:  Asn Tyr Met Asn Leu Gly Ala Thr Leu. (SEQ ID NO: 6)
```

Peptides K and L correspond to the sequences at positions from 10 to 18, and from 239 to 247 of the amino acid sequence of human WT1, respectively. Peptides I and J are the altered peptides wherein the amino acid at position 2 in peptides K and L is altered into tyrosine, respectively. Immunogenicity of each of these natural and altered peptides was evaluated in a similar manner to Example 1. The results are shown in FIGS. 18, 19, 21, and 22. The Y axis shows the cytotoxic activity, and the numbers: 1, 2, and 3 in the X axis show the numbers of the three mice.

These figures show that, although the natural forms: peptides K and L have no immunogenicity, both of the altered forms: peptides I and J have a high immunogenicity.

From the results, the WT1 altered forms: peptides I and J were demonstrated to function as an antigen peptide that induces cytotoxic T cells in vivo.

Example 3

Cytotoxic Activities of Altered Peptides Derived from Human WT1

Figure 20:
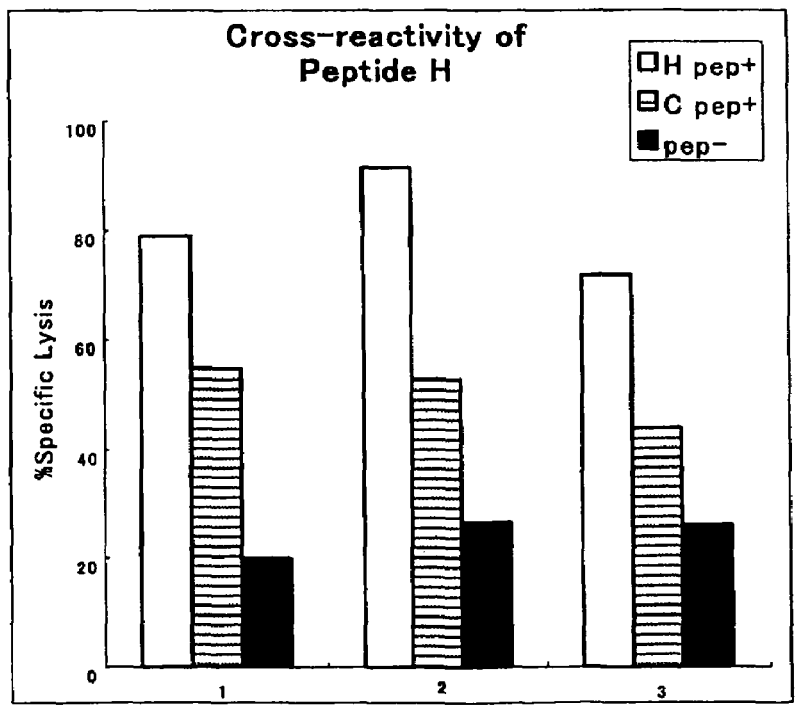
FIG. 20 is a graph showing the results of the test for cross-reactivity of the effector cells induced by the altered peptide; peptide H to natural peptides. In the figure, the vertical axis shows the CTL-inducing activity (% Specific Lysis), and the horizontal axis shows the name of respective transgenic mice. Also, in the figure, the open bar shows the results obtained using target cells pulsed with the altered peptide (peptide H), the dotted bar shows the results obtained using target cells pulsed with the natural peptide (peptide C), and the solid bar shows the results obtained using cells not pulsed with any peptide.
Figure 21:
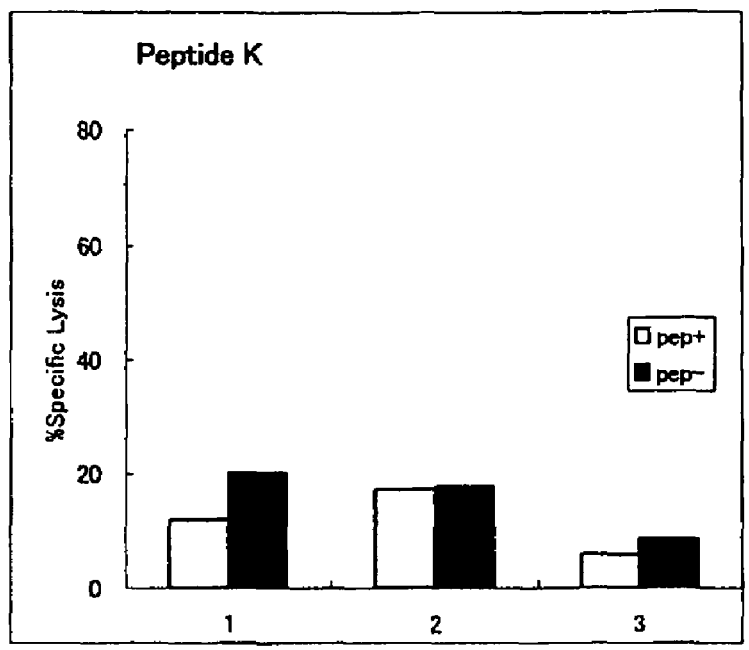
FIG. 21 is a graph showing that no specific CTL was induced when an HLA-A24 expressing transgenic mouse of the invention was immunized with an antigen peptide (peptide K, $WT1_{10-18}$) derived from human WT1. In the figure, the meanings of the vertical axis, the horizontal axis, the open bar, and the solid bar are the same as those described in regard to FIG. 6.
Figure 22:
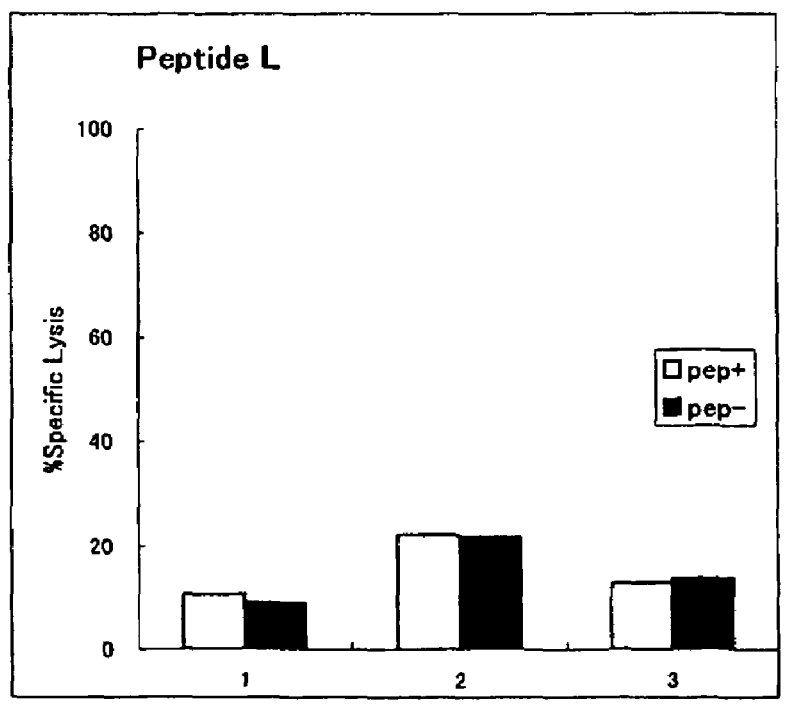
FIG. 22 is a graph showing that no specific CTL was induced when an HLA-A24 expressing transgenic mouse of the invention was immunized with an antigen peptide (peptide L, $WT1_{239-247}$) derived from human WT1. In the figure, the meanings of the vertical axis, the horizontal axis, the open bar, and the solid bar are the same as those described in regard to FIG. 6.

Cross-reactivity of the effector cells induced by the altered peptide to the natural peptide was tested. Effector cells induced by immunizing the mice with the altered form: peptide H (E) and target cells of the Jurkat-A2402/$K^b$ cells pulsed with the natural form: peptide C (T) were combined and reacted at an E/T ratio of 80, and the cytotoxic activity was determined by $^{51}$Cr release assay. The results are shown in FIG. 20. The figure shows that the effector cells induced by the WT1 altered peptide exhibited a cytotoxic activity against both cells pulsed with the altered and natural forms.

Example 4

CTL Induction from Human Peripheral Blood Mononuclear Cells by Altered Peptides derived from Human WT1

Peripheral blood mononuclear cells were separated from healthy donors positive for HLA-A2402, and were placed into wells of a 24-well plate at 4×10$^6$ cells/well. To the wells, the natural peptide of SEQ ID NO: 7 or the altered peptide of SEQ ID NO: 3 was added at a concentration of 10 μM, and the mixture was incubated for a week in a culture medium comprising 45% RPMI1640, 45% AIV, 10% inactivated human AB serum, 1× nonessential amino acids, 25 ng/ml 2-mercaptoethanol, 50 mg/ml streptomycin, and 50 U/ml penicillin. After the incubation, the cells were adjusted to 2×10$^6$ cells/well, which were used as responder cells hereafter. On the other hand, peripheral blood mononuclear cells separated from the same healthy donors were incubated together with 10 μM of either of these peptides for 4 hours to accomplish the pulsing with peptide, and then radiated at 30 Gy. The cells were adjusted to 4×10$^6$ cells/well, which were used as stimulator cells hereafter.

Figure 23:
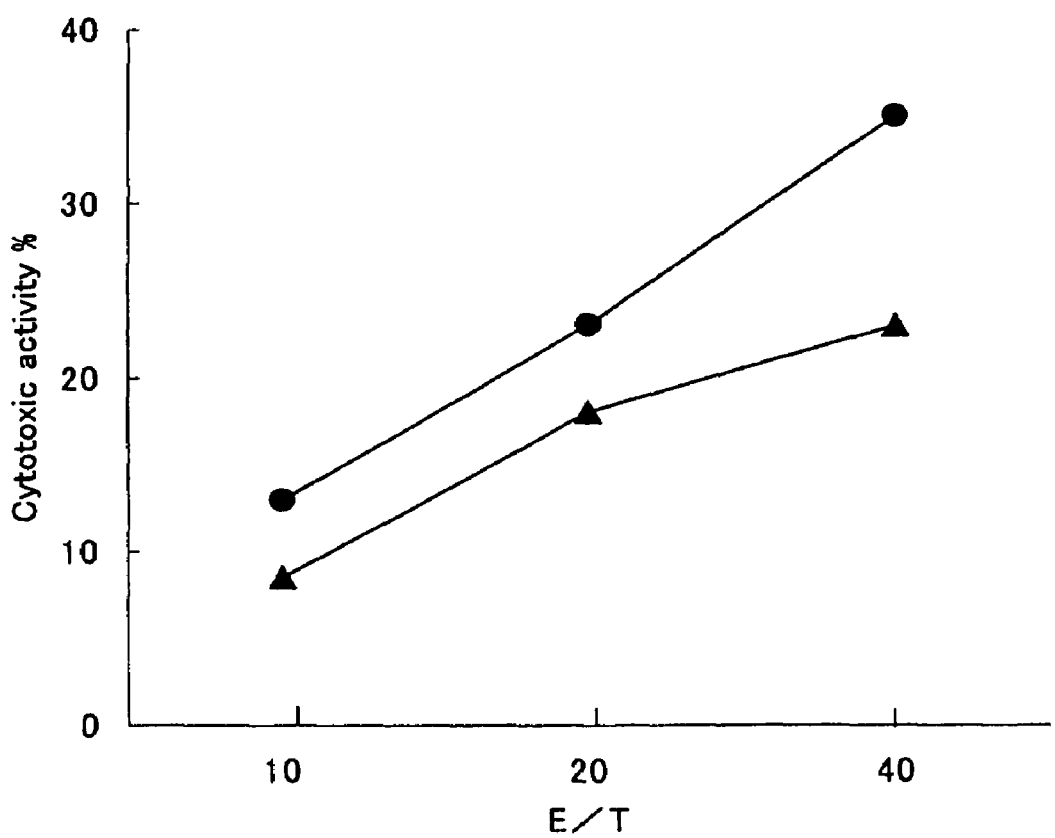
FIG. 23 is a graph showing that CTLs were induced when peripheral blood mononuclear cells from healthy donors positive for HLA-A2402 were stimulated in vitro with an antigen peptide (peptide B, $WT1_{302-310}$) derived from human WT1, or the altered peptide thereof (peptide G) wherein the amino acid residue at position 2 in peptide B is altered into tyrosine. In the figure, the vertical axis shows the cytotoxic activity, and the horizontal axis shows the ratio of effector cells (E) and target cells (T), E/T. The solid circle and the solid triangle show the cytotoxic activities of the effector cells stimulated with the multi-altered peptide, and the natural peptide, respectively.
Figure 25:
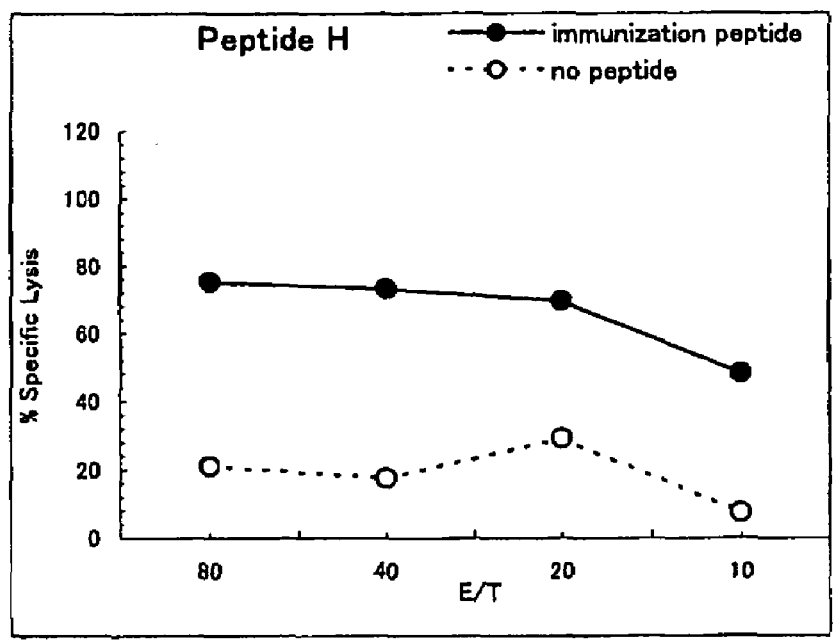
FIG. 25 is a graph showing that specific CTLs were induced when an HLA-A24 expressing transgenic mouse was immunized with peptide H. In the figure, the vertical axis shows the cytotoxic activity (% Specific Lysis), and the horizontal axis shows the E/T ratio. The solid circle and the open circle show the results obtained using target cells pulsed with peptide H (immunogenic peptide), and the results obtained with cells not pulsed with any peptide, respectively.
Figure 26:
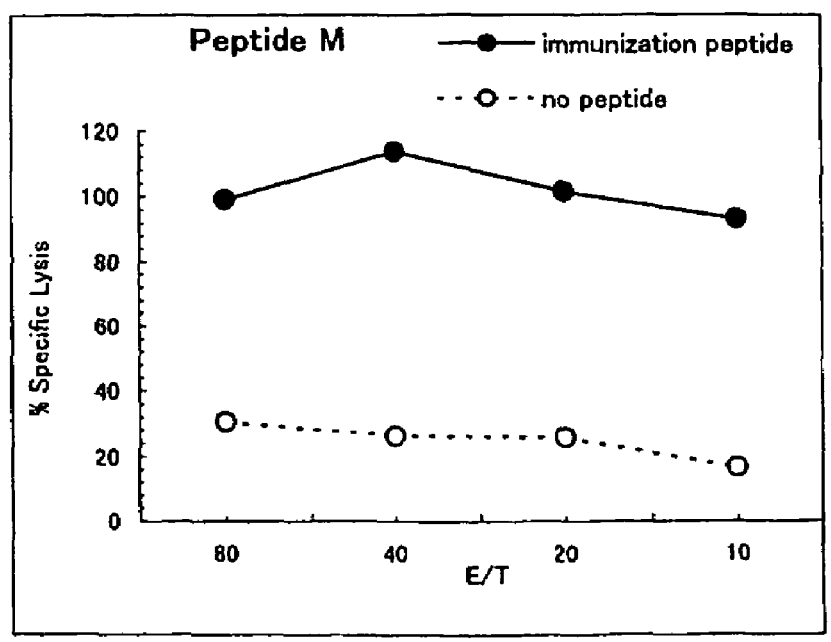
FIG. 26 is a graph showing that specific CTLs were induced when an HLA-A24 expressing transgenic mouse was immunized with peptide M. In the figure, the meanings of the vertical axis, the horizontal axis, the solid circle, and the open circle are the same as those described in regard to FIG. 25.
Figure 27:
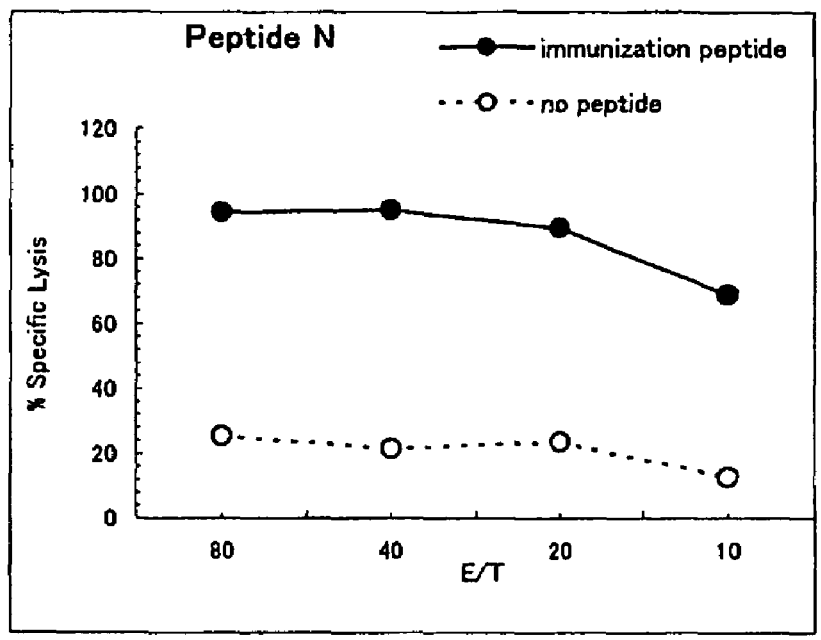
FIG. 27 is a graph showing that specific CTLs were induced when an HLA-A24 expressing transgenic mouse was immunized with peptide N. In the figure, the meanings of the vertical axis, the horizontal axis, the solid circle, and the open circle are the same as those described in regard to FIG. 25.
Figure 28:
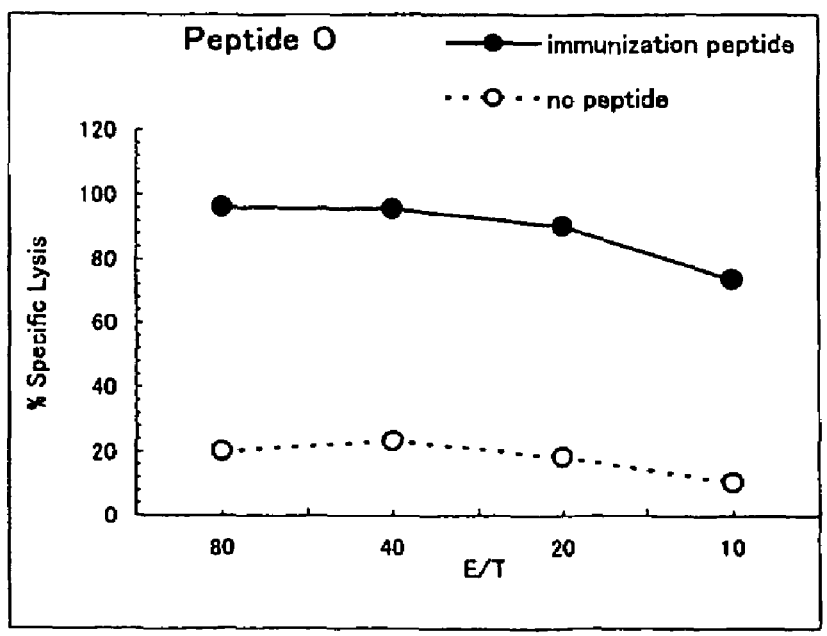
FIG. 28 is a graph showing that specific CTLs were induced when an HLA-A24 expressing transgenic mouse was immunized with peptide O. In the figure, the meanings of the vertical axis, the horizontal axis, the solid circle, and the open circle are the same as those described in regard to FIG. 25.

The responder cells and the stimulator cells thus prepared were mixed together, and the mixture was added with IL-2 at 30 U/ml, and incubated. A similar stimulation of the responder cells with the stimulator cells was conducted three times with an interval of a week. The cytotoxic activity in those cells thus obtained was determined by $^{51}$Cr release assay wherein the cytotoxic activity was determined by reacting the C1R-A*2402 cells positive for an HLA-A24 (Int. J. Cancer, 81, p 387, 1999) labeled with $^{51}$Cr that were pulsed with the natural peptide of SEQ ID NO: 7 as target cells (T), and the cells stimulated with the natural peptide of SEQ ID NO: 7 or the altered peptide of SEQ ID NO: 3 as described above (effector cells)(E) at an E/T ratio of 10, 20 or 40. The results are shown in FIG. 23. The figure shows that the altered peptide can induce CTLs that recognize the natural peptide, and exhibits a superior CTLs-inducing activity to the natural peptide. Further, a lung cancer cell line positive for WT1 and positive for an HLA-A24, RERF-LC-AI cells; a lung cancer cell line positive for WT1 and negative for an HLA-A2402, 11-18 cells; or a lung cancer cell line negative for WT1 and positive for an HLA-A24, 11-18 cells were used as target cells to determine the cytotoxic activities of the effector cells described above in a similar manner by $^{51}$Cr release assay. The results are shown in FIG. 24. The figure shows that the effector cells stimulated with the altered peptide and the natural peptide specifically injured only the RERF-LC-AI cells, which were positive both for WT1 and for an HLA-A2402, showing that CTLs that were specific for WT1, and were HLA-A2402-restricted, were induced by the stimulation with the peptides. It was been also shown that the altered peptide exhibits a superior CTLs-inducing activity to the natural peptide.

Example 5

CTL-Inducing Activities of Peptides wherein Cysteine Residue is Substituted

Peptide H (Arg Tyr Pro Ser Cys Gln Lys Lys Phe; SEQ ID NO: 4) contains a cysteine residue at position 5. The cysteine residue may be oxidized in a solution to form a disulfide bond. To avoid this, the substituted forms: peptides M, N, and O wherein the cysteine reside at position 5 is substituted with a serine residue, an alanine residue, or an α-aminobutyric acid were synthesized, and the immunogenicity of each peptide was evaluated in vivo:

```
peptide M:  Arg-Tyr-Pro-Ser-Ser-Gln-Lys-Lys-Phe, (SEQ ID NO: 66)

peptide N:  Arg-Tyr-Pro-Ser-Ala-Gln-Lys-Lys-Phe  (SEQ ID NO: 67)
and peptide O:  Arg-Tyr-Pro-Ser-Abu-Gln-Lys-Lys-Phe. (SEQ ID NO: 68)
```

These substituted forms: peptides M, N, and O were synthesized using Fmoc method, and their immunogenicities were evaluated in a similar manner to Example 1. In the test for cytotoxic activity, splenocytes in vitro stimulated and incubated were used as effector cells (E), and were mixed with target cells at various ratios to determine the cytotoxic activities of the effector cells by $^{51}$Cr release assay (*J. Immunol.*, 1997; 159:4753). The results are shown in FIGS. 25 to 28. In the figure, the vertical axis shows the cytotoxic activity, and the horizontal axis shows the E/T ratio.

The figure shows that peptides M, N, and O wherein the cysteine reside at position 5 in peptide H is substituted with a serine residue, an alanine residue, or an α-aminobutyric acid, have an immunogenicity equivalent to the non-substituted peptide, peptide H.

Example 6

Cytotoxic Activities of Peptides wherein Cysteine Residue is Substituted

Figure 29:
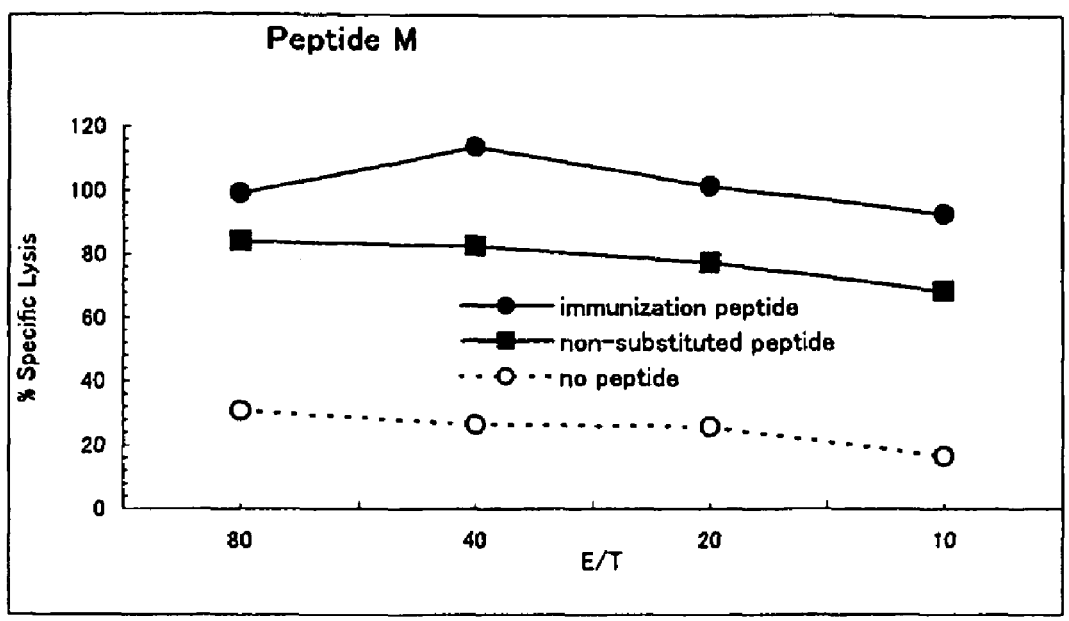
FIG. 29 is a graph showing the results of the test for cross-reaction of the effector cells induced by the substituted peptide; peptide M to the non-substituted peptide; peptide H. In the figure, the vertical axis shows the CTL-inducing activity (% Specific Lysis), and the horizontal axis shows the E/T ratio. Also, in the figure, the solid circle, the solid square, and the open circle show the results obtained using target cells pulsed with peptide M (immunogenic peptide), peptide H, and using cells not pulsed with any peptide.
Figure 30:
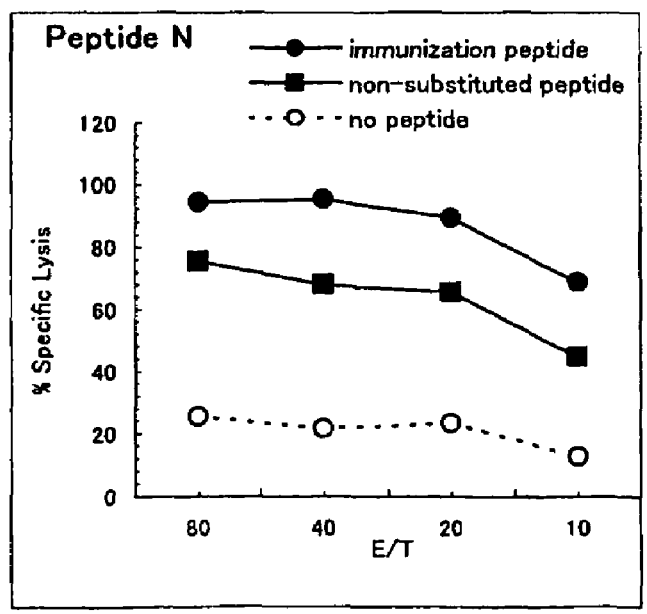
FIG. 30 is a graph showing the results of the test for cross-reaction of the effector cells induced by the substituted peptide; peptide N to the non-substituted peptide; peptide H. In the figure, the meanings of the vertical axis, the horizontal axis, the solid circle, to solid square and the open circle are the same as those described in regard to FIG. 29.

Cross-reactivity of the effector cells induced by the substituted peptide to the non-substituted peptide was tested. To effector cells induced by immunizing the mice with peptide M or N (E), target cells of the Jurkat-A2402/K$^b$ cells pulsed with peptide M or N, with peptide H, or without any peptide (T) were reacted, and the cytotoxic activities of the effector cells were determined by $^{51}$Cr release assay. The results are shown in FIGS. 29 and 30.

The figures show that the effector cells induced by the substituted peptides exhibited a cytotoxic activity against all of the cells pulsed with the substituted peptides (peptides M and N; immunization peptide in the figure), and the non-substituted peptide (peptide H).

INDUSTRIAL APPLICABILITY

According to the present invention, an HLA-A24-restricted peptide derived from WT1 which has an activity to induce CTLs in vivo, a polynucleotide encoding said peptide, or a cancer vaccine which comprises the peptide or the polynucleotide. The cancer vaccine of the invention can be used to treat many cancer patients.

The invention claimed is:

1. An isolated peptide comprising the amino acid sequence:

Ala Tyr Leu Pro Ala Val Pro Ser Leu  (SEQ ID NO: 5).

2. The isolated peptide of claim 1, which consists of the amino acid sequence of SEQ ID NO: 5.

3. A pharmaceutical composition comprising the isolated peptide of claim 1 and a pharmaceutically acceptable carrier.

4. A pharmaceutical composition comprising the isolated peptide of claim 2 and a pharmaceutically acceptable carrier.

* * * * *